US012589113B2

(12) United States Patent
Jiang

(10) Patent No.: US 12,589,113 B2
(45) Date of Patent: Mar. 31, 2026

(54) PREPARATION OF A THERAPEUTIC COMPOSITION FOR TREATING AUTOIMMUNE DISEASES

(71) Applicant: Avotres, Inc., Cedar Knolls, NJ (US)

(72) Inventor: Hong Jiang, Fort Lee, NJ (US)

(73) Assignee: Avotres, Inc., Cedar Knolls, NJ (US)

( * ) Notice: Subject to any disclaimer, the term of this patent is extended or adjusted under 35 U.S.C. 154(b) by 0 days.

(21) Appl. No.: 18/903,162

(22) Filed: Oct. 1, 2024

(65) Prior Publication Data

US 2025/0017972 A1 Jan. 16, 2025

Related U.S. Application Data

(62) Division of application No. 17/827,089, filed on May 27, 2022.

(60) Provisional application No. 63/297,354, filed on Jan. 7, 2022, provisional application No. 63/195,087, filed on May 31, 2021.

(51) Int. Cl.
| | |
|---|---|
| *A61K 40/19* | (2025.01) |
| *A61K 31/10* | (2006.01) |
| *A61K 35/15* | (2015.01) |
| *A61K 35/17* | (2015.01) |
| *A61K 38/17* | (2006.01) |
| *A61K 38/38* | (2006.01) |
| *A61K 40/22* | (2025.01) |
| *A61K 40/24* | (2025.01) |
| *A61K 40/41* | (2025.01) |
| *A61K 40/42* | (2025.01) |
| *A61K 47/20* | (2006.01) |
| *A61K 47/42* | (2017.01) |
| *A61P 17/06* | (2006.01) |
| *A61P 19/02* | (2006.01) |
| *A61P 25/28* | (2006.01) |
| *A61P 37/02* | (2006.01) |
| *A61P 37/04* | (2006.01) |
| *A61P 37/06* | (2006.01) |
| *C07K 14/74* | (2006.01) |
| *C12N 5/0783* | (2010.01) |
| *C12N 5/0784* | (2010.01) |
| *G01N 33/50* | (2006.01) |

(52) U.S. Cl.
CPC .............. *A61K 35/17* (2013.01); *A61K 31/10* (2013.01); *A61K 35/15* (2013.01); *A61K 38/1709* (2013.01); *A61K 38/38* (2013.01); *A61K 40/19* (2025.01); *A61K 40/22* (2025.01); *A61K 40/24* (2025.01); *A61K 40/416* (2025.01); *A61K 40/4262* (2025.01); *A61K 47/20* (2013.01); *A61K 47/42* (2013.01); *A61P 17/06* (2018.01); *A61P 19/02* (2018.01); *A61P 25/28* (2018.01); *A61P 37/02* (2018.01); *A61P 37/04* (2018.01); *A61P 37/06* (2018.01); *C07K 14/70539* (2013.01); *C12N 5/0637* (2013.01); *C12N 5/0639* (2013.01); *G01N 33/505* (2013.01); *C12N 2501/22* (2013.01); *C12N 2501/2304* (2013.01)

(58) Field of Classification Search
None
See application file for complete search history.

(56) References Cited

U.S. PATENT DOCUMENTS

2019/0389953 A1* 12/2019 Jiang .............. A61K 39/464476
2022/0280563 A1* 9/2022 Mevorach ............ A61K 40/416

OTHER PUBLICATIONS

Liu et al. ( Cellular and Molecular Immunol, 2014, v.11, pp. 169-174).*
Jiang et al ( J of clinical Investigat; 2010, v.120, pp. 3641-3650.*
Schnitzer et al (Vaccine, 2010,28,5785-5793).*

* cited by examiner

*Primary Examiner* — Michail A Belyavsky
(74) *Attorney, Agent, or Firm* — Buchanan Ingersoll & Rooney PC

(57) ABSTRACT

The present invention provides a composition comprising dendritic cells loaded with hHsp60sp, which dendritic cells are from a subject and have been fixed with paraformaldehyde (PFA). The subject may suffer from an autoimmune disease. Also provided are a method for preparing the composition; recombinant human cells comprising a heterologous gene encoding a fusion protein of HLA-E and hHsp60sp or B7sp, and expressing the fusion protein on the surface of the cells; a method for determining a percentage of maximum inhibition of testing the function of the HLA-E restricted CD8+ Treg cells from a subject, determining whether HLA-E restricted CD8+ Treg cells freshly isolated from a subject are defective, or determining whether defective HLA-E restricted CD8+ Treg cells from a subject are correctable; and a method for correcting defective HLA-E restricted CD8+ Treg cells, treating type 1 diabetes (T1D), or treating multiple sclerosis (MS).

9 Claims, 12 Drawing Sheets

Specification includes a Sequence Listing.

Control vs. Patient
(Before Treatment)

Control
(Before vs. after Treatment)

Patient
(Before vs after Treatment)

Control vs. Patient
(Before Treatment)

Control vs. Patient (Before Treatment)

Control (Before vs. after Treatment)

Control
(Before vs. after Treatment)

Patient
(Before vs after Treatment)

Control
(Before vs. after Treatment)

Patient
(Before vs after Treatment)

Patient
(Before vs after Treatment)

Control vs. Patient
(Before Treatment)

1

PREPARATION OF A THERAPEUTIC COMPOSITION FOR TREATING AUTOIMMUNE DISEASES

CROSS-REFERENCE TO RELATED APPLICATION

This application is a divisional application of application Ser. No. 17/827,089, filed May 27, 2022, which claims priority to U.S. Provisional Application No. 63/195,087, filed May 31, 2021, and U.S. Provisional Application No. 63/297,354, filed Jan. 7, 2022, the contents of each of which are incorporated herein by reference in their entireties for all purposes.

REFERENCE TO SEQUENCE LISTING

The present application is being filed along with a Sequence Listing in electronic format. The Sequence Listing is provided as a file entitled AVO-102US_SequenceListing.txt, created May 26, 2022, which is 1,233 bytes in size. The information in the electronic format of the Sequence Listing is incorporated herein by reference in its entirety.

FIELD OF THE INVENTION

The invention relates to dendritic cells derived from a subject, which were loaded with hHsp60sp and fixed with paraformaldehyde, and uses thereof for correcting defective regulatory CD8+ T cells in the same subject and/or treating one or more autoimmune diseases in the same subject.

BACKGROUND OF THE INVENTION

Autoimmune diseases result from breakdown in mechanisms that maintain unresponsiveness to self. For example, type 1 diabetes (T1D) is an autoimmune disorder in which T cells are self-reactive or activated T cells that are activated against major antigenic components of pancreatic β cells are out of the control by the normal regulatory mechanisms. While these self-reactive T cells are under the control of peripheral regulatory mechanisms in healthy individuals, failure of control leads to destruction of the B cells and subsequent T1D. The autoimmune attack on pancreatic β cells is orchestrated by a variety of cells that either by directly killing the B cells or, indirectly, by producing cytokines and other toxic mediators to damage the B cells. The facts that these self-reactive T cells work together with other lymphocytes and antigen-presenting cells to mediate this damage have been shown in animal models to be important both in the early stages of diabetes development and in the final effector stages.

Selective control of unwanted immune responses could be achieved by induction of "antigen-specific tolerance", provided that the specific antigens that elicit the unwanted immune responses have been identified. However, induction of "antigen specific tolerance" requires precise knowledge of the peptide associated with particular MHC molecules and the highly polymorphic human HLA system inevitably increase the uncertainty and puts a huge burden on searching for such a MHC/peptide complex in each patient. Thus, the necessity of identification of a precise MHC/peptide complex for each individual from an unknown and countless antigen pool makes the induction of "antigen-specific tolerance" an unfeasible approach or may be an "impossible mission" to specifically and effectively treat organ specific autoimmune diseases and/or control graft rejection in clinical immunology.

HLA-E restricted CD8+ regulatory T cells, provide a simple and unified "class action" of self-nonself discrimination, regulating the unwanted anti-self immune responses, independent of the knowledge of any particular pathogenic antigens, which are largely undetermined, in autoimmune diseases and/or graft rejection.

A subset of HLA-E restricted regulatory CD8+ T cells are known to selectively down-regulate all potentially pathogenic self-reactive T cells by specifically recognizing a common target structure, i.e., a family of peptides, represented by Hsp60sp, associated with HLA-E expressed on pathogenic self-reactive T cells. Such pathogenic self-reactive T cells are responsible for a variety of autoimmune diseases. The dysfunction or failure of this Q/E CD8+ Treg cell subset to recognize, or to suppress, its target population results in a permissive state, in which organ-specific autoimmunity may emerge.

The HLA-E restricted regulatory CD8+ T cells selectively down-regulate the self-reactive T cell pool by specifically recognizing a Biomarker (HLA-E/Hsp60sp peptide complex) preferentially expressed on the self-reactive T cells regardless of which antigens activated the target T cells. Such unique feature presents a rarely seen therapeutic advantage to target a wide spectrum of autoimmune diseases and other immunologically relevant conditions without the necessity to identify the disease specific pathogenic antigens, which is an extremely challenging task currently.

U.S. Pat. No. 9,421,249 ("the '249 patent") discloses a murine composition for activation of Qa-1 restricted CD8+ T cells so as to suppress murine autoreactive T cells. The composition of the '249 patent comprises a murine dendritic cell loaded extracellularly with a murine Hsp60sp peptide. The association of dendritic cells with human Hsp60sp peptide is known unstable. Further, Jiang (*JCI* 120 (10): 3641-3650 (2010)) discloses that a majority of people with Type 1 diabetes who were tested in the study were found to have a defect in CD8+ T cell recognition of HLA-E/hHsp60sp, which was associated with failure of self/non-self discrimination, and the defect in the CD8+ T cells from most of the T1D patients tested could be corrected in vitro by exposure to autologous immature dendritic cells loaded with hHsp60sp in vitro. However, no clinical use of autologous immature dendritic cells loaded with hHsp60sp has been performed to correct the defect in HLA-E restricted CD8+ T cells when administered to a human individual (e.g., patient). It was unknown whether other autoimmune patients have defective HLA-E restricted CD8+ T cells that are correctable in vitro by autologous immature dendritic cells loaded with hHsp60sp. Nor has there been any clinical use of any autologous immature dendritic cells loaded with hHsp60sp, let alone with demonstrated stability and efficacy for correcting defective HLA-E restricted CD8+ Treg cells or treating an autoimmune disease (e.g., T1D) in a human individual (e.g., patient).

Table 1 summarizes the dose regimens and routes of administration of dendritic cell-based therapies in some human clinical trials, which have been determined to be safe for use.

TABLE 1

| | Dendritic cell-based therapies | | |
| Therapy to | Dose/schedule | Route | Number Subjects |
| --- | --- | --- | --- |
| NHL (Non-Hodgkin's lymphoma) | $2\text{-}17 \times 10^{6}/4$ weeks $\times$ 4 | i.v. | 35 |
| | $2\text{-}17 \times 10^{6}/4$ weeks $\times$ 4 | i.v. | 10 |
| Melanoma | $5\text{-}50 \times 10^{6}/2$ weeks $\times$ 4 | i.v./i.d./i.n. | 28 |
| | $5\text{-}50 \times 10^{6}/2$ weeks $\times$ 4 | i.v. | 14 |
| | $3 \times 10^{6} + 6/12 \times 10^{6}/2$ weeks $\times$ 5 | i.d. + i.v. | 13 |
| Myeloma | $0.5\text{-}11 \times 10^{6}/4$ weeks $\times$ 2 | i.v. | 12 |
| | $3.5\text{-}89 \times 10^{6}/2$ weeks $\times$ 3 | i.v. | 6 |
| Prostate cancer | $1\text{-}20 \times 10^{6}/6\text{-}8$ weeks $\times$ 4-5 | i.v. | 51 |
| | $10 \times 10^{6}/2$ weeks $\times$ 4 | i.v. + i.d. | 8 |
| | $0.3\text{-}40 \times 10^{6}/4$ weeks $\times$ 2 | i.v./i.d./i.l. | 21 |
| | $10 \times 10^{6}/2$ weeks $\times$ 3 | i.v. + i.d. | 13 |
| | $0.94\text{-}2.02 \times 10^{8}/$ 4 weeks $\times$ 3 | i.v. | 14 |
| RCC (Renal cell carcinoma) | $5\text{-}10 \times 10^{6}/4$ weeks $\times$ 3-13 | i.v./i.d. | 35 |
| | $10\text{-}50 \times 10^{6} + 10 \times 10^{6}/2$weeks $\times$ 3 | i.v. + i.d. | 10 |
| Type 1 diabetes | $10 \times 10^{6}/2$ weeks $\times$ 4 | i.d. | 10 |

There remains a need for stable autologous dendritic cells loaded with hHsp60sp capable of correcting defective HLA-E restricted CD8+ T cells or treating an autoimmune disease such as, e.g. T1D, in a subject in need thereof and reliable methods for identifying a subject having defective HLA-E restricted CD8+ Treg cells that are correctable by the autologous dendritic cells loaded with hHsp60sp.

SUMMARY OF THE INVENTION

The present invention provides dendritic cells (DCs) prepared from a subject and loaded with human heat shock protein 60 signal peptide (hHsp60sp), also known as hHsp60sp pulsed DCs and uses thereof. The inventor has discovered that fixation of the hHsp60sp pulsed DCs with 2% paraformaldehyde (PFA) stabilizes the association between the DCs and the hHsp60sp. The resulting fixed hHsp60sp pulsed DCs are referred to as pDC(H)s. The inventor has also surprisingly discovered that the autologous pDC(H)s are therapeutically effective for treating a subject suffering from an autoimmune disease such as, for example, type 1 diabetes (T1D), multiple sclerosis (MS), psoriasis, rheumatoid arthritis, lupus, vitiligo, pemphigus or dermatomyositis, and improving biological indicators associated with T1D in the T1D patients up to one-two year/s after treatment. The inventor has further generated novel human HLA-A/B/C-deficient B cell lines having stable surface expression of a complex of HLA-E and the hHsp60sp (TH1) or a complex of HLA-E and B7sp (TB1), enabling a reliable potency assay for identifying a subject having defective HLA-E restricted CD8+ Treg cells that are correctable by the treatment of autologous pDC(H)s.

A composition comprising dendritic cells loaded with hHsp60sp is provided. The dendritic cells are from a subject in need of the dendritic cells loaded with hHsp60sp, and the dendritic cells loaded with hHsp60sp have been fixed with paraformaldehyde (PFA).

In the composition, the dendritic cells loaded with hHsp60sp may be in a therapeutically effective amount for correcting correctable defect of HLA-E restricted CD8+ Treg cells from a subject. The composition may be formulated for intravenous administration to the subject.

In the composition, the dendritic cells loaded with hHsp60sp may be in a therapeutically effective amount for treating an autoimmune disease in a subject. The composition may be formulated for intravenous administration to the subject.

The composition may further comprise a medium. The medium may comprise dimethyl sulfoxide (DMSO), human serum albumin (HSA) and PLASMA-LYTE® A.

The composition may further comprise greater than 80% total CD11c+ (gated on large cells).

The composition may further comprise a cryoprotectant.

According to the composition of the present invention, the subject may suffer from an autoimmune disease. The autoimmune disease may be selected from the group consisting of type 1 diabetes (T1D), multiple sclerosis (MS), psoriasis, rheumatoid arthritis, lupus, vitiligo, pemphigus and dermatomyositis. The autoimmune disease may be type 1 diabetes (T1D). The autoimmune disease may be multiple sclerosis (MS).

For each composition of the present invention, a method is provided for preparing the composition. The preparation method comprises (a) isolating mononuclear cells from a subject; (b) incubating the mononuclear cells in a culture for no more than six days to produce immature dendritic cells (DCs); (c) harvesting the immature DCs from the culture in step (b); (d) incubating the harvested DCs with hHsp60sp to produce hHsp60sp loaded dendritic cells (DCS); (e) fixing the hHsp60sp loaded DCs with paraformaldehyde (PFA) to produce fixed hHsp60sp loaded DCs; and (f) suspending the hHsp60sp loaded DCs in a medium, whereby the composition is prepared. The preparation method may further comprise freezing the composition.

According to the preparation method of the present invention, the hHsp60sp loaded DCs may be fixed with 2% PFA in step (d). The composition may comprise greater than 80% total CD11c+ (gated on large cells). The medium may comprise dimethyl sulfoxide (DMSO), human serum albumin (HSA) and PLASMA-LYTE® A. The composition may further comprise a pharmaceutically acceptable carrier. The composition may further comprise a cryoprotectant. The mononuclear cells may be cultured in the presence of GM-CSF and IL-4 in step (b).

According to the preparation method of the present invention, the composition may be formulated for intravenous administration to the subject. The subject may suffer from an autoimmune disease. The autoimmune disease may be selected from the group consisting of type 1 diabetes (T1D), multiple sclerosis (MS), psoriasis, rheumatoid arthritis, lupus, vitiligo, pemphigus and dermatomyositis. The auto-immune disease may be type 1 diabetes (T1D). The auto-immune disease may be multiple sclerosis (MS).

For each preparation method of the present invention, a composition prepared according to the method is provided.

A first recombinant human cell is provided. The first recombinant human cell comprises a heterologous gene encoding a first fusion protein and expresses the fusion protein on the surface of the first recombinant cell. The fusion protein may comprise human leukocyte antigen system E (HLA-E) and hHsp60sp. The recombinant cell may express the fusion protein permanently. The fusion protein may further comprise a linker between the HLA-E and the hHsp60sp.

A cell line having an ATCC accession number of PTA-127256 is provided.

A second recombinant human cell is provided. The second recombinant human cell comprises a heterologous gene encoding a fusion protein and expresses the fusion protein on the surface of the second recombinant human cell. The fusion protein comprises a human leukocyte antigen system E (HLA-E) and B7sp. The second recombinant human cell expresses the fusion protein permanently. The fusion protein further comprising a linker between the HLA-E and the B7sp.

A cell line having an ATCC accession number of PTA-127257 is provided.

A method is provided for determining a percentage of maximum inhibition of testing the function of the HLA-E restricted CD8+ Treg cells from a subject. The function determination method comprises (a) determining a percentage of maximum inhibition for specific target cells, wherein the specific target cells are cells expressing a complex of HLA-E and hHsp60sp on the surface of the specific target cells. Step (a) comprises (i) obtaining a specific target cell mixture having an equal number of the specific target cells and unloaded target cells, wherein the unloaded target cells are cells expressing HLA-E on the surface of the unloaded target cells; (ii) culturing the specific target cell mixture in the absence of the testing HLA-E CD8+ Treg cells; (iii) quantifying the ratio of the specific target cells over the unloaded target cells after being cultured in the absence of the testing HLA-E restricted CD8+ Treg cells to calculate a first control ratio as the ratio of the quantified proliferation of the specific target cells to the quantified proliferation of the unloaded target cells after being cultured in the absence of the testing HLA-E restricted CD8+ Treg cells; (iv) culturing the specific target cell mixture in the presence of the testing HLA-E restricted CD8+ Treg cells at graded ratios of the testing HLA-E restricted CD8+ Treg cells to the specific target cells (specific E/T ratios); (v) quantifying proliferation of the specific target cells and the unloaded target cells after being cultured in the presence of the testing HLA-E restricted CD8+ Treg cells to calculate a first experimental ratio as the ratio of the quantified proliferation of the specific target cells to the quantified proliferation of the unloaded target cells after being cultured in the presence of the testing HLA-E restricted CD8+ Treg cells at each of the graded specific E/T ratios; and (vi) calculating a percentage of specific inhibition for the specific target cells at each of the graded specific E/T ratios as (first control ratio−first experimental ratio)/first control ratio×100%, wherein the percentage of maximum inhibition for the specific target cells is the highest value of the percentages of specific inhibition for the specific target cells at the graded specific E/T ratios. The function determination method further comprises (b) determining a percentage of maximum inhibition for control target cells, wherein the control target cells are cells expressing the HLA-E and B7sp on the surface of the control target cells. Step (b) comprises (i) obtaining a control target cell mixture having an equal number of the unloaded target cells and the control target cells; (ii) culturing the control target cell mixture in the absence of the testing HLA-E CD8+ Treg cells; (iii) quantifying proliferation of the control target cells and the unloaded target cells after being cultured in the absence of the testing HLA-E restricted CD8+ Treg cells to calculate a second control ratio as the ratio of the quantified proliferation of the control target cells to the quantified proliferation of the unloaded target cells after being cultured in the absence of the testing HLA-E CD8+ Treg cells; (iv) culturing the control target cell mixture in the presence of the testing HLA-E restricted CD8+ Treg cells at graded ratios of the testing HLA-E restricted CD8+ Treg cells to the control target cells (control E/T ratios); (v) quantifying proliferation of the control target cells and the unloaded target cells after being cultured in the presence of the testing HLA-E restricted CD8+ Treg cells to calculate a second experimental ratio as the ratio of the quantified proliferation of the control target cells to the quantified proliferation of the unloaded target cells after being cultured in the presence of the testing HLA-E restricted CD8+ Treg cells at each of the graded specific E/T ratios; and (vi) calculating a percentage of specific inhibition for the control target cells at each of the graded control E/T ratios as (second control ratio−second experimental ratio)/second control ratio×100%, wherein the percentage of maximum inhibition for the control target cells is the highest value of the percentages of specific inhibition for the control target cells at the graded control E/T ratios. The function determination method further comprises (c) calculating the percentage of the maximum specific inhibition for the testing HLA-E restricted CD8+ Treg cells by subtracting the percentage of maximum inhibition for the control target cells from the percentage of maximum inhibition for the specific target cells.

According to the function determination method of the present invention, the specific target cells may be from the cell line having an ATCC accession number of PTA-127256 and the control target cells may be from the cell line having an ATCC accession number of PTA-127257. The subject may suffer from an autoimmune disease. The autoimmune disease may be selected from the group consisting of type 1 diabetes (T1D), multiple sclerosis (MS), psoriasis, rheumatoid arthritis, lupus, vitiligo and dermatomyositis. The subject may suffer from type 1 diabetes (T1D). The subject may suffer from multiple sclerosis (MS).

A method is provided for determining whether HLA-E restricted CD8+ Treg cells freshly isolated from a subject are defective. The defect determination method comprises determining a percentage of maximum inhibition for the freshly isolated HLA-E restricted CD8+ Treg cells according to the function determination method using the freshly isolated HLA-E restricted CD8+ Treg cells as the testing HLA-E CD8+ Treg cells. A percentage of maximum inhibition less than 50% of the freshly isolated HLA-E CD8+ Treg from a normal healthy people indicates that the freshly isolated HLA-E restricted CD8+ Treg cells are defective and the subject has defective HLA-E CD8+ Treg cells.

According to the defect determination method of the present invention, the specific target cells may be from the cell line having an ATCC accession number of PTA-127256 and the control target cells may be from the cell line having an ATCC accession number of PTA-127257. The subject may suffer from an autoimmune disease. The autoimmune disease may be selected from the group consisting of type 1 diabetes (T1D), multiple sclerosis (MS), psoriasis, rheumatoid arthritis, lupus, vitiligo and dermatomyositis. The subject may suffer from type 1 diabetes (T1D). The subject may suffer from multiple sclerosis (MS).

A method is provided for determining whether defective HLA-E restricted CD8+ Treg cells from a subject are correctable. The correctableness determination method comprises (a) activating the defective HLA-E restricted CD8+ Treg cells with autologous dendritic cells loaded with hHsp60sp to produce CD8(H) cells; (b) determining a percentage of maximum inhibition for the CD8(H) cells according to the function determination method using the CD8(H) cells as the testing HLA-E CD8+ Treg cells; (c) activating the defective HLA-E restricted CD8+ Treg cells with fixed autologous dendritic cells loaded with B7sp to produce CD8(B) cells; (d) determining a percentage of maximum inhibition for the CD8(B) cells according to the function determination method using the CD8(B) cells as the testing HLA-E CD8+ Treg cells; and (e) calculating a normalized percentage of maximum inhibition for the defective HLA-E restricted CD8+ Treg cells by subtracting the percentage of maximum inhibition for the CD8(B) cells from the percentage of maximum inhibition for the CD8(H) cells. A normalized percentage of maximum inhibition greater than 50% of the HLA-E restricted CD8+ Treg cells from normal healthy control people indicates that the defective HLA-E restricted CD8+ Treg cells are correctable and the subject has correctable defective HLA-E CD8+ Treg cells.

According to the correctableness determination method of the present invention, the specific target cells may be from the cell line having an ATCC accession number of PTA-127256 and the control target cells may be from the cell line having an ATCC accession number of PTA-127257. The defective HLA-E restricted CD8+ Treg cells from the subject may be determined according to the defect determination method. The subject may suffer from an autoimmune disease. The autoimmune disease may be selected from the group consisting of type 1 diabetes (T1D), multiple sclerosis (MS), psoriasis, rheumatoid arthritis, lupus, vitiligo and dermatomyositis. The subject may suffer from type 1 diabetes (T1D). The subject may suffer from multiple sclerosis (MS).

A method is provided for correcting defective HLA-E restricted CD8+ Treg cells in a subject in need thereof, wherein the defective HLA-E restricted CD8+ Treg cells are correctable. The correction method comprises administering to the subject a therapeutically effective amount of a therapeutic composition. The therapeutic composition comprises fixed autologous dendritic cells loaded with the hHsp60sp in a medium. The dendritic cells loaded with hHsp60sp have been fixed with paraformaldehyde (PFA).

According to the correction method of the present invention, the medium may comprise dimethyl sulfoxide (DMSO), human serum albumin (HSA) and PLASMA-LYTE® A. The therapeutic composition may further comprise greater than 80% total CD11c+ (gated on large cells). The therapeutic composition may further comprise a cryoprotectant. The therapeutic composition may be administered to the subject intravenously. The subject may suffer from an autoimmune disease. The autoimmune disease may be selected from the group consisting of type 1 diabetes (T1D), multiple sclerosis (MS), psoriasis, rheumatoid arthritis, lupus, vitiligo and dermatomyositis. The subject may suffer from type 1 diabetes (T1D). The subject may suffer from multiple sclerosis (MS).

A method is provided for treating type 1 diabetes (T1D) in a subject in need thereof. The T1D treatment method comprises administering to the subject a therapeutically effective amount of a therapeutic composition. The therapeutic composition comprises autologous dendritic cells loaded with hHsp60sp in a medium. The dendritic cells loaded with hHsp60sp have been fixed with paraformaldehyde (PFA).

According to the T1D treatment method of the present invention, the medium may comprise dimethyl sulfoxide (DMSO), human serum albumin (HSA) and PLASMA-LYTE® A. The therapeutic composition may further comprise greater than 80% total CD11c+ (gated on large cells). The therapeutic composition may further comprise a cryoprotectant. The therapeutic composition may be administered to the subject intravenously.

According to the T1D treatment method of the present invention, the subject may be diagnosed with T1D not more than three months prior to the treatment. The subject may be diagnosed with T1D not more than 12 months prior to the treatment. The subject may be a minor. The subject may have correctable defective HLA-E restricted CD8+ Treg cells.

A method is provided for treating multiple sclerosis (MS) in a subject in need thereof. The MS treatment method comprises administering to the subject a therapeutically effective amount of a therapeutic composition. The therapeutic composition comprises autologous dendritic cells loaded with hHsp60sp in a medium. The dendritic cells loaded with hHsp60sp have been fixed with paraformaldehyde (PFA).

According to the MS treatment method of the present invention, the medium may comprise dimethyl sulfoxide (DMSO), human serum albumin (HSA) and PLASMA-LYTE® A. The therapeutic composition may further comprise greater than 80% total CD11c+ (gated on large cells). The therapeutic composition may further comprise a cryoprotectant. The therapeutic composition may be administered to the subject intravenously. The subject may have correctable defective HLA-E restricted CD8+ Treg cells.

DETAILED DESCRIPTION OF THE INVENTION

Figure 1A:
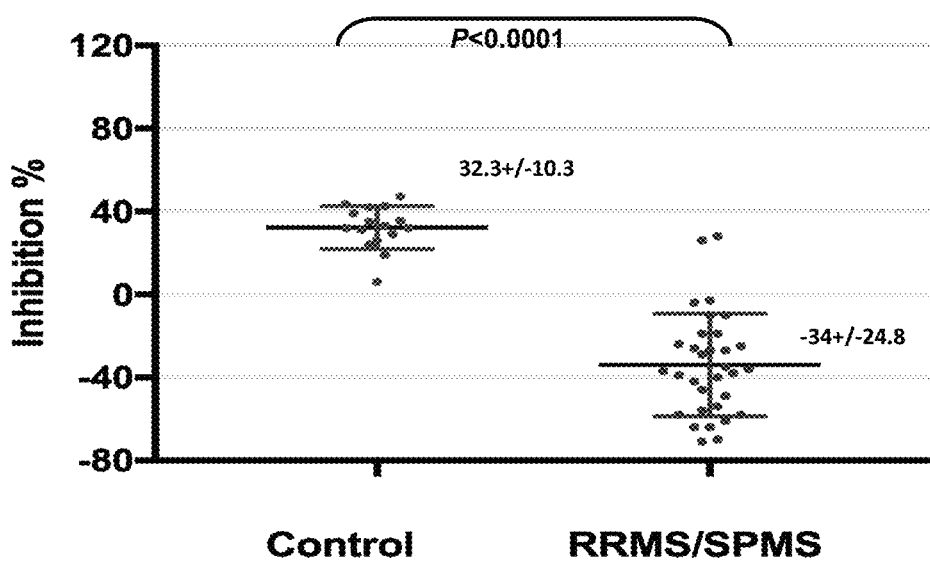
FIGS. 1A-1C show results from a CD8+ Treg cell specificity assay as set forth in Example 8. The CD8+ Treg cells from most of clinically diagnosed multiple sclerosis (MS) patients, whom were randomly tested, both RRMS (relapsing-remitting multiple sclerosis) and SPMS (secondary-progressive multiple sclerosis), were functionally defective when compared with the normal functional CD8+ Treg cells from healthy individuals prior to treatment with the therapeutic agent of the present invention, whereas the function of the defective CD8+ Treg cells from the majority of the MS patients tested was corrected or restored after the treatment. A. BEFORE therapy, the readings between "normal" (N=16) and "RRMS/SPMS patients" (N=32) are statistically significant, P<0.0001. B. The "control" group showed normal pathway function BEFORE therapy (N=16), and statistically non-distinguishable AFTER therapy (N=12), P=0.1392. C. The "patient" group (N=32) showed defective pathway function BEFORE therapy, and corrected defect AFTER therapy, showing statistically significant on the effect of the treatment, P<0.0001.

The invention relates to dendritic cells (DCs) prepared from a subject, loaded with human heat shock protein 60 signal peptide (hHsp60sp), and fixed to stabilize the binding between the HLA-E molecules on DCs and the hHsp60sp. The resulting DCs are referred to pDC(H)s. The invention also provides an assay and novel cells lines to determine whether a subject has defective HLA-E restricted CD8+ Treg cells and to determine whether the defective HLA-E restricted CD8+ Treg cells from a subject are correctable by treatment with autologous pDC(H)s ex vivo. The invention further relates to the use of autologous pDC(H)s to correct defective HLA-E restricted CD8+ Treg cells in the subject in vivo to treat an autoimmune disease in the subject.

This invention is based on the discovery by the inventor that fixation of the hHsp60sp loaded DCs with 2% paraformaldehyde (PFA) stabilizes the association between the binding of HLA-E on DCs and the hHsp60sp and improves stability of the pDC(H)s from preparation to administration, while the pDC(H)s remain therapeutically effective. The fixation of the pDC(H)s makes it feasible for preparation of the autologous pDC(H)s from a subject, screening for a patient having defective HLA-E restricted CD8+ Treg cells that are correctable by the autologous pDC(H)s, correcting defective HLA-E restricted CD8+ Treg cells in a subject, and treating a patient suffering from an autoimmune disease.

The invention is also based on the development of two novel cells lines. These novel cell lines make the potency assay more reliable and efficient to identify a subject having defective HLA-E restricted CD8+ Treg cells that are correctable by the autologous pDC(H)s. The two novel cell lines are human HLA-A/B/C-deficient B lymphoma cell lines having stable surface expression of a complex of HLA-E and the hHsp60sp (TH1) or human HLA-A/B/C-deficient lymphoma B cell lines having stable surface expression of a complex of HLA-E and a control peptide, for example, B7sp (TB1). These cell lines are critical to the consistency and stability of the potency assay.

The invention is further based on the discovery by the inventor that treatment of patients suffering from type 1 diabetes (T1D) with autologous pDC(H)s resulted in restoration of the CD8 Treg function, stop or delay of the decline of C-peptide AUC, maintaining Hb A1c within a normal range, and reducing daily insulin intake up to one year after the treatment. Moreover, the inventor has successfully corrected defective HLA-E restricted CD8+ Treg cells from patients suffering from multiple sclerosis, psoriasis, rheumatoid arthritis, lupus, vitiligo, pemphigus or dermatomyositis. The correction was performed ex-vivo with autologous pDC(H)s.

Unlike existing small molecule or cell-based therapies, the present invention provides for a new type of cell-based therapeutic approach to treat and/or prevent T1D and other autoimmune diseases in patients. The therapeutic agent in the present invention, used as a vaccine, may treat the patients by re-activating and correcting the defective regulatory pathway mediated by HLA-E restricted CD8+ Treg cells, which under normal circumstances act to selectively control the pathogenic self-reactive T cells that destroy B cells without damaging the ongoing normal immune responses to their anti-infection and anti-tumor immunity, a process called self-nonself discrimination.

All terms used in the present application have the plain and ordinary meanings and unless defined otherwise.

TABLE 2

| List of Abbreviations | |
| --- | --- |
| AABB | American Association of Blood Banks |
| APC | Antigen Presenting Cells |
| ATG | Anti-thymocyte Globulin |
| B721 | A Human HLA-A/B/C-deficient B cell line |
| B721/E | B721 cell line transfected with HLA-E gene |
| B7sp | Human eguivalent peptide of Qdm; VMAPRTVLL (SEQ ID NO: 2) |
| CD11C+ | Integrin alpha X chain protein, which is found at a high level on human DCs |
| CD3+ | Cluster of Differentiation 3 positive T cells; T cell co-receptor |
| CD4 | Cluster of differentiation 4 |
| CD8 | Cluster of differentiation 8 |
| CD8(B) | CD8+ T cells stimulated with autologous immature dendritic cells loaded with B7sp |
| CD8(H) | CD8+ T cells stimulated with autologous immature dendritic cells loaded with hHsp60sp |
| CD8(N) | CD8+ T cells stimulated with autologous immature dendritic cells not loaded with peptide |
| CD8+ T cells | Cluster of Differentiation 8 positive T cells; cytotoxic T cells |
| CD86+ T cells | Cluster of Differentiation 86 positive T cells |
| CFSE | Carboxyfluorescein succinimidyl ester |
| CTCAE | Common Terminology Criteria for Adverse Events |
| CTL | Cytotoxic T Cell |
| D0 | Day 0 |
| D5 | Day 5 |
| D6 | Day 6 |
| D11 | Day 11 |
| DC | Dendritic cell |
| DLT | Dose limiting toxicity |
| DMK | Dystrophia myotonica kinase |
| DMSO | Dimethyl sulfoxide |
| DSMB | Data Safety Monitoring Board |
| FACS | Fluorescence-activated cell sorting |
| FBS | Fetal bovine serum |
| GAD | Glutamic acid decarboxylase |
| GCP | Good clinical practice |
| GFAP | Glial fibrillary acidic protein |
| GM-CSF | Granulocyte-macrophage colony-stimulating factor |
| HbA1c | Hemoglobin A1c |
| HBsAg | Hepatitis B virus surface antigen |
| HBV | Hepatitis B virus |
| HCV | Hepatitis C Virus |
| HIV | Human immunodeficiency virus |
| HLA | Human leukocyte antigen |
| HLA-E | Human leukocyte antigen (HLA) system E; HLA class I histocompatibility antigen, alpha chain E (HLA-E); MHC class 1 antigen E |
| HSA | Human serum albumin |

TABLE 2-continued

List of Abbreviations

| | |
|---|---|
| hHsp60sp | Human heat Shock Protein 60 Signal Peptide consisting of QMRPVSRVL (SEQ ID NO: 1) |
| HTLV-1/2 | Human T-lymphotropic virus type 1/2 |
| i.v. | Intravenous |
| ICA | Islet Cell Antibody |
| iDC | Immature dendritic cell |
| IFNy | Interferon y |
| IGRP | Islet-specific glucose-6-phosphate catalytic subunit related protein |
| IL | Interleukin |
| IL-2 | Interleukin 2 |
| IL-4 | Interleukin 4 |
| LAL | Limulus amebocyte lysate |
| LN2 | Liquid nitrogen |
| mcg | Micrograms |
| MHC | Major histocompatibility complex |
| MMRM | Mixed model for repeated measures |
| MMTT | Mixed meal tolerance test |
| MRI | Magnetic resonance image |
| mRNA | Messenger ribonucleic acid |
| NOD | Non-obese diabetic (murine model) |
| PBMC | Peripheral blood mononuclear cells |
| PBS | Phosphate buffered saline |
| pDC | ; fixed peptide loaded dendritic cell; fixed peptide pulsed dendritic cell |
| pDC(H) | Fixed hHsp60sp loaded dendritic cell; Fixed hHsp60sp pulsed dendritic cell |
| pDC(B) | Fixed B7sp loaded dendritic cell; Fixed B7sp pulsed dendritic cell |
| PFA | Paraformaldehyde |
| ppIAPP | Pre-pre-islet amyloid polypeptide protein |
| Qa-1 | Murine MHC class 1 molecule |
| RA | Rheumatoid arthritis |
| RNA | ribonucleic acid |
| RPMI | Roswell Park Memorial Institute medium |
| RRMS | Relapsing-remitting multiple sclerosis |
| S.C. | Subcutaneous |
| SLE | Systemic lupus erythematosus |
| SPMA | Secondary-progressive multiple sclerosis |
| T1D | Type 1 diabetes |
| TB | T cell line having surface expression of an HLA-E/B7sp complex |
| TH | T cell line having surface expression of an HLA-E/Hsp60sp complex |
| TNC | Total nucleated cells |
| TNFα | Tumor necrosis factor α |
| Treg cells | Regulatory T cells |
| USP | United States Pharmacopeia |

(1). The term "type A peptide" used herein refers to a HLA-E binding peptide Qdm (in mice) and B7sp (in humans), or Qdm/B7sp like peptide that can interact with CD94/NKG2A when bound to HLA-E and inhibit the function of natural killer (NK) cells.

(2). The term "type B peptide" used herein refers to a HLA-E binding peptide having a common structure of x-Met/Leu-x-x-x-x-x-leu/Ile (x represents any amino acid) (SEQ ID NO: 3) that (i) does not inhibit NK cells when bound to HLA-E; (ii) is recognized by HLA-E restricted CD8+ Treg cells when bound to HLA-E; (iii) can compete with type A HLA-E binding peptides such as Qdm or B7sp for binding to HLA-E; and (vi) inhibit the target cells that expressing the "complex" of HLA-E coupled with such peptide(s). Hsp60sp and hHsp60sp are type B peptides.

(3). The term "Qdm" used herein refers to an MHC class Ia leader-sequence derived peptide that binds HLA-E under physiological conditions and consists of the amino acid sequence AMAPRTLLL (SEQ ID NO: 4)

(4). The term "human heat shock protein 60 signal peptide (hHsp60sp)" as used herein refers to the peptide consisting of QMRPVSRVL (SEQ ID NO: 1) Please double check the sequence.

(5). The term "B7sp" used herein refers to the peptide consisting of the amino acid sequence VMAPRTVLL (SEQ ID NO: 2) Please double check the sequence.

(6). The term "dendritic cells (DCs)" used herein refers to a type of human antigen-presenting cells (also known as accessory cells) that process an antigen and present the processed peptide(s) by MHC/HLA molecules on the cell surface to T cells of the immune system to activate the T cells. DCs play an important role in connecting the innate and the adaptive immune systems. No single cell marker has been found to be expressed exclusively on DCs. A combination of the presence and absence of various cell markers are used to identify the DCs. Markers for DCs include BDCA-1, CD8, CD8alpha, CD11b, CD11c, CD103, CD205 and MHC Class Ia and/or MHC class Ib molecules, including HLA-E, and MHC Class I.

(7). The term "Biomarker" used herein refers to Type B peptide/s coupled with HLA-E molecules preferentially expressed on all self-reactive T cells that are specifically recognized by the T cell receptor (TCR) on Q/E CD8+ Treg cells.

(8). The term "immature dendritic cells (IDCs)" used herein refers to dendritic cells obtained from a culture of mononuclear cells for no more than 6 days, which mononuclear cells are isolated from a subject. Markers for iDCs include, CD11c.

(9). The term "pDC(H)" used herein refers to a dendritic cell (DC) loaded with hHsp60sp, for example, ex vivo, and fixed with, for example, paraformaldehyde.

(10). The terms "fixation" and "fixing" as used herein refer to a chemical process to stabilize or preserving cells and their subcellular components as close as possible to their original status. One suitable fixative is paraformaldehyde (PFA), for example, 2% PFA.

(11). The terms "peptide pulsing" and "peptide loading" are used herein interchangeably and refer to treating cells in vitro with a peptide (e.g., hHsp60sp and B7sp) to form a complex of the peptide and a molecule (e.g., HLA-E) expressed on the cell surface. The resulting cells are referred to as peptide pulsed or loaded cells. Where the cells are DCs, this process is also referred to as "DC pulsing" and the resulting cells are referred to as peptide pulsed DCs or loaded DCs. Where the peptide is a HLA-E binding peptide hHsp60sp, and the cells are DCs, the resulting cells are hHsp60sp pulsed DCs.

(12). The term "subject" used herein refers to a human individual. The subject may suffer from an autoimmune disease. The subject may have HLA-E restricted CD8+ Treg cells capable of specifically recognizing HLA-E/hHsp60sp complex expressed on target cells, and/or down-regulating self-reactive T cells by specifically recognizing HLA-E/hHsp60sp complex expressed on target cells. The subject may have defective Q/E CD8+ Treg cells. The subject may have defective HLA-E restricted CD8+ Treg cells that are correctable by treating the defective HLA-E restricted CD8+ Treg cells with autologous pDC(H)s. The subject may have correctable defective HLA-E restricted CD8+ Treg cells capable of selectively suppressing self-reactive T cells when triggered ex-vivo, or inoculated into the subjects in vivo with pDC(H)s.

(13). The term "autoimmune disease" used herein refers to a symptom or pathological condition in a subject, whose immune system attacks the subject's own cells, tissues or organs. Examples of autoimmune diseases include alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Behcet's disease, bullous pemphigoid, cardiomyopathy, celiac sprue-dermatitis, chronic fatigue syndrome immune, deficiency syndrome (CFIDS), chronic inflammatory demyelinating polyneuropathy, cicatricial pemphigoid, cold agglutinin disease, crest syndrome, Crohn's disease, Dego's disease, dermatomyositis, dermatomyositis-juvenile, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), IGA nephropathy, juvenile arthritis, Meniere's disease, mixed connective tissue disease, multiple sclerosis (MS), myasthenia gravis, pemphigus vulgaris, pernicious anemia, ply arteritis nodosa, polychondritis, polyglandular syndromes, polymyalgia rheumatic, polymyositis and dermatomyositis, psoriasis, Raynaud's phenomenon, Reiter's syndrome, rheumatic fever, rheumatoid arthritis, scleroderma, scleroderma, Sjogren's syndrome, stiff-man syndrome, systemic lupus erythematosus (SLE), Takayasu arteritis, temporal arteritis/giant cell arteritis, type 1 diabetes (T1D), ulcerative colitis, uveitis, vasculitis, vitiligo and Wegener's granulomatosis. The autoimmune disease may be selected from the group consisting of type 1 diabetes (T1D), multiple sclerosis (MS), psoriasis, rheumatoid arthritis, lupus, vitiligo, pemphigus and dermatomyositis. In one embodiment, the autoimmune disease is type 1 diabetes (T1D). In another embodiment, the autoimmune disease is multiple sclerosis (MS).

(14). The term "autologous" used herein refers to the source of a sample of, for example, cells, obtained or derived from a subject to whom the sample is administered. The autologous sample may be modified ex vivo before being administered to the subject. Certain desirable cells (e.g., mononuclear cells) may be collected from blood of a subject, and cultured to obtain dendritic cells (DCs), including immature dendritic cells (iDC), which may be harvested and loaded with a desirable peptide, for example, hHsp60sp or a control peptide (e.g., B7sp). The autologous cells may be administered to the subject from whom the autologous cells are obtained or derived.

(15). The terms "specifically recognize" used herein refers to specific recognition of a complex on the cell surface comprised of HLA-E molecule on a cell associated with a desirable peptide (e.g., hHsp60sp), but not any peptide that is not the desirable peptide, for example, a control peptide (e.g., B7sp). The specific association may be direct or indirect.

(16). The term "HLA-E" used herein refers to human leukocyte antigen (HLA) system E, also known as HLA class Ib histocompatibility antigen, alpha chain E (HLA-E), or MHC class Ib antigen E. The HLA-E is a protein encoded by the HLA-E gene in humans. The amino acid sequences of HLA-E may be found in NCBI accession nos. CAA05527, CAA40172, BAB63328, and BAF31260.

(17). The terms "HLA-E-restricted CD8+ regulatory T cells", "HLA-E-restricted CD8+ Treg cells", "HLA-E-restricted CD8+ T cells", "HLA-E restricted CD8+ T cells", "HLA-E restricted regulatory CD8+ T cells" or "Q/E CD8+ Treg cells" used herein refer to CD8+ T cells that specifically recognize a type B peptide (e.g., hHsp60sp) presented by a HLA-E molecule on the surface of target cells. Upon the specific recognition, the HLA-E restricted CD8+ Treg cells may specifically suppress, inhibit or down regulate self-reactive T cells in the subject.

The term "defective HLA-E restricted CD8+ Treg cells" used herein refers to HLA-E restricted CD8+ Treg cells incapable of specifically recognizing a complex of HLA-E associated with hHsp60sp (HLA-E/hHsp60sp complex). Defective HLA-E restricted CD8+ Treg cells in a subject are incapable of selectively suppressing self-reactive T cells in the subject. Whether HLA-E restricted CD8+ Treg cells are defective may be determined according to the present invention, for example, using a CD8+ T cell specificity assay. HLA-E restricted CD8+ Treg cells having a percentage of maximum inhibition less than 50% of HLA-E restricted CD8+ Treg cells from a normal healthy control people may be deemed defective. In one embodiment, HLA-E restricted CD8+ Treg cells having a percentage of maximum inhibition less than 50% of HLA-E restricted CD8+ Treg cells from a normal healthy control people are deemed as defective. The term "correctable defective HLA-E restricted CD8+ Treg cells" used herein refers to defective HLA-E restricted CD8+ Treg cells from a subject, which defective HLA-E restricted CD8+ Treg cells became capable of specifically recognizing a complex of HLA-E associated with hHsp60sp (HLA-E/hHsp60sp complex) after being treated ex vivo with fixed dendritic cells loaded with the hHsp60sp [pDC (H)s], which dendritic cells are from the same subject. Corrected defective HLA-E restricted CD8+ Treg cells may be administered to the subject. Corrected defective HLA-E restricted CD8+ Treg cells administered to the subject may selectively suppress self-reactive T cells in the subject. Whether defective HLA-E restricted CD8+ Treg cells are correctable may be determined according to the present invention, for example, using a CD8+ T cell specificity assay. Defective HLA-E restricted CD8+ Treg cells having a normalized percentage of maximum inhibition greater than 50% of HLA-E restricted CD8+ Treg cells from a normal healthy control people may be deemed as correctable. In one embodiment, defective HLA-E restricted CD8+ Treg cells having a normalized percentage of maximum inhibition greater than 50% of HLA-E restricted CD8+ Treg cells from a normal healthy control people are deemed correctable.

(18). The term "target cells" used herein refers to any cells, including artificially made cells having surface expression of HLA-E/Type B peptide complex (for example, hHsp60sp), which are made for performing the "HLA-E restricted CD8+ Treg specificity assay" to detect the function of the Q/E CD8+ Treg cells.

(19). The term "unloaded target cells" used herein refers to target cells having surface expression of HLA-E not loaded with a peptide. For example, the unloaded target cells may be HLA-E transfected B721 cells (B721/E).

(20). The term "loaded target cells" used herein refers to target cells having surface expression of HLA-E loaded with a peptide. Examples of loaded target cells include B721/E cells loaded with hHsp60sp (specific target cells) or B7sp (control target cells).

(21). The terms "specific target cells", "H cells", or "TH1 cells" used herein interchangeably and refers to T cells having surface expression of HLA-E/hHsp60sp complex. The HLA-E and the hHsp60sp form an HLA-E/hHsp60sp complex on the surface of the specific target cells, which may be cells (e.g., B721) transfected with a gene encoding the HLA-E or a fusion protein of the HLA-E and the hHsp60sp. The HLA-E or the fusion protein may be expressed transiently or permanently. In one embodiment, the specific target cell is of a cell line expressing the fusion protein of the HLA-E and the hHsp60sp on the cell surface (ATCC Accession No. PTA-127256).

(22). The terms "control target cells", "B cells", or "TB1 cells" used herein interchangeably and refers to T cells having surface expression of HLA-E that have been pulsed or loaded with a control peptide (e.g., B7sp). The HLA-E and the control peptide (e.g., B7sp) form an HLA-E/control peptide complex. The control target cells may be cells transfected with a gene encoding the HLA-E or a fusion protein of the HLA-E and the control peptide (e.g., B7sp). The HLA-E or the fusion protein may be expressed transiently or permanently. In one embodiment, the control target cell is of a cell line expressing the fusion protein of the HLA-E and the B7sp on the cell surface (ATCC Accession No. PTA-127257).

When used in the same assay or method, the specific target cells, control target cells and unloaded target cells may be derived from the same parental cells, for example, B721 cells, a Human B cell lymphoma cell line.

(23). The term "graded ratios" used herein refers to a series of ratios between two components in a mixture designed for changing the characteristics of the mixture.

(24). The term "freshly isolated" used herein refers to mononuclear cells that have not been cultured and triggered with pDC after being isolated from a subject.

(25). The terms "activation" or "activating" used herein refer to stimulation of or stimulating CD8+ regulatory T cells by fixed autologous DCs loaded with a peptide. The CD8+ regulatory T cells are HLA-E-restricted. The HLA-E-restricted CD8+ Treg cells may be defective. The autologous DCs loaded with a peptide may have been purified. The peptide may be hHsp60sp or a control peptide (e.g., B7sp). CD8+ T cells activated by fixed hHsp60sp loaded autologous DCs [pDC(H)s] are referred to as CD8(H). CD8+ T cells activated by autologous DCs loaded with B7sp are referred to as CD8(B).

(26). The terms "HLA-E-restricted regulatory CD8+ T cell function", "HLA-E-restricted CD8+ T cell function", "CD8 Treg function" or "CD8+ T cell function" used herein refers to the ability of the HLA-E-restricted regulatory CD8+ T cells, HLA-E-restricted CD8+ T cells, CD8 Treg or CD8+ T cells, which are capable of specifically recognizing HLA-E/hHsp60sp complex, to specifically inhibit, suppress or down-regulate proliferation of target cells. Failure to do that indicates that the HLA-E-restricted regulatory CD8+ T cells, HLA-E-restricted CD8+ T cells, CD8 Treg or CD8+ T cells are defective. This defect may be correctable.

(27). The terms "CD8+ T cell specificity assay", "potency test", "potency assay" or "CD8+ T cell inhibition assay" used herein refers to an in vitro test to determine the inhibition effect of testing CD8+ T cells, which are capable of specifically recognizing HLA-E/hHsp60sp complex, on the surface of target cells. The target cells are incubated in the presence of testing CD8+ T cells, acting as effector cells (E), at graded E/T ratios (experimental cultures) or in the absence of testing CD8+ T cells (control cultures). The target cells may be a cell mixture of an equal number of target cells (e.g., specific target cells expressing an HLA-E/hHsp60sp complex or control target cells expressing an HLA-E/hB7sp complex) and internal system control target cells (parental B721 cells). The ratio of number of the cultured specific target cells vs the number of an internal system control target cells (B721) in the absence of testing CD8+ T cells or in the presence of testing CD8+ T cells at each of the graded E/T ratios is quantified as a control ratio or an experimental ratio, respectively, and used to calculate a percentage of specific inhibition (potency) for the specific target cells or control target cells vs internal system control cells, at each graded E/T ratio.

(28). The term "percentage of specific inhibition (potency)" used herein refers to an inhibition measurement for testing CD8+ T cells on either specific target cells or on control target cells in the presence of the gradient number of the testing CD8+ T cells as compared with that on either specific or control target cells in the absence of testing CD8+ T cells as follows:

specific inhibition(%)=(control ratio−experimental ratio)/control ratio×100%.

The control ratio is the ratio of the quantified proliferation of the mixture of specific target cells or control target cells mixed with internal system control cells (B721) in the absence of the testing CD8+ T cells (well 1). The experimental ratio is the ratio of the quantified proliferation of the specific target cells or control target cells mixed with the internal system control cells (B721) in the presence of the testing CD8+ T cells at a gradient E/T ratio. The percentage of specific inhibition for the testing CD8 T cells on the target cells may vary depending on the E/T ratio, and may be used to generate an inhibition curve and identify the percentage of the maximum inhibition (Inhibition Index) for the loaded target cells or artificially made transfectants.

(29). The term "inhibition curve" used herein refers to a curve generated by the percentages of specific inhibition for each testing CD8+ T cells on each target cells at various E/T ratios. Where the target cells are specific target cells such as B721/E loaded with Type B peptide such as hHsp60sp peptide, the inhibition curve is a specific inhibition curve and the highest value on the specific inhibition curve is the percentage of the maximum inhibition for the specific target cells. Where the target cells are control target cells, such as B721/E loaded with Type A peptide, the inhibition curve is a control inhibition curve and the highest value on the control inhibition curve is the percentage of the maximum inhibition for the control target cells. The percentage of the maximum inhibition for the specific target cells and the percentage of the maximum inhibition for the control target cells may be used to calculate an "inhibition index" for testing CD8+ T cells.

(30). The terms "inhibition index", used herein refer to an inhibition measurement for testing CD8+ T cells on specific target cells as compared with control target cells, and equals to the percentage of the maximum inhibition for the specific target cells (i.e., highest value of the specific inhibition curve) subtracted by the percentage of the maximum inhibition for the control target cells (i.e., the highest value of the control inhibition curve).

(31). The term "D0-assay" used herein refers to an inhibition measurement for testing CD8+ T cells on specific target cells as compared with control target cells before activation by autologous pDC(H)s. The D0-assay is to detect the function of the HLA-E restricted regulatory CD8+ T cells without any treatment with pDC(H)s, such as freshly isolated CD8+ T cells from the subjects.

(32). The term "D11-assay" used herein refers to an inhibition measurement for defective CD8+ T cells on specific target cells after being triggered by fixed autologous DCs loaded with hHsp60sp [CD8(H) cells)] as compared with control target cells after being triggered by fixed autologous DCs loaded with a control peptide B7sp [CD8(B) cells]. The "Inhibition Index" equals to a percentage of maximum inhibition for the defective CD8+ T cells after being triggered by the fixed autologous DCs loaded with hHsp60sp subtracted by a percentage of maximum inhibition for the defective CD8+ T cells after being triggered by the autologous DCs loaded with the control peptide B7sp. The D11-assay is to detect the function of the dysfunctional HLA-E restricted regulatory CD8+ T cells after any treatment(s) with pDC(H)s to judge if the dysfunction of the CD8+ Treg cells tested is correctable.

(33). The term "therapeutic agent", "therapeutic composition" or "therapeutic preparation" used herein refers to a chemical entity, composition, formulation, preparation, complex, compound or molecule that exhibits one or more desirable therapeutic properties. The therapeutic agent of the present invention is autologous dendritic cells loaded with hHsp60sp [pDC(H)s].

(34). The term "therapeutically effective amount" used herein refers to an amount of a therapeutic agent effective for achieving a targeted goal, for example, slowing, halting or reversing the progression of a disease in a subject. The therapeutically effective amount may be an amount required for ameliorating or lessening a symptom, or altering or improving a biological indicator associated with the disease, for example, function of the HLA-E restricted CD8+ Treg, or the efficacy of the subject with autoimmune diseases by the treatment with pDC(H)s. The therapeutically effective amount may depend on nature of the targeted goal (e.g., correcting defective HLA-E restricted CD8+ regulatory T cells, treating an autoimmune disease, treating a type 1 diabetes, or treating multiple sclerosis), the nature of the therapeutic agent, the nature of the therapeutic composition, the subject, and the administration route. The therapeutically effective amount may be determined by a physician.

(35). The term "pharmaceutically acceptable carrier" used herein refers to a pharmaceutically acceptable material, composition or vehicle, for example, a liquid or solid filler, diluent, excipient, solvent or encapsulating material depending on the route of administration.

(36). The term "administration" or "administering" used herein refers to delivery of, for example, a therapeutic composition of the present invention, to a subject via any route, for example, via an intravenous, oral, nasal, transmucosal, transdermal, intramuscular and subcutaneous route. In one embodiment, the delivery is carried out by intravenous infusion.

(37). The term "cryoprotectant" used herein refers to a substance that prevents or minimizes damage to cells during a freezing process. The cryoprotectant may be selected from the group consisting of glycerol, propylene glycol, dimethyl sulfoxide (DMSO), and a combination thereof.

(38). The term "immunophenotyping" used herein refers to a process that uses antibodies and/or any other methods to identify certain type of cells based on one or more unique or specific types of the cell surface or intracellular antigens or markers.

(39). The terms "sterile" or "sterility" used herein refers to no detectable growth of potentially infectious agents such as bacteria and/or fungi in a testing sample for a predetermined period of time, for example, at least 14 days in a sterility test. The sterility test may be a commercially available sterility test.

(40). The term "pDC(B)" used herein refers to a dendritic cell (DC) loaded with B7sp, for example, ex vivo, and fixed with, for example, paraformaldehyde.

First, the present invention provides a composition comprising dendritic cells loaded with hHsp60sp. The dendritic cells are from a subject in need of the dendritic cells loaded with hHsp60sp, and the dendritic cells loaded with hHsp60sp have been fixed with paraformaldehyde (PFA). The fixed dendritic cells loaded with hHsp60sp are also referred to as pDC(H)s. The pDC(H)s may be in a therapeutically effective amount for correcting correctable defect of HLA-E restricted CD8+ Treg cells from a subject, for treating an autoimmune disease in a subject.

In one embodiment, the composition is a therapeutic composition for correcting defective HLA-E restricted CD8+ Treg cells in vivo from a subject. The defective HLA-E restricted CD8+ Treg cells regain the capacity of selective suppression of self-reactive T cell pool leading to the amelioration of the autoimmune disease of the subject after triggered (ex-vivo) or treated (in vivo) by the pDC(H)s. The therapeutic composition comprises a therapeutically effective amount of autologous dendritic cells loaded with the hHsp60sp [pDC(H)s] in a medium. The pDC(H)s have been fixed.

The hHsp60sp is the human heat shock protein 60 signal peptide consisting of the amino acid sequence of QMRPVSRVL (SEQ ID NO: 1). The hHsp60sp may be in the form of sterile white powder, and may be reconstituted with ddH$_2$O to obtain, for example, a final concentration of 1-3 mM (e.g., 2 mM) as stock solution.

In the therapeutic composition, the fixed hHsp60sp loaded autologous dendritic cells [pDC(H)s)] is the therapeutic agent. The autologous pDC(H)s are obtained from a subject from whom the defective HLA-E restricted CD8+ Treg cells are obtained. The autologous DCs may be isolated from the same subject or derived from cells isolated from the subject. The autologous DCs may be DCs harvested from a culture of mononuclear cells from the subject for a predetermined period of time, for example, 3, 4, 5, 6, 7 or 8 days. Where the autologous DCs harvested from a culture of mononuclear cells from the subject for no more than 6 days, the harvested DCs are immature DCs (iDCs).

The autologous DCs loaded with the hHsp60sp [pDC(H)s] are autologous DCs pulsed with the hHsp60sp forming a complex between the hHsp60sp and HLA-E expressed on the surface of the autologous DCs. Stable structure of the complex between the association of hHsp60sp and HLA-E molecules on the autologous DCs is critical to the stability and therapeutic effect of the pDC(H)s.

To improve stability of the pDC(H)s, the pDC(H)s have been fixed to stabilize the structure of the complex of HLA-E/hHsp60sp on the cell surface. The pDC(H)s may be fixed by a fixative that causes covalent cross-links between the hHsp60sp and the HLA-E to keep them together as a complex. The pDC(H)s may be fixed by paraformaldehyde (PFA), for example, 2% PFA.

The therapeutically effective amount of the autologous pDC(H)s is an amount of the autologous pDC(H)s required for correcting defective HLA-E restricted CD8+ Treg cells from a subject. The therapeutically effective amount may be determined by a physician.

In one embodiment of the present invention, a patient who has been diagnosed with having defective HLA-E restricted CD8+ Treg cells may be administered intravenously a treatment effective amount of the fixed hHsp60sp peptide-loaded dendritic cells (pDC(H)s) in a range between about $0.3\times10^6$ and about $90\times10^6$ cells, preferably about $2\times10^6$ and about $20\times10^6$ cells, most preferably about $7\times10^6$ and about $10\times10^6$ cells, in a suspension comprising pharmaceutically acceptable carriers.

In another embodiment, a patient who has been diagnosed with diagnosed with having defective HLA-E restricted CD8+ Treg cells may be administered intravenously a treatment effective amount of the fixed hHsp60sp peptide-loaded dendritic cells [pDC(H)s] in a range between about $0.3\times10^6$ and about $90\times10^6$ cells, preferably about $2\times10^6$ and about $20\times10^6$ cells, most preferably about $7\times10^6$ and about $10\times10^6$ cells, in a suspension comprising pharmaceutically acceptable carriers, two or more times separated by at least 14 days, preferably by 21 days.

In a further embodiment, a patient who has been diagnosed with diagnosed with having defective HLA-E restricted CD8+ Treg cells may be administered intravenously a treatment effective amount of the fixed hHsp60sp peptide-loaded dendritic cells [pDC(H)s] in a range between about between about $0.3\times10^6$ and about $90\times10^6$ cells, preferably about $2\times10^6$ and about $20\times10^6$ cells, most preferably about $7\times10^6$ and about $10\times10^6$ cells, in a volume between 10 ml and 50 ml, preferably between 15 ml and 30 ml, of a suspension comprising pharmaceutically acceptable carriers, two or more times separated by at least 14 days, preferably by at least 21 days.

In a further embodiment, a patient who has been diagnosed with diagnosed with having defective HLA-E restricted CD8+ Treg cells may be administered intravenously a treatment effective amount of the fixed hHsp60sp peptide-loaded dendritic cells [pDC(H)s) in a range between about $0.3\times10^6$ and about $90\times10^6$ cells, preferably between about $2\times10^6$ and about $20\times10^6$ cells, most preferably between about $7\times10^6$ and about $10\times10^6$ cells, in a volume between 10 ml and 50 ml, preferably between 15 ml and 30 ml, of a suspension pharmaceutically acceptable carriers, two or more times separated by 30 (+/−7) days.

The medium may comprise dimethyl sulfoxide (DMSO), human serum albumin (HSA) and PLASMA-LYTER® A. For example, the medium may include 2 mL dimethyl sulfoxide (DMSO), 10 mL 25% human serum albumin (HSA) and 8 mL PLASMA-LYTE® A.

The therapeutic composition may comprise a pharmaceutically acceptable carrier. The pharmaceutically acceptable carrier may be a pharmaceutically acceptable material, composition or vehicle, for example, a liquid or solid filler, diluent, excipient, solvent or encapsulating material depending on the route of administration.

The therapeutic composition comprises cells expressing DC markers. Suitable DC markers include CD11C and CD3. The therapeutic composition may comprise greater than 60%, 70%, 80% or 90% total CD11c+ (gated on large cells). For example, the therapeutic composition may comprise greater than 99.0-99.9% total CD11c+ (gated on large cells).

The therapeutic composition may be sterile. The sterility may be determined based on absence of detectable growth of bacteria, mycoplasma, and/or fungi in a testing sample for a predetermined period of time, for example, at least 14 days.

The therapeutic composition may further comprise a cryoprotectant. The cryoprotectant may be any substance that prevents or minimizes the damage to cells or tissues during freezing process and its subsequent storage period. The cryoprotectant may be selected from the group consisting of glycerol, propylene glycol, dimethyl sulfoxide (DMSO), and a combination thereof.

The therapeutic composition may be frozen. The therapeutic composition may be frozen by a conventional method. The therapeutic composition may be frozen in a controlled rate freezer, and then stored in vapor phase liquid nitrogen before use.

In one embodiment, the therapeutic composition is formulated for intravenous administration to the subject.

The subject may be a human individual. The subject may suffer from an autoimmune disease. The autoimmune disease may be selected from the group consisting of alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Behcet's disease, bullous pemphigoid, cardiomyopathy, celiac sprue-dermatitis, chronic fatigue syndrome immune, deficiency syndrome (CFIDS), chronic inflammatory demyelinating polyneuropathy, cicatricial pemphigoid, cold agglutinin disease, crest syndrome, Crohn's disease, Dego's disease, dermatomyositis, dermatomyositis-juvenile, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), IGA nephropathy, juvenile arthritis, Meniere's disease, mixed connective tissue disease, multiple sclerosis (MS), myasthenia gravis, pemphigus vulgaris, pernicious anemia, ply arteritis nodosa, polychondritis, polyglandular syndromes, polymyalgia rheumatic, polymyositis and dermatomyositis, psoriasis, Raynaud's phenomenon, Reiter's syndrome, rheumatic fever, rheumatoid arthritis, scleroderma, scleroderma, Sjogren's syndrome, stiff-man syndrome, systemic lupus erythematosus (SLE), Takayasu arteritis, temporal arteritis/giant cell arteritis, type 1 diabetes (T1D), ulcerative colitis, uveitis, vasculitis, vitiligo and Wegener's granulomatosis. In one embodiment, the autoimmune disease may be type 1 diabetes (T1D), multiple sclerosis (MS), psoriasis, lupus vitiligo, pemphigus or dermatomyositis. In another embodiment, the autoimmune disease is type 1 diabetes (T1D). In yet another embodiment, the autoimmune disease is multiple sclerosis (MS).

Second, the present invention provides a method for preparing a composition. The method comprises isolating mononuclear cells from a subject; incubating the mononuclear cells in a culture to produce dendritic cells (DCs); harvesting the DCs from the culture; incubating the harvested DCs with hHsp60sp to produce DCs loaded with the hHsp60sp (hHsp60sp loaded DCs); fixing the hHsp60sp loaded DCs to produced fixed hHsp60sp loaded DCs [pDC (H)s]; and suspending the pDC(H)s in a medium. As a result, the composition is prepared.

The mononuclear cells may be isolated from the subject by a conventional method (e.g., Leukapheresis). The isolated mononuclear cells may be incubated in a culture under conditions inducing production of DCs. The mononuclear cells may be incubated in the presence of one or more cytokines, for example, GM-CSF and IL-4.

The isolated mononuclear cells may be incubated in the culture for no more than 4-6 days, preferably no more than 6 days, to produce DCs. The DCs harvested from the mononuclear cells are incubated in the culture for no more than 6 days are immature DCs (iDCs). The iDCs may be characterized by a marker such as CD11c when harvested.

The harvested DCs may have a cell count of at least $2 \times 10^7$, $3 \times 10^7$, $4 \times 10^7$, $5 \times 10^7$, $6 \times 10^7$, $7 \times 10^7$, $8 \times 10^7$, $9 \times 10^7$ or $10 \times 10^7$.

The harvested DCs comprise cells expressing DC markers. The harvested DCs may comprise greater than 60%, 70%, 80% or 90% total CD11c+ (gated on large cells). For example, the harvested DCs may comprise greater than 99.0-99.9% total CD11c+ (gated on large cells).

The harvested DCs may be sterile. The sterility may be determined based on absence of detectable growth of bacteria, mycoplasma and/or fungi in a testing sample for a predetermined period of time, for example, at least 14 days.

In the peptide pulsing step, the harvested DCs (e.g., iDCs) are incubated with the hHsp60sp under conditions permitting association of the harvested DCs with the hHsp60sp. At least $3 \times 10^7$, $4 \times 10^7$, $5 \times 10^7$, $6 \times 10^7$, $7 \times 10^7$ or $8 \times 10^7$ harvested DCs may be incubated with the hHsp60sp. For example, a minimum of $5 \times 10^7$ DCs may be peptide pulsed with the hHsp60sp at 100-150 µM for 2 hours at 37° C., 5% $CO_2$ and 60-90% Relative Humidity (RH).

In the fixing step, the hHsp60sp loaded DCs may be fixed by a fixative that causes covalent cross-links between the hHsp60sp and HLA-E to keep them together in the complex. The hHsp60sp loaded DCs may be fixed by paraformaldehyde (PFA), for example, 2% PFA. The fixed hHsp60sp loaded DCs are also referred to as pDC(H)s.

In the suspending step, the pDC(H)s may be mixed with a medium of 1-100 mL, 5-50 mL, 10-50 mL, 15-30 mL, 18-22 mL or 20 mL. The medium may comprise dimethyl sulfoxide (DMSO), human serum albumin (HSA) and PLASMA-LYTE® A. In one embodiment, the medium includes 2 mL dimethyl sulfoxide (DMSO), 10 mL 25% human serum albumin (HSA) and 8 mL PLASMA-LYTE® A.

The prepared composition may comprise a pharmaceutically acceptable carrier. The pharmaceutically acceptable carrier may be a pharmaceutically acceptable material, composition or vehicle, for example, a liquid or solid filler, diluent, excipient, solvent or encapsulating material depending on the route of administration. The pharmaceutically acceptable carrier does not reduce the therapeutic effect of the pDC(H)s by, for example, more than 50%, 40%, 30%, 20%, 10% or 5%.

The prepared composition may comprise a cryoprotectant. The cryoprotectant may be any substance that prevents or minimizes damage to the pDC(H)s during the freezing process. The cryoprotectant may be selected from the group consisting of glycerol, propylene glycol, dimethyl sulfoxide (DMSO), and a combination thereof.

The preparation method may further comprise freezing the prepared composition. The prepared composition may be frozen by a conventional method. The prepared composition may be frozen in a controlled rate freezer, and then stored in vapor phase liquid nitrogen before use. The frozen pDC may remain effective at least 24 months.

The prepared composition may be formulated for administration to the subject via any route, for example, via an intravenous, oral, nasal, transmucosal, transdermal, intramuscular and subcutaneous route. In one embodiment, the prepared composition is formulated for intravenous administration to the subject According to the preparation method, the subject may be a human individual. The subject may suffer from an autoimmune disease, preferably the autoimmune disease is diagnosed within three months to one year from the present treatment. A shorter period between diagnosis of an autoimmune disease and treatment is mostly preferred. The autoimmune disease may be selected from the group consisting of alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Behcet's disease, bullous pemphigoid, cardiomyopathy, celiac sprue-dermatitis, chronic fatigue syndrome immune, deficiency syndrome (CFIDS), chronic inflammatory demyelinating polyneuropathy, cicatricial pemphigoid, cold agglutinin disease, crest syndrome, Crohn's disease, Dego's disease, dermatomyositis, dermatomyositis-juvenile, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), IGA nephropathy, juvenile arthritis, Meniere's disease, mixed connective tissue disease, multiple sclerosis (MS), myasthenia gravis, pemphigus vulgaris, pernicious anemia, ply arteritis nodosa, polychondritis, polyglandular syndromes, polymyalgia rheumatic, polymyositis and dermatomyositis, psoriasis, Raynaud's phenomenon, Reiter's syndrome, rheumatic fever, rheumatoid arthritis, scleroderma, scleroderma, Sjogren's syndrome, stiff-man syndrome, systemic lupus erythematosus (SLE), Takayasu arteritis, temporal arteritis/giant cell arteritis, type 1 diabetes (T1D), ulcerative colitis, uveitis, vasculitis, vitiligo and Wegener's granulomatosis. In one embodiment, the autoimmune disease may be type 1 diabetes (T1D), multiple sclerosis (MS), psoriasis, rheumatoid arthritis, lupus, vitiligo, pemphigus or dermatomyositis. In another embodiment, the autoimmune disease is type 1 diabetes (T1D). In yet another embodiment, the autoimmune disease is multiple sclerosis (MS).

The pDC(H)s prepared according to the preparation method of the present invention may be used in the therapeutic composition of the present invention.

Third, the present invention provides recombinant human cells.

A recombinant human cell comprising a heterologous gene encoding a fusion protein is provided. The recombinant cell expresses the fusion protein on the surface of the cell. The fusion protein comprises human leukocyte antigen system E (HLA-E) and hHsp60sp. The fusion protein may further comprise a linker between the HLA-E and the hHsp60sp. The linker may be 10-20 amino acids long. A Gly-Ser linker may be used. The recombinant human cell may also comprise a GFP protein or the like as an indicator. The recombinant cell may express the fusion protein and GFP protein permanently. The recombinant human cell is a cell line having an ATCC accession number of _PTA-127256. [HLA-E/hHsp60sp]

A recombinant human cell comprising a heterologous gene encoding a fusion protein is provided. The recombinant cell expresses the fusion protein on the surface of the cell. The fusion protein comprises human leukocyte antigen system E (HLA-E) and B7sp. The fusion protein may further comprise a linker between the HLA-E and the B7sp. The linker may be 10-20 amino acids long. A Gly-Ser linker may be used. The recombinant human cell may also comprise a GFP protein or the like as an indicator. The recombinant cell may express the fusion protein and GFP protein permanently. The recombinant human cell is a cell line having an ATCC accession number of PTA-127257. [HLA-E/B7sp]

Fourth, the present invention provides a HLA-E restricted CD8+ Treg specificity assay, also referred to as a potency assay. Testing HLA-E restricted CD8+ Treg cells from a subject may be characterized by its percentage of maximum inhibition in a potency assay (Inhibition Index). The testing HLA-E restricted CD8+ Treg cells are capable of specifically recognizing HLA-E/hHsp60sp complex (the biomarker) expressed on the target cells. The percentage of inhibition of the testing HLA-E restricted CD8+ Treg cells may be calculated based on the specific inhibition of specific target cells compared with control target cells, to test the function of HLA-E restricted CD8+ Treg cells in a Potency Assay. The percentage of inhibition for testing HLA-E restricted CD8+ Treg cells from a subject may be used to determine whether a subject has defective HLA-E restricted CD8+ Treg cells and whether defective HLA-E restricted CD8+ Treg cells from a subject are correctable. Here, the control target cells are cells expressing a complex of HLA-E and a control type A peptide, such as B7sp. The specific target cells are cells expressing a complex of HLA-E and Type B peptide, such as hHsp60sp. The specific target cells, the control target cells and the internal control cells are derived from the same parental cell line (e.g., B721).

In the Potency Assay, in each testing group of CD8+ T cells, specific and control target cells are plated into two separate rows in a 48-well plate and incubated in the absence of the CD8+ T cells (well 1 in each row), or in the presence of the testing CD8+ T cells (e.g. experimental wells 2-6 in each row). In both rows, the CD8+ T cells were acting as effector cells (E), at graded E/T ratios, for example, from 3:1 to 0.005:1. The inhibition curve will be calculated in both rows of a groups.

The specific target cells may comprise a first heterologous gene encoding a first fusion protein of the HLA-E and the hHsp60sp and express the first fusion protein on the surface of the specific target cells. The first fusion protein may further comprise a linker between the HLA-E and the hHsp60sp. The linker may be 10-20 amino acids long. A Gly-Ser linker may be used. The recombinant human cell may also comprise a GFP protein or the like as an indicator. The specific target cells may express the first fusion protein and GFP protein permanently. The specific target cells may be cells of the cell line having an ATCC accession number of PTA-127256.

The control target cells may comprise a second heterologous gene encoding a second fusion protein of HLA-E and B7sp and express the second fusion protein on the surface of the control target cells. The second fusion protein may further comprise a linker between the HLA-E and the B7sp. The linker may be 10-20 amino acids long. A Gly-Ser linker may be used. The recombinant human cell may also comprise a GFP protein or the like as an indicator. The control target cells may express the second fusion protein and GFP protein permanently. The control target cell may be of a cell line having an ATCC accession number of PTA-127257.

Proliferation of either specific target cells (hHsp60sp loaded B721/E mixed with B721 or TH1 mixed with B721) or control target cells (B7sp loaded B721/E mixed with B721 or TB1 mixed with B721) in the absence of testing CD8+ T cells (Control culture, well 1 of the row) or in the presence of testing CD8+ T cells (Experimental culture, well 2-6 of the row) at each of the grading E/T ratios is quantified. At each E/T ratio, a percentage of specific inhibition for the specific or control target cells is calculated based on the quantified proliferation of the Experimental ratio–Control ratio as follows:

$$\text{Specific inhibition(\%) of either specific targets or control targets} = (\text{Experimental ratio} - \text{Control ratio})/\text{Control ratio} \times 100\%.$$

The control ratio is the ratio of the quantified proliferation of the control target cells or the specific target cells in the absence of CD8+ T cells. The Experimental ratio is the quantified proliferation ratio of control target cells or the specific target cells in the presence of the gradient amount of testing CD8+ T cells. An inhibition curve may be generated to show percentages of specific inhibition for the specific target cells and control targets at different E/T ratios.

The percentage of maximum inhibition (Inhibition Index) for the testing HLA-E restricted CD8+ Treg cells equals to the percentage of the maximum inhibition for the specific target cells subtracted by the percentage of the maximum inhibition for the control target cells. The value of the Inhibition Index for the testing HLA-E restricted CD8+ Treg cells may be used to determine whether the testing HLA-E restricted CD8+ Treg cells are defective in a D0 assay and correctable in a D11 assay.

A method is provided to determine a percentage of maximum inhibition (Inhibition Index) for testing the function of the HLA-E restricted CD8+ Treg cells from a subject. The read out is the specific inhibition of the testing HLA-E restricted CD8+ Treg cells to suppress the specific target cells via a specific recognition of HLA-E/hHsp60sp complex (the biomarker) expressed on the target cells. This assay is to test if the HLA-E restricted CD8+ Treg cells are capable of specifically recognizing the "biomarker" (HLA-E/ hHsp60sp complex) expressed on the target cells. The method comprising (a) determining inhibition for specific target cells; (b) determining inhibition for control target cells; and (c) calculating maximum inhibition (Inhibition Index) of the testing HLA-E restricted CD8+ Treg cells 4-from each subject by subtracting the percentage of maximum inhibition for the control target cells from the percentage of maximum inhibition for the specific target cells. The specific target cells are cells expressing HLA-E/hHsp60sp complex (the biomarker) on the surface of the target cells. The control target cells are target cells expressing the HLA-E/control peptide complex (control for the biomarker) on the surface of the control target cells. The specific target cells may be the cell line having an ATCC accession number of PTA-127256 while the control target cells may be the cell line having an ATCC accession umber of PTA-127257.

According to the method of determining an "Inhibition Index" of testing HLA-E restricted CD8+ Treg cells from a subject, steps comprise (i) obtaining a specific target cell mixture having an equal number of specific or control target cells with the internal control target cell, e.g. B721; (ii) incubating the specific vs control target cell mixture in the absence or presence of the gradient testing HLA-E restricted CD8+ regulatory T cells in two separate rows; (iii) quantifying proliferation of the specific target cells as well as the control target cells to calculate the specific target cell mixture in the presence or absence of the testing HLA-E restricted CD8+ Treg cell at graded specific E/T ratios and (vi) calculating a percentage of maximum specific inhibition for the specific target cells (Inhibition Index) by picking up the highest % of inhibition of the "inhibition curve" of the specific targets, subtracted by the highest % of inhibition of the control targets.

According to the method of determining a percentage of maximum inhibition for testing HLA-E restricted CD8+ Treg cells from a subject, the specific target cells may be from the cell line having an ATCC accession number of PTA-127256 while the control target cells may be from the cell line having an ATCC accession number of PTA-127257.

According to the method of determining a percentage of maximum inhibition for testing HLA-E restricted CD8+ Treg cells from a subject, the subject may be a human individual. The subject may suffer an autoimmune disease. The autoimmune disease may be selected from the group consisting of alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Behcet's disease, bullous pemphigoid, cardiomyopathy, celiac sprue-dermatitis, chronic fatigue syndrome immune, deficiency syndrome (CFIDS), chronic inflammatory demyelinating polyneuropathy, cicatricial pemphigoid, cold agglutinin disease, crest syndrome, Crohn's disease, Dego's disease, dermatomyositis, dermatomyositis-juvenile, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), IGA nephropathy, juvenile arthritis, Meniere's disease, mixed connective tissue disease, multiple sclerosis (MS), myasthenia gravis, pemphigus vulgaris, pernicious anemia, ply arteritis nodosa, polychondritis, polyglandular syndromes, polymyalgia rheumatic, polymyositis and dermatomyositis, psoriasis, Raynaud's phenomenon, Reiter's syndrome, rheumatic fever, rheumatoid arthritis, scleroderma, scleroderma, Sjogren's syndrome, stiff-man syndrome, systemic lupus erythematosus (SLE), Takayasu arteritis, temporal arteritis/giant cell arteritis, type 1 diabetes (T1D), ulcerative colitis, uveitis, vasculitis, vitiligo and Wegener's granulomatosis. In one embodiment, the autoimmune disease may be type 1 diabetes (T1D), multiple sclerosis (MS), psoriasis, rheumatoid arthritis, lupus, vitiligo, pemphigus or dermatomyositis. In another embodiment, the autoimmune disease is type 1 diabetes (T1D). In yet another embodiment, the autoimmune disease is multiple sclerosis (MS).

A method is provided to determine whether HLA-E restricted CD8+ Treg cells freshly isolated from a subject are defective (D0 assay). The freshly isolated HLA-E restricted CD8+ Treg cells from normal healthy individuals are capable of selectively suppressing self-reactive T cells by specifically recognizing HLA-E/hHsp60sp complex expressed on the specific target cells. The method comprises determining a percentage of maximum inhibition (Inhibition Index) for the freshly isolated HLA-E restricted CD8+ Treg cells according to the method described above using the freshly isolated HLA-E restricted CD8+ Treg cells as the testing HLA-E restricted CD8+ Treg cells. In one embodiment, a percentage of maximum inhibition from a testing subject is less than 50% of HLA-E restricted CD8+ T cells freshly isolated from a normal healthy control subject indicates that the HLA-E restricted CD8+ Treg cells freshly isolated from the testing subject are defective, that is, the subject has defective HLA-E restricted CD8+ Treg cells.

According to the method of determining whether HLA-E restricted CD8+ Treg cells from a subject are defective, the specific target cells may be from the cell line having an ATCC accession number of PTA-127256 while the control target cells may be from the cell line having an ATCC accession number of PTA-127257.

According to the method of determining whether HLA-E restricted CD8+ Treg cells from a subject are defective, the subject may be a human individual. The subject may suffer an autoimmune disease. The autoimmune disease may be selected from the group consisting of alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Behcet's disease, bullous pemphigoid, cardiomyopathy, celiac sprue-dermatitis, chronic fatigue syndrome immune, deficiency syndrome (CFIDS), chronic inflammatory demyelinating polyneuropathy, cicatricial pemphigoid, cold agglutinin disease, crest syndrome, Crohn's disease, Dego's disease, dermatomyositis, dermatomyositis-juvenile, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), IGA nephropathy, juvenile arthritis, Meniere's disease, mixed connective tissue disease, multiple sclerosis (MS), myasthenia gravis, pemphigus vulgaris, pernicious anemia, ply arteritis nodosa, polychondritis, polyglandular syndromes, polymyalgia rheumatic, polymyositis and dermatomyositis, psoriasis, Raynaud's phenomenon, Reiter's syndrome, rheumatic fever, rheumatoid arthritis, scleroderma, scleroderma, Sjogren's syndrome, stiff-man syndrome, systemic lupus erythematosus (SLE), Takayasu arteritis, temporal arteritis/giant cell arteritis, type 1 diabetes (T1D), ulcerative colitis, uveitis, vasculitis, vitiligo and Wegener's granulomatosis. In one embodiment, the autoimmune disease may be type 1 diabetes (T1D), multiple sclerosis (MS), psoriasis, rheumatoid arthritis, lupus, vitiligo, pemphigus or dermatomyositis. In another embodiment, the autoimmune disease is type 1 diabetes (T1D). In yet another embodiment, the autoimmune disease is multiple sclerosis (MS).

A method is provided to determine whether defective HLA-E restricted CD8+ Treg cells from a subject are correctable (D11 Assay). The freshly isolated HLA-E restricted CD8+ Treg cells from normal healthy individuals or corrected dysfunctional HLA-E restricted CD8+ Treg cells are capable of selectively suppressing self-reactive T cells by specifically recognizing the complex of HLA-E/hHsp60sp expressed on the specific target cells. The defective HLA-E restricted CD8+ Treg cells are not capable of specifically recognizing complex of HLA-E/hHsp60sp expressed on the target cells. To test if the dysfunctional HLA-E restricted CD8+ Treg cells are correctable, the method (D11 assay) comprises: (a) triggering the defective HLA-E restricted CD8+ Treg cells with fixed autologous dendritic cells loaded with hHsp60 [pDC(H)s] to produce CD8(H) cells ex vivo; (b) determining a percentage of maximum inhibition for the CD8(H) cells according to the method descried above using the CD8(H) cells as the testing HLA-E restricted CD8+ regulatory T cells; (c) Triggering the defective HLA-E restricted CD8+ Treg cells with fixed autologous dendritic cells loaded with a control peptide [pDC(B)s] to produce CD8(B) cells ex vivo; (d) determining a percentage of maximum inhibition for the CD8(B) cells according to the method as described above using the CD8(B) cells as control of the testing HLA-E restricted CD8+ Treg cells; and (e) calculating a maximum inhibition (Inhibition Index) for the treated defective HLA-E restricted CD8+ Treg cells by subtracting the percentage of highest inhibition for the CD8(B) cells from the percentage of highest inhibition for the CD8(H) cells. In one embodiment, a percentage of maximum inhibition (Inhibition Index) for defective HLA-E restricted CD8+ Treg cells from a subject after ex-vivo trigger is greater than 50% of the normal healthy control subject tested that is built in within the same test indicates that the defective HLA-E restricted CD8+ Treg cells from the subject are correctable, that is, the subject has correctable defective HLA-E restricted CD8+ Treg cells.

According to the method of determining whether the defective HLA-E restricted CD8+ Treg cells from a subject are correctable, the defective HLA-E restricted CD8+ Treg cells are determined according to the method described above.

According to the method of determining whether the defective HLA-E restricted CD8+ T regulatory cells from a subject are correctable, where the defective HLA-E restricted CD8+ Treg cells from the subject are determined to be correctable, the method may further comprise correcting the defective HLA-E restricted CD8+ T cells by autologous pDC(H)s ex vivo and administering the pDC(H)s to the subject.

According to the method of determining whether the defective HLA-E restricted CD8+ T regulatory cells from a subject are correctable, the specific target cells may be of the cell line having an ATCC accession number of PTA-127256 (TH1) while the control target cells may be of the cell line having an ATCC accession number of PTA-127257 (TB1).

According to the method of determining whether the defective HLA-E restricted CD8+ Treg cells from a subject are correctable, the subject is a human individual. The subject may suffer from an autoimmune disease. The autoimmune disease may be selected from the group consisting of alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Behcet's disease, bullous pemphigoid, cardiomyopathy, celiac sprue-dermatitis, chronic fatigue syndrome immune, deficiency syndrome (CFIDS), chronic inflammatory demyelinating polyneuropathy, cicatricial pemphigoid, cold agglutinin disease, crest syndrome, Crohn's disease, Dego's disease, dermatomyositis, dermatomyositis-juvenile, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), IGA nephropathy, juvenile arthritis, Meniere's disease, mixed connective tissue disease, multiple sclerosis (MS), myasthenia gravis, pemphigus vulgaris, pernicious anemia, ply arteritis nodosa, polychondritis, polyglandular syndromes, polymyalgia rheumatic, polymyositis and dermatomyositis, psoriasis, Raynaud's phenomenon, Reiter's syndrome, rheumatic fever, rheumatoid arthritis, scleroderma, scleroderma, Sjogren's syndrome, stiff-man syndrome, systemic lupus erythematosus (SLE), Takayasu arteritis, temporal arteritis/giant cell arteritis, type 1 diabetes (T1D), ulcerative colitis, uveitis, vasculitis, vitiligo and Wegener's granulomatosis. In one embodiment, the autoimmune disease may be type 1 diabetes (T1D), multiple sclerosis (MS), psoriasis, rheumatoid arthritis, lupus, vitiligo, pemphigus or dermatomyositis. In another embodiment, the autoimmune disease is type 1 diabetes (T1D). In yet another embodiment, the autoimmune disease is multiple sclerosis (MS).

Fifth, the present invention provides a method for correcting defective HLA-E restricted CD8+ Treg cells in a subject in need thereof. The defective HLA-E restricted CD8+ Treg cells are correctable and capable of selectively down-regulating self-reactive T cells by specifically recognizing a complex of HLA-E/hHsp60sp expressed on the target self-reactive T cells in vivo after administrated with pDC(H)s which is capable of activating the HLA-E restricted CD8+ Treg cells, in vivo, to correct their function. The method comprises administering to the subject a therapeutically effective amount of a therapeutic composition. The therapeutic composition comprises fixed autologous dendritic cells loaded with the hHsp60sp (pDC(H)s) in a medium. The pDC(H)s have been fixed with paraformaldehyde (PFA).

According to the method of correcting defective HLA-E restricted CD8+ Treg cells in a subject in need thereof, whether a subject has defective HLA-E restricted CD8+ Treg cells may be determined by the assay described above based on the Inhibition Index for HLA-E restricted CD8+ Treg cells freshly isolated from the subject (D0 assay) followed by a D11 assay to test if the defective CD8+ Tregs can be corrected by ex-vivo retrigger with pDC(H)s, according to the present invention.

According to the method of correcting defective HLA-E restricted CD8+ Treg cells in a subject in need thereof, whether defective HLA-E restricted CD8+ Treg cells from a subject are correctable may be determined based on the Inhibition Index for the defective HLA-E restricted CD8+ Treg cells from the subject before (D0 assay) and after activation (D11 assay) by autologous pDC(H)s according to the present invention. The autologous pDC(H)s may be prepared according to the present invention. The autologous pDC(H)s may be in a therapeutic composition according to the present invention.

According to the correction method, the pDC(H)s may be fixed by a fixative that causes covalent cross-links between the hHsp60sp and HLA-E to keep them together in the complex and attached to an insoluble network without reducing the therapeutic effect of the pDC(H)s by, for example, more than 50%, 40%, 30%, 20%, 10% or 5%. The pDC(H)s may be fixed by paraformaldehyde (PFA), for example, 2% PFA.

Patients diagnosed with having defective HLA-E restricted CD8+ Treg cells may be treated with the therapeutic agent in the present invention by intravenous administration of the therapeutic agent at a dosing regimen determined by a medical professional.

In one embodiment of the present invention, a patient who has been diagnosed with having defective HLA-E restricted CD8+ Treg cells may be administered intravenously a treatment effective amount of the fixed hHsp60sp peptide-loaded dendritic cells [pDC(H)s] in a range between about $0.3\times10^6$ and about $90\times10^6$ cells, preferably about $2\times10^6$ and about $20\times10^6$ cells, most preferably about $7\times10^6$ and about $10\times10^6$ cells, in a suspension comprising pharmaceutically acceptable carriers.

In another embodiment, a patient who has been diagnosed with having defective HLA-E restricted CD8+ Treg cells may be administered intravenously a treatment effective amount of the fixed hHsp60sp peptide-loaded dendritic cells [pDC(H)s] in a range between about $0.3\times10^6$ and about $90\times10^6$ cells, preferably about $2\times10^6$ and about $20\times10^6$ cells, most preferably about $7\times10^6$ and about $10\times10^6$ cells, in a suspension comprising pharmaceutically acceptable carriers, two or more times separated by at least 14 days, preferably by at least 21 days.

In a further embodiment, a patient who has been diagnosed with having defective HLA-E restricted CD8+ Treg cells may be administered intravenously a treatment effective amount of the fixed hHsp60sp peptide-loaded dendritic cells [pDC(H)s] in a range between about between about $0.3\times10^6$ and about $90\times10^6$ cells, preferably about $2\times10^6$ and about $20\times10^6$ cells, most preferably about $7\times10^6$ and about $10\times10^6$ cells, in a volume between 10 ml and 50 ml, preferably between 15 ml and 30 ml, of a suspension comprising pharmaceutically acceptable carriers, two or more times separated by at least 14 days, preferably by at least 21 days.

In a further embodiment, a patient who has been diagnosed with having defective HLA-E restricted CD8+ Treg cells may be administered intravenously a treatment effective amount of the fixed hHsp60sp peptide-loaded dendritic cells [pDC(H)s] in a range between about $0.3\times10^6$ and about $90\times10^6$ cells, preferably between about $2\times10^6$ and about $20\times10^6$ cells, most preferably between about $7\times10^6$ and about $10\times10^6$ cells, in a volume between 10 ml and 50 ml, preferably between 15 ml and 30 ml, of a suspension pharmaceutically acceptable carriers, two or more times separated by 30 (+/−7) days.

According to the correction method, the medium may comprise dimethyl sulfoxide (DMSO), human serum albumin (HSA) and PLASMA-LYTE® A. For example, the medium may include 2 mL dimethyl sulfoxide (DMSO), 10 mL 25% human serum albumin (HSA) and 8 mL PLASMA-LYTE® A.

According to the correction method, the therapeutic composition may comprise a pharmaceutically acceptable carrier. The pharmaceutically acceptable carrier may be a pharmaceutically acceptable material, composition or vehicle, for example, a liquid or solid filler, diluent, excipient, solvent or encapsulating material depending on the route of administration. The pharmaceutically acceptable carrier does not reduce the therapeutic effect of the pDC(H)s by, for example, more than 50%, 40%, 30%, 20%, 10% or 5%.

According to the correction method, the therapeutic composition comprises cells expressing DC markers. Suitable DC markers include CD11C and CD3. The therapeutic composition may comprise greater than 60%, 70%, 80% or 90% total CD11c+ (gated on large cells). For example, the therapeutic composition may comprise greater than 99.0-99.9% total CD11c+ (gated on large cells).

According to the correction method, the therapeutic composition may be sterile. The sterility may be determined based on absence of detectable growth of bacteria and/or fungi in a testing sample for a predetermined period of time, for example, at least 14 days.

According to the correction method, the therapeutic composition may further comprise a cryoprotectant. The cryoprotectant may be any substance that prevents or minimizing freezing of tissues or damage to cells during freezing. The cryoprotectant may be selected from the group consisting of glycerol, propylene glycol, dimethyl sulfoxide (DMSO), and a combination thereof.

According to the correction method, the therapeutic composition may be frozen. The therapeutic composition may be frozen by a conventional method. The therapeutic composition may be frozen in a controlled rate freezer, and then stored in vapor phase liquid nitrogen before use.

According to the correction method, the therapeutic composition may be formulated for administration to the subject via any route, for example, via an intravenous, oral, nasal, transmucosal, transdermal, intramuscular and subcutaneous route. In one embodiment, the therapeutic composition is formulated for intravenous administration to the subject.

According to the correction method, the subject may be a human individual. The subject may suffer an autoimmune disease. The autoimmune disease may be selected from the group consisting of alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (ALPS), autoimmune thrombocytopenia purpura (ATP), Behcet's disease, bullous pemphigoid, cardiomyopathy, celiac sprue-dermatitis, chronic fatigue syndrome immune, deficiency syndrome (CFIDS), chronic inflammatory demyelinating polyneuropathy, cicatricial pemphigoid, cold agglutinin disease, crest syndrome, Crohn's disease, Dego's disease, dermatomyositis, dermatomyositis-juvenile, discoid lupus, essential mixed cryoglobulinemia, fibromyalgia-fibromyositis, Grave's disease, Guillain-Barre, Hashimoto's thyroiditis, idiopathic pulmonary fibrosis, idiopathic thrombocytopenia purpura (ITP), IGA nephropathy, juvenile arthritis, Meniere's disease, mixed connective tissue disease, multiple sclerosis (MS), myasthenia gravis, pemphigus vulgaris, pernicious anemia, ply arteritis nodosa, polychondritis, polyglandular syndromes, polymyalgia rheumatic, polymyositis and dermatomyositis, psoriasis, Raynaud's phenomenon, Reiter's syndrome, rheumatic fever, rheumatoid arthritis, scleroderma, scleroderma, Sjogren's syndrome, stiff-man syndrome, systemic lupus erythematosus (SLE), Takayasu arteritis, temporal arteritis/giant cell arteritis, type 1 diabetes (T1D), ulcerative colitis, uveitis, vasculitis, vitiligo and Wegener's granulomatosis. In one embodiment, the autoimmune disease may be type 1 diabetes (T1D), multiple sclerosis (MS), psoriasis, rheumatoid arthritis, lupus, vitiligo, pemphigus or dermatomyositis.

Sixth, the present invention provides a method for treating type 1 diabetes (T1D) in a subject in need thereof. The T1D treatment method comprises administering to the subject a therapeutically effective amount of a therapeutic composition. The therapeutic composition comprises autologous dendritic cells loaded with the hHsp60sp [pDC(H)s] in a medium. The pDC(H)s have been fixed with paraformaldehyde (PFA).

In the T1D treatment method, for being used as a therapy the autologous pDC(H)s may be prepared according to the present invention. The therapeutic composition is of the present invention.

According to the T1D treatment method, the hHsp60sp loaded DCs may be fixed by a fixative to produce fixed hHsp60sp loaded DCs [pDC(H)s]. The fixative causes covalent cross-links between the hHsp60sp and HLA-E to keep them together as the complex without reducing the therapeutic effect of the pDC(H)s by, for example, more than 50%, 40%, 30%, 20%, 10% or 5% as compared with the hHsp60sp loaded DCs. The hHsp60sp loaded DCs may be fixed by paraformaldehyde (PFA), for example, 2% PFA.

Patients diagnosed with autoimmune disorders or diseases such as T1D may be treated with the therapeutic agent in the present invention by intravenous administration of the therapeutic agent at a dosing regimen determined by a medical professional.

In one embodiment of the present invention, a patient who has been diagnosed with T1D may be administered intravenously a treatment effective amount of the fixed hHsp60sp peptide-loaded dendritic cells [pDC(H)s] in a range between about $0.3 \times 10^6$ and about $90 \times 10^6$ cells, preferably about $2 \times 10^6$ and about $20 \times 10^6$ cells, most preferably about $7 \times 10^6$ and about $10 \times 10^6$ cells, in a suspension comprising pharmaceutically acceptable carriers.

In another embodiment, a patient who has been diagnosed with T1D may be administered intravenously a treatment effective amount of the fixed hHsp60sp peptide-loaded dendritic cells [pDC(H)s] in a range between about $0.3 \times 10^6$ and about $90 \times 10^6$ cells, preferably about $2 \times 10^6$ and about $20 \times 10^6$ cells, most preferably about $7 \times 10^6$ and about $10 \times 10^6$ cells, in a suspension comprising pharmaceutically acceptable carriers, two or more times separated by at least 14 days, preferably by at least 21 days.

In a further embodiment, a patient who has been diagnosed with T1D may be administered intravenously a treatment effective amount of the fixed hHsp60sp peptide-loaded dendritic cells [pDC(H)s] in a range between about between about $0.3 \times 10^6$ and about $90 \times 10^6$ cells, preferably about $2 \times 10^6$ and about $20 \times 10^6$ cells, most preferably about $7 \times 10^6$ and about $10 \times 10^6$ cells, in a volume between 10 ml and 50 ml, preferably between 15 ml and 30 ml, of a suspension comprising pharmaceutically acceptable carriers, two or more times separated by at least 14 days, preferably by at least 21 days.

In a further embodiment, a patient who has been diagnosed with T1D may be administered intravenously a treatment effective amount of the fixed hHsp60sp peptide-loaded dendritic cells [pDC(H)s] in a range between about $0.3 \times 10^6$ and about $90 \times 10^6$ cells, preferably between about $2 \times 10^6$ and about $20 \times 10^6$ cells, most preferably between about $7 \times 10^6$ and about $10 \times 10^6$ cells, in a volume between 10 ml and 50 ml, preferably between 15 ml and 30 ml, of a suspension pharmaceutically acceptable carriers, two or more times separated by 30 (+/−7) days.

T1D may be diagnosed in accordance with any medically acceptable standards by a competent medical professional or a person skilled in the art, preferably, the diagnosis may be confirmed by positive lab result for one or more of the autoantibodies glutamic acid decarboxylase (GAD65), insulinoma associated protein 2 (IA-2, also known as ICA-512) and Zinc transporter 8 (ZnT8).

According to the method of treating T1D patients with present therapeutic composition, determination whether a T1D patient has defective HLA-E restricted regulatory CD8+ T cells or pathway prior to the treatment is not required so long as the patient has been diagnosed by a conventional diagnostic method practiced by a person ordinary skilled in the art.

As understood by a person skilled in the art, all dosing regimens described herein may be modified or adjusted depending on an individual patient' physical conditions and needs when treating the patient. Those embodiments may be used singularly, in any combination, or in any arrangement to the extent within the skill and knowledge of a person skilled in the art.

According to the T1D treatment methods, the medium may comprise dimethyl sulfoxide (DMSO), human serum albumin (HSA) and PLASMA-LYTE® A. For example, the medium may include 2 mL dimethyl sulfoxide (DMSO), 10 mL 25% human serum albumin (HSA) and 8 mL PLASMA-LYTE® A.

According to the T1D treatment method, the therapeutic composition may comprise a pharmaceutically acceptable carrier. The pharmaceutically acceptable carrier may be a pharmaceutically acceptable material, composition or vehicle, for example, a liquid or solid filler, diluent, excipient, solvent or encapsulating material depending on the route of administration. The pharmaceutically acceptable carrier does not reduce the therapeutic effect of the pDC(H)s by, for example, more than 50%, 40%, 30%, 20%, 10% or 5%.

According to the T1D treatment method, the therapeutic composition comprises cells expressing DC markers. Suitable DC markers include CD11C and CD3. The therapeutic composition may comprise greater than 60%, 70%, 80% or 90% total CD11c+ (gated on large cells). For example, the therapeutic composition may comprise greater than 99.0-99.9% total CD11c+ (gated on large cells).

According to the T1D treatment method, the therapeutic composition may be sterile. The sterility may be determined based on absence of detectable growth of bacteria and/or fungi in a testing sample for a predetermined period of time, for example, at least 14 days.

According to the T1D treatment method, the therapeutic composition may further comprise a cryoprotectant. The cryoprotectant may be any substance that prevents or minimizing damage to cells during freezing process. The cryoprotectant may be selected from the group consisting of glycerol, propylene glycol, dimethyl sulfoxide (DMSO), and a combination thereof.

According to the T1D treatment method, the therapeutic composition may be frozen. The therapeutic composition may be frozen by a conventional method. The therapeutic composition may be frozen in a controlled rate freezer, and then stored in vapor phase liquid nitrogen before use.

According to the T1D treatment method, the therapeutic composition may be formulated for administration to the subject via any route, for example, via an intravenous, oral, nasal, transmucosal, transdermal, intramuscular and subcutaneous route. In one embodiment, the therapeutic composition is formulated for intravenous administration to the subject.

According to the T1D treatment method, the therapeutic composition may be administered to the subject at least twice separated by at least 14 days, or by at least three times separated by at least 21 days.

According to the T1D treatment method, patients receiving the present therapeutic composition may be treated within 12 months after the T1D diagnosis, preferably within three months after the diagnosis. Earlier treatment after T1D diagnosis is beneficial to patients who receive the treatment of the present therapeutic composition. Patients receiving the present treatment may be a minor.

Seventh, the present invention provides a method for treating multiple sclerosis (MS) in a subject in need thereof. The MS treatment method comprises administering to the subject a therapeutically effective amount of a therapeutic composition. The therapeutic composition comprises autologous dendritic cells loaded with the hHsp60sp [pDC(H)s] in a medium. The pDC(H)s have been fixed with paraformaldehyde (PFA).

In the MS treatment method, the autologous pDC(H)s may be prepared according to the present invention. The therapeutic composition is of the present invention.

According to the MS treatment method, the pDC(H)s may be fixed by a fixative that causes covalent cross-links between the hHsp60sp and HLA-E to keep them together in the complex and attached to an insoluble network without reducing the therapeutic effect of the pDC(H)s by, for example, 2% PFA.

Patients diagnosed with autoimmune disorders or diseases such as MS may be treated with the therapeutic agent in the present invention by intravenous administration of the therapeutic agent at a dosing regimen determined by a medical professional.

In one embodiment of the present invention, a patient who has been diagnosed with MS may be administered intravenously a treatment effective amount of the fixed hHsp60sp peptide-loaded dendritic cells [pDC(H)s] in a range between about $0.3 \times 10^6$ and about $90 \times 10^6$ cells, preferably about $2 \times 10^6$ and about $20 \times 10^6$ cells, most preferably about $7 \times 10^6$ and about $10 \times 10^6$ cells, in a suspension comprising pharmaceutically acceptable carriers.

In another embodiment, a patient who has been diagnosed with MS may be administered intravenously a treatment effective amount of the fixed hHsp60sp peptide-loaded dendritic cells [pDC(H)s] in a range between about $0.3 \times 10^6$ and about $90 \times 10^6$ cells, preferably about $2 \times 10^6$ and about $20 \times 10^6$ cells, most preferably about $7 \times 10^6$ and about $10 \times 10^6$ cells, in a suspension comprising pharmaceutically acceptable carriers, two or more times separated by at least 14 days, preferably by at least 21 days.

In a further embodiment, a patient who has been diagnosed with MS may be administered intravenously a treatment effective amount of the fixed hHsp60sp peptide-loaded dendritic cells [pDC(H)s] in a range between about between about $0.3 \times 10^6$ and about $90 \times 10^6$ cells, preferably about $2 \times 10^6$ and about $20 \times 10^6$ cells, most preferably about $7 \times 10^6$ and about $10 \times 10^6$ cells, in a volume between 10 ml and 50 ml, preferably between 15 ml and 30 ml, of a suspension comprising pharmaceutically acceptable carriers, two or more times separated by at least 14 days, preferably by at least 21 days.

In a further embodiment, a patient who has been diagnosed with MS may be administered intravenously a treatment effective amount of the fixed hHsp60sp peptide-loaded dendritic cells [pDC(H)s] in a range between about $0.3 \times 10^6$ and about $90 \times 10^6$ cells, preferably between about $2 \times 10^6$ and about $20 \times 10^6$ cells, most preferably between about $7 \times 10^6$ and about $10 \times 10^6$ cells, in a volume between 10 ml and 50 ml, preferably between 15 ml and 30 ml, of a suspension pharmaceutically acceptable carriers, two or more times separated by 30 (+/−7) days.

According to the MS treatment methods, the medium may comprise dimethyl sulfoxide (DMSO), human serum albumin (HSA) and PLASMA-LYTE® A. For example, the medium may include 2 mL dimethyl sulfoxide (DMSO), 10 mL 25% human serum albumin (HSA) and 8 mL PLASMA-LYTE® A.

According to the MS treatment method, the therapeutic composition may comprise a pharmaceutically acceptable carrier. The pharmaceutically acceptable carrier may be a pharmaceutically acceptable material, composition or vehicle, for example, a liquid or solid filler, diluent, excipient, solvent or encapsulating material depending on the route of administration. The pharmaceutically acceptable carrier does not reduce the therapeutic effect of the pDC(H)s by, for example, more than 50%, 40%, 30%, 20%, 10% or 5%.

According to the MS treatment method, the therapeutic composition comprises cells expressing DC markers. Suitable markers to detect the harvested CDs include CD11C and CD3. The therapeutic composition may comprise greater than 60%, 70%, 80% or 90% total CD11c+ (gated on large cells). For example, the therapeutic composition may comprise greater than 99.0-99.9% total CD11c+ (gated on large cells).

According to the MS treatment method, the therapeutic composition may be sterile. The sterility may be determined based on absence of detectable growth of bacteria and/or fungi in a testing sample for a predetermined period of time, for example, at least 14 days.

According to the MS treatment method, the therapeutic composition may further comprise a cryoprotectant. The cryoprotectant may be any substance that prevents or minimizing damage to cells during freezing process. The cryoprotectant may be selected from the group consisting of glycerol, propylene glycol, dimethyl sulfoxide (DMSO), and a combination thereof.

According to the MS treatment method, the therapeutic composition may be frozen. The therapeutic composition may be frozen by a conventional method. The therapeutic composition may be frozen in a controlled rate freezer, and then stored in vapor phase liquid nitrogen before use.

According to the MS treatment method, the therapeutic composition may be formulated for administration to the subject via any route, for example, via an intravenous, oral, nasal, transmucosal, transdermal, intramuscular and subcutaneous route. In one embodiment, the therapeutic composition is formulated for intravenous administration to the subject.

According to the MS treatment method, the therapeutic composition may be administered to the subject at least twice separated by at least 14 days, or by at least three times separated by at least 21 days.

According to the MS treatment method, determination whether a MS patient has defective HLA-E restricted regulatory CD8+ T cells or pathway prior to the treatment is not required so long as the patient has been diagnosed by a conventional diagnostic method practiced by a person ordinary skilled in the art.

Example 1. Manufacture of Fixed hHsp60sp Loaded Autologous Dendritic Cells [PDC(H)s]

Autologous dendritic cells loaded with a hHsp60sp were manufactured by collecting mononuclear cells from a subject (e.g., patient) by leukapheresis collection and cell separation/enrichment, differentiating the collected primary mononuclear cells into dendritic cells (DCs) in cell cultures in the presence of GM-CFS and IL-4, harvesting immature DCs (iDCs), loading the harvested iDCs with the hHsp60sp (SEQ ID NO: 1), and fixing hHsp60sp loaded DCs to stabilize the association of HLA-E and the hHsp60sp on the DCs before being fixed to produce pDC(H)s. The pDC(H)s may be a Therapeutic Agent for administration to the subject.

Key reagents and excipients used in manufacturing the pDC(H)s, including their sources and grades, are shown in Table 1.

B. Dendritic Cells (DCs)

On Day 0, the collected mononuclear cells were seeded into flasks, for example, Triple Flasks or TC Flasks, and incubated at 37° C. for 1.5 to 2 hours to allow monocytes to adhere to the bottom of the flasks. Non-adherent monocytes were decanted while the adherent monocytes were washed several times with PBS to remove as many non-adherent cells as possible. Cell Genex DC Media with cytokines IL-4

TABLE 1

| Reagents and essential supplies used in manufacture of pDC(H)s | | | | |
|---|---|---|---|---|
| Reagent/ Excipient | Use | Concentration at Use | Source | Grade |
| Ficoll-Paque Premium | Density Gradient | N/A | GE | GMP |
| Cell Genix DC Media | Culture | N/A | Cell Genix | GMP |
| Phosphate Buffered Saline (PBS) | In process washing, and dilution of PFA | 1X | Gibco or equivalent | Research |
| RMPI media | Dilution and in process washing | N/A | Lonza or equivalent | Research |
| Fetal Boven serum | To make the complete medium | 10% | Biotechne | |
| GM-CSF | Culture additive | 80 ng/mL | Genzyme | USP |
| IL-4 | Culture additive | 20 ng/mL | Miltenyi Biotec or equivalent | Research |
| Hsp60sP Peptide | Peptide pulsing | 100-150 μM | Polypeptide Group AG | GMP |
| Paraformaldehyde Solution | Preparation of THE THERAPEUTIC AGENT | 2% | Electron Microscopy Sciences | Research |
| 25% Human Serum Albumin (25% HSA) | Washes and Cryopreservation | N/A | Grifols or equivalent | USP |
| Dimethyl Sulfoxide (DMSO) | Cryopreservation | 10% | Bioniche or equivalent | GMP USP for sterility and endotoxin |
| PLASMA-LYTE ® A | Cryopreservation | N/A | Baxter | USP |
| Distilled Water | Dilution of peptide and Preparation of stock solution | N/A | Gibco or equivalent | Research |
| Water for Injection | Preparation of stock solution of cytokines | N/A | Hospira | USP |

The hHsp60sp is the human heat shock protein 60 signal peptide consisting of the amino acid sequence of SEQ ID NO: 1, having a molecular weight (MW) of 1086.33 and in the form of white powder. The hHsp60sp was reconstituted with ddH2O to obtain a final concentration of 2 mM. Aliquots of the reconstituted hHsp60sp is filtered and aliquoted in 400 μL were stored at ≤−130° C. prior to use.

A. Mononuclear Cells

Peripheral blood mononuclear cells (PBMCs) were obtained from a subject through apheresis of therapeutic cells (TC-apheresis). Approximately 15 L blood from the subject was processed on the Fenwal Amicus Cell Separator, CaridianBCT Spectra Optia, or equivalent system to obtain a leukapheresis product containing white blood cells at about $1-2 \times 10^{10}$.

In the next morning after the leukapheresis product was obtained (Day 0), a small portion (e.g., 1-3 mL from 200 mL) was removed from the leukapheresis product for initial quality control (QC) testing, including total nucleated cells (TNC) using automated cell count, Trypan viability, sterility using Bac-T Alert and QC vials. The leukapheresis product was diluted in RPMI and then subject to density gradient performed using Ficoll-Paque Premium so that mononuclear cells were collected. The collected mononuclear cells were washed several times and then subject to pre-culture QC testing, including TNC using automated cell count and Trypan viability.

at 20 ng/ml and GM-CSF at 80 ng/ml was added into the flasks to induce differentiation of the adherent monocytes into dendritic cells (DCs), and the cells in the flasks were incubated at 37° C., 5% $CO_2$ and 60-90% relative humidity (RH).

On Day 2-3 and Day 4-5, approximately half the culture medium in the flasks was removed and replaced with fresh DC media with cytokines IL-4 at 20 ng/ml and GM-CSF at 80 ng/mL to induce differentiation of the adherent monocytes into dendritic cells (DCs), and the cells in the flasks were incubated at 37° C., 5% $CO_2$ and 60-90% RH. As a result, immature DCs (iDCs) were obtained.

C. Dendritic Cells Loaded with hHsp60sp (pDC(H)s)

On Day 5 or D6, the DCs in suspension were harvested in Gibco Roswell Park Memorial Institute (RPMI). The flasks were washed extensively with RPMI to harvest all of the DCs. The harvested DCs were centrifuged and resuspended. The harvested and resuspended cells were DCs and subject to QC testing, including sterility, manual cell count, viability (Trypan), immunophenotyping, QC vials and mycoplasma.

After resuspension, the harvested DCs were pulsed with the hHsp60sp. A minimum of $4-5 \times 10^7$ harvested DCs were incubated with the hHsp60sp peptide at 100-150 μM for 2 hours at 37° C., 5% $CO_2$ and 60-90% RH to make hHsp60sp peptide pulsed DCs, also referred to as DCs loaded with the hHsp60sp peptide. The hHsp60 peptide pulsed DCs were washed 1× with PBS before being fixed with a 2% Paraformaldehyde solution for 10 minutes at 4° C. to make pDC(H)s. Following fixation, the pDC(H)s were washed 3x with PBS supplemented with human serum albumin (HSA) to optimize cell recovery. The pDC(H)s may be used as a Therapeutic Agent to treat the subject who is a patient.

After the washes, samples of the pDC(H)s were removed for QC testing, including Manual Cell Count, immunophenotyping, endotoxin (supernatant) and functional assays.

For each patient, 3-5 20-mL bags of pDC(H)s were prepared. Each bag contains about $1\text{-}1.2\times10^7$ pDC(H)s in a medium, which included 2 mL DMSO, 10 mL of 25% HSA and 8 mL of PLASMA-LYTE® A. After the addition of cryoprotectant, sterility testing of the pDC(H)s was performed. The pDC(H)s in the bags were frozen in a controlled rate freezer, and then stored in vapor phase liquid nitrogen ($LN_2$) until release testing was complete.

The DC percentage in the total harvested cell population varies among patients. In a small group of patients, the CD11c+ cells in the total harvested cell population may be lower than 20%. Under these circumstances, the amount of harvested DCs to be pulsed and fixed may be determined on a case-by-case basis to satisfy the required cell number in the final product.

Because the association between the DCs and the hHsp60sp peptide is unstable, the inventor has surprisingly discovered that fixing the hHsp60sp peptide-loaded dendritic cells, for example, by 2% paraformaldehyde (PFA), stabilizes the complex of HLA-E/hHsp60sp on the surface of the DCs. The DCs may also be fixed by other conventional methods known to a person skilled in the art, for example, cross-linking. It is desirable to fix the DCs as soon as possible after the wash to stabilize the association between the HLA-E on DCs and the hHsp60sp peptide. It is preferably to fix the DCs no more than 25 minutes after the wash, and more preferably no more than about 10-15 minutes after the wash.

Example 2. In-Process Testing

Various tests may be conducted during the process for making the pDC(H)s as described in Example 1. Table 2 lists some in-process tests, expected results and testing methods.

TABLE 2

| In-process tests | | | |
|---|---|---|---|
| Stage | Test | Expected Result | Method |
| Initial | 14 Day Sterility | No Growth | Bac-T Alert |
| | Cell Counts | $>1 \times 10^{10}$ | Automated |
| Pre-Culture (post Ficoll) | Cell Counts | $>1 \times 10^{10}$ | Automated |
| Harvested iDC | Cell Count | $>3 \times 10^7$ | Manual |
| | Immunophenotyping Total CD11C+ (gated on large cells) | >70% | Flow Cytometry |
| | Immunophenotyping Total CD3+ (gated on total cells) | Record result | Flow Cytometry |
| | 14 Day Sterility | No Growth | Bac-T Alert |
| Therapeutic agent | Potency Assay | *(−) or (+) | |
| | Immunophenotyping Total CD3+ (gated on total cells) | Record result | Flow Cytometry |

*A percentage of maximum inhibition (Inhibition Index) from a testing subject less than 50% of HLA-E restricted CD8+ T cells freshly isolated from a normal healthy control subject indicates that the HLA-E restricted CD8+ T cells freshly isolated from the testing subject are defective, that is, the subject has defective HLA-E restricted CD8+ Treg cells, and vice versa.

40

A. Sterility (Bacterial and Fungal Testing)

Sterility testing may be performed on the bioMerieux's BacT/Alert® 3D Microbial Detection System. This method has been validated against the 21 CFR 610.12 Millipore Steritest filtration methods. The BacT/Alert system is found to have a quicker time to detection at the same sensitivity level. Samples are directly inoculated into the BacT culture bottles (AST and NST). The bottles are then loaded into the BacT/Alert® 3D analyzer, and incubated for 14-days at a temperature range between 30-35° C. If microorganisms are present in bottles, they will produce carbon dioxide as they metabolize substrates in the media. This carbon dioxide changes sensors at the bottom of the bottles from blue-green to yellow. Using this sensor and reflected light, the BacT/Alert monitors the production of carbon dioxide and signals users if it determines bottles to be positive. If, at the end of 14-day incubation, the system does not determine bottles to be positive, it will report them as negative. If the system detects CO2 production, it will report that bottle as positive. If a positive is detected during the 14-day incubation phase, the bottle will be off loaded and a sample sent for identification and sensitivities. Samples for confirmatory testing (gram stain, identification and sensitivities) are sent to a qualified microbiology lab.

B. Endotoxin

Endotoxins are wall constituents of gram-negative bacteria that are liberated during bacterial growth and bacterial death. As such, detection of endotoxin is an indirect measurement of the current or recent presence of bacteria in the cell culture or associated reagents and supplies. Endotoxin in the final formulation cryopreserved products may be detected using the Endosafe PTS™. It is a handheld spectrophotometer that utilizes FDA-licensed LAL disposable cartridges.

C. Mycoplasma

Mycoplasma testing may be performed by an approved vendor laboratory (WuXi AppTec) using an approved Polymerase Chain Reaction kit (GLP 30645).

D. Immunophenotyping

The expression of cell surface DC biomarkers may be monitored by fluorescence-activated cell sorting (FACS) analysis to ensure the immature DC (iDC) phenotype. Both the post-harvest products (e.g., the harvested DCs) and final products (e.g., pDC(H)s) were measured for surface expression of CD11c. The final product must contain ≥80% CD11c gated on the DC population (large cells). T-Cell marker (CD3) was analyzed on the total cell population and the expected result should be ≤50%, but this is not a release criterion.

E. "Potency Assay"—HLA-E Restricted CD8+ Treg Specificity Assay

The "Potency Assay" provides a method for determining if testing HLA-E restricted CD8+ T cells, which specifically recognize or bind the complex of HLA-E coupled with hHsp60sp peptide (SEQ ID NO: 1), have a defect in inhibiting proliferation of specific target cells expressing HLA-E associated with the hHsp60sp peptide ("H cells") as compared with that of control target cells expressing on their surface a false marker such as HLA-E associated with B7sp (SEQ ID NO: 2) ("B cells"). This method may be used 1) to identify a patient who has defective HLA-E restricted CD8+ T cells and determine if the defect can be corrected; 2) to evaluate potency or function of the pDC(H)s as a therapeutic agent to correct the defect and treat any disease or disorder caused by the defect; and/or 3) to monitor efficacy of the therapeutic agent after the treatment.

Where the testing HLA-E restricted CD8+ T cells are freshly isolated from a subject (e.g., patient) and fail to inhibit the growth of the H cells as compared with the B cells, the testing HLA-E restricted CD8+ T cells are deemed to have a defect and the subject is deemed to need a correction of such defect. For example, in a D0 assay of the Potency Assay, the "Inhibition Index", a difference between the percentage of the maximum inhibition of the H cells and the percentage of the maximum inhibition of the B cells, that is less than 50% of the "Inhibition Index" of a sample that is from a healthy normal subject built in the same test as a Normal Control, indicates that the testing HLA-E restricted CD8+ T cells from the subject have a defect.

Where the defective testing HLA-E restricted CD8+ T cells inhibits the H cells as compared with the B cells after being activated by the pDC(H)s, tested in a D11 assay of the Potency Assay, indicating that 1) the patients' defective HLA-E restricted CD8+ Treg cells are correctable and 2). The pDC(H)s are deemed potent for correcting the defect of the testing HLA-E restricted CD8+ T cells and may be used as a therapeutic agent for treating a disease or condition caused by the defective testing HLA-E restricted CD8+ T cells in the subject. For example, in D11 assay, a net value, i.e., a difference between the percentage of the maximum inhibition of the H cells and the percentage of the maximum inhibition of the B cells (the "Inhibition Index"), that is greater than 50% of the Inhibition Index of a sample that is from a healthy normal subject built in the same test as a Normal Control, indicates that the defective testing HLA-E restricted CD8+ T cells can be corrected by the potent pDC(H)s.

1. Protocol

In general, the potency assay includes four steps.

First, target cells are plated. The two types of target cells are specific target cells expressing the complex of HLA-E associated with the hHsp60sp peptide ("H cells") and control target cells expressing on their surface a false marker such as the complex of HLA-E associated with the B7sp peptide ("B cells"). A system control of parental cell line B721 are mixed with either the specific or control target cells at 1:1 ratio to generate a specific or control target cell mixture. The two target cell mixtures are each plated into six wells of a 48 well plate at an equal amount.

Second, the testing CD8+ T cells are added into five of the six wells of each row in a 48-plate plate (well 2-6) to contact with either the specific or control target cell mixture in a limiting dilution fashion, leaving the number one well (well 1) without adding the testing T cells to establish an "inhibition curve" of the specific or control target cells for the assessment of the function of the testing CD8+ T cells.

Third, the plates are incubated at 37° C., 5% $CO_2$ for 5-7 days.

Fourth, the readout is the suppression or inhibition of the testing CD8+ T cells on proliferation of the specific target cells vs that on the control target cells. An "inhibition curve" for the testing CD8+ T cells is established on both specific and control target cells by calculating the number of the target cells after incubation for 5-7 days with the testing T cells. An "inhibition index" for the testing CD8+ T cells is determined by the difference between inhibition highest values of the specific inhibition curve and the highest value of the control inhibition curve.

2. Potency assay (D11 assay) to test 1). if the defective HLA-E restricted CD8+ Treg cells triggered by pDC (H)s regained the normal function or 2). If the pDC(H)s manufactured has the capacity to activate the defective HLA-E restricted CD8+ Treg cells.

The potency of the pDC(H)s is evaluated by testing if the defective testing CD8+ T cells regain the normal function of CD8+ T cells triggered by the pDC(H)s.

Two testing CD8+ T cell lines CD8(H) and CD8(B) may be established. The CD8(H) line was generated by co-culturing 0.4-0.5M×10$^6$ of purified autologous CD8+ T cells with 0.1-0.35×10$^6$ pDC(H)s in 1 mL/well in a 48 well plate, and thus activated by pDC. The CD8(B) line was generated by co-culturing 0.4-0.5M×10$^6$ of purified autologous CD8+ T cells with 0.1-0.35×10$^6$ DCs loaded with the peptide B7sp peptide in 1 mL/well in a 48 well plate, and thus serves as a negative control for CD8(H). IL-2 was added on the second day. CD8(H) cells and CD8(B) cells were harvested on D5 for a potency assay. In each potency assay, the CD8(H) or CD8(B) cells were tested for their effect on proliferation of target cells.

There are two types of target cells that were prepared and used:

1). The first type of targets: hHsp60sp loaded B721/E cells mixed with *CFSE (carboxyfluorescein succinimidyl ester) labeled B721 cells (specific target cell mixture) vs B7sp loaded B721/E cells mixed with *CFSE (carboxyfluorescein succinimidyl ester) labeled B721 cells (control target cell mixture).

*Here the hHsp60sp or B7sp loaded B721/E cells could be separated from CFSE labeled B721 cells by the Facs analysis.

2) The second type of targets:

TH1 cells (expressing HLA-E/hHsp60sp complex and GFP protein on the surface) mixed with unlabeled B721 as specific target cell mixture; and TB1 cells (expressing HLA-E/B7sp complex and GFP protein on the surface) mixed with unlabeled B721 as control target cell mixture.

**Here the GPF protein on TH1 and TB1 cells could separate these two cell lines from the unlabeled B721 by the Facs analysis.

A graded number of CD8(H) and CD8(B) cells were plated into a 48-well plate in two separate rows as the E/T ratio from 3:1 to 0.01:1 (well 2-6 on each row).

An equal number of the specific targets (hHsp60sp loaded B721/E or TH1 cells) and control targets (B7sp loaded B721/E or TB1 cells) are mixed with either CFSE labeled B721 cells (the first type target cells) or unlabeled B721 cells (the second type of targets). The two mixtures of specific vs control targets will be added to each well on a row of 6 wells of pre-plated rows of graded number of the CD8(H) or CD8(B) cells with the same amount of calculated numbers based on the E/T ratio from 3:1 to 0.01:1 (well 6-2) while each well 1 on the row is without CD8+ T cells.

Cell mixtures were cultured for 5-7 days at 37° C., 5% of $CO_2$ and assessed by FACS analysis in which the CD8(H) and CD8(B) cells were gated out during the analysis. The Ratio of Experimental culture of specific target cells and control target cells from well 2-6 of each row containing the graded number of CD8+ T cells as well as the ratio of Control culture of specific target cells and control target cells from well 1 of each row without CD8+ T cells were determined.

Proliferation of the testing cultures on either specific target cells (hHsp60sp loaded B721/E mixed with B721 or TH1 mixed with B721) or control target cells (B7sp loaded B721/E mixed with B721 or TB1 mixed with B721) in the absence of testing CD8+ T cells are Control cultures (well 1) or in the presence of testing CD8+ T cells are Experimental cultures, at each of the grading E/T ratios (well 2-6) were quantified. At each E/T ratio, a percentage of specific inhibition (potency) for both specific or control cultures is calculated based on the quantified proliferation of the Experimental ratio and Control ratio as follows:

$$\text{Specific inhibition(\%) of either specific targets or control targets} = (\text{Control ratio} - \text{Experimental ratio})/\text{Control ratio} \times 100\%.$$

The control ratio is the ratio of the quantified proliferation of the control target cells (B7sp loaded B721/E mixed with B721 or TB1 mixed with B721) or the specific target cells (hHsp60sp loaded B721/E mixed with B721 or TH1 mixed with B721) in the absence of CD8+ T cells (well 1 in each row). The Experimental ratio is the quantified proliferation ratio of control target cells (B7sp loaded B721/E mixed with B721 or TB1 mixed with B721) or the specific target cells (hHsp60sp loaded B721/E mixed with B721 or TH1 mixed with B721) in the presence of the graded amount of testing CD8+ T cells (at each E/T ration, well 2-6). An inhibition curve may be generated to show percentages of specific inhibition for the specific target cells or control targets at different E/T ratios.

The percentage of maximum inhibition (Inhibition Index) for the testing HLA-E restricted CD8+ Treg cells equals to the percentage of the maximum inhibition for the specific target cells subtracted by the percentage of the maximum inhibition for the control target cells. The value of the Inhibition Index for the testing HLA-E restricted CD8+ Treg cells may be used to determine whether the testing HLA-E restricted CD8+ Treg cells are defective in a D0 assay and correctable in a D11 assay.

3. Validation

Initial validation of the potency assay was performed and the representative data is provided in Table 3 below using the first type of targets mentioned above. The validation was performed in three healthy individuals, each had three tests. From our experience, the values among different individuals vary from person to person in the range of 10-40%. However, for each individual tested, the values are consistent from different tests as summarized in Table 3.

The % of Max Inhibition (i.e., peak of inhibition curve) of testing CD8+ T cells is calculated as: % of Max Inhibition of target cells loaded with the hHsp60sp peptide (specific target cells; H cells)–% of Max Inhibition in the group of control target cells loaded with the B7 peptide (control target cells; B cells).

The E/T ratio of Max Inhibition of testing CD8+ T cells is the ratio of testing CD8+ T cells to the target cells.

TABLE 3

| CD8+ T Cell Inhibition Assay (Potency Assay) | | | |
|---|---|---|---|
| Sample ID | Test | Max Inhibition (%) | Max Inhibition (E/T ratio) |
| YRK | 1 | 21.2 | 0.7:1 |
|  | 2 | 26.6 | 0.2:1 |
|  | 3 | 22.5 | 0.7:1 |
| JK | 1 | 18.1 | 0.2:1 |
|  | 2 | 22.4 | 0.2:1 |
|  | 3 | 18.0 | 0.2:1 |
| PR | 1 | 34.7 | 0.7:1 |
|  | 2 | 33.3 | 0.7:1 |
|  | 3 | 35.0 | 0.2:1 |

44

Also see the drawing of the figures of the data for preclinical studies on different indications using the TH1 vs TB1 targets.

F. Release Testing

Release criteria for the intermediate harvested DCs and the final product pDC(H)s have been developed. The harvested DCs were tested for mycoplasma and viability. The pDC(H)s were tested for cell count, immunophenotype, mycoplasma, endotoxin, and sterility cultures in final formulation. Table 4 lists release tests, including release criteria and method.

TABLE 4

| Release testing specifications and testing methods | | | |
|---|---|---|---|
|  | Test | Release Criteria | Method |
| Harvested DC | Mycoplasma Testing | Negative | PCR (Wuxi-Apptec) |
|  | Viability | >70% | Trypan Blue Exclusion |
| pDC | Total DC count | >3.0 × 10^7 | Manual |
|  | Endotoxin Testing | ≤5EU/kg | Endosafe ™ PTS |
|  | Sterility Testing | No Growth | Bac-T Alert 14 day |
|  | Immunophenotyping | >80% | Flow Cytometry |
|  | Total CD11C+ (gated on large cells) |  |  |

Example 3. Stability of pDC(H)s

The final product was stored at ≤−130° C. and used within 12-18 months of manufacture. Studies on short-term and long-term product stability during storage and post-thaw are reported in Tables 5-7. Stability was determined by conducting the potency assay (described above) for functional determine. Cryopreserved therapeutic agent vials containing pDC(H)s were removed from a LN2 freezer, quickly thawed in a ~37° C. water bath and placed immediately on ice. The function of the thawed therapeutic agent (i.e., pDC(H)s) was compared to that of the therapeutic agent at the time of original harvest by leukapheresis. Three-month stability data for the therapeutic agent are summarized in Table 5. The long-term stability data is summarized in Table 6. Since these stability studies were performed on the therapeutic agent generated in the research laboratory, we also performed the same evaluation on the clinical therapeutic agent generated by the manufacturer.

A. Stability After Short-Term Storage

In Table 5, vials of cryopreserved research therapeutic agent were thawed more than three months post-cryopreservation. The potency assay was performed as described above. The Potency Parameter is the % of net inhibition of the CD8(H) lines versus CD8(B) lines from each subject. Based on our experience, the values among different individuals vary from person to person in the range of 10-40%. The % of net inhibition is also known as inhibition index.

TABLE 5

| Short-term stability data | | |
|---|---|---|
| Sample Name | Thaw Points | Potency Parameter |
| SJ1(2T) | Harvest | 31.1% |
| Subject PR | Month 3 | 31.9% |
| SJ1(2T) | Harvest | 31.7% |

TABLE 5-continued

| Short-term stability data | | |
|---|---|---|
| Sample Name | Thaw Points | Potency Parameter |
| Subject BC | Month 3 | 28.5% |
| SJ1(3T) | Harvest | 23.1% |
| Subject ID1 | Month 3 | 26.6% |
| SJ1(3T) | Harvest | 15.8% |
| Subject LM | Month 3 | 15.7% |

B. Stability After Long-Term Storage

In Table 6, vials of cryopreserved research therapeutic agent were thawed more than one year after cryopreservation. The potency assay was performed as described above. The Potency Parameter is the % of net inhibition of the CD8(H) lines versus CD8(B) lines from each subject. From our experience, the values among different individuals vary from person to person in the range of 10-40%. The results showed that the function of the therapeutic agent after 12-18 months freezing remained same.

TABLE 6

| Long-term stability data | | | | | | | |
|---|---|---|---|---|---|---|---|
| | Freshly made THE THERAPEUTIC AGENT | | | THE THERAPEUTIC AGENT thaw after freezing | | | |
| Subject ID | Max Inhibition (%) | Max Inhibition (E/T ratio) | Date Day/ Month/ Year | Max Inhibition (%) | Max Inhibition (E/T ratio) | Date Day/ Month/ Year | Periods (Months) |
| AVR A | 21.6 | 0.2:1 | 06/04/13 | 21.3 | 0.2:1 | 10/28/14 | 16 |
| AVR B | 25.7 | 0.2:1 | 07/11/13 | 37.0 | 0.2:1 | 10/29/14 | 15 |
| AVR C | 19.6 | 0.2:1 | 07/16/13 | 18.4 | 0.2:1 | 10/23/14 | 15 |
| YRK | 22.6 | 0.2:1 | 05/07/12 | 25.8 | 0.7:1 | 10/29/14 | 29 |
| ID1 | 24.6 | 0.2:1 | 05/01/12 | 27.0 | 0.2:1 | 10/15/14 | 29 |
| PR | 33.0 | 0.7:1 | 05/22/12 | 41.1 | 0.2:1 | 10/14/14 | 28 |
| SP | 28.9 | 0.7:1 | 05/01/12 | 24.9 | 0.2:1 | 10/14/14 | 29 |
| Sub 28-2 | 20.2 | 0.2:1 | 02/25/13 | 34.1 | 0.2:1 | 10/16/14 | 20 |

C. Stability at Room Temperature

To ensure product stability from the time of thaw to the time of infusion, potency assays (described above) were conducted to determine the amount of time the product remained functional. As summarized in Table 7, the therapeutic agent remains stable after thaw and up to two (2) hours (i.e., 120 minutes) at room temperature.

In Table 7, the percentage (*%) of cells recovered at different time points after thaw and up to two (2) hours reflects the stability of the therapeutic agent product at room temperature. It is calculated as [(Number of pDC(H)s at different time points/Number of cells at 5 minutes time point]×100%.

TABLE 7

| Stability at room temperature after thaw | | | | | | | | | |
|---|---|---|---|---|---|---|---|---|---|
| | 5 (baseline) | | 30 minutes after thaw | | 60 minutes after thaw | | 90 minutes after thaw | | 120 minutes after thaw | |
| Sample ID | Cell # (×10^4) | %* | Cell # (×10^4) | %* | Cell # (×10^4) | %* | Cell # (×10^4) | %* | Cell # (×10^4) | %* |
| Sample 1 | 6.6 | 100.0 | 5.1 | 84.6 | 5.3 | 81.5 | 6.3 | 96.9 | 7.0 | 107.7 |
| Sample 2 | 8.0 | 100.0 | 10.0 | 125 | 8.0 | 100 | 8.0 | 100 | 9.0 | 112.5 |
| Sample 3 | 2.1 | 100.0 | 2.2 | 104.8 | 2.2 | 104.8 | 2.2 | 104.8 | 2.1 | 100.0 |
| Sample 4 | 2.1 | 100.0 | 1.7 | 81.0 | 2.0 | 95.2 | 2.1 | 100.0 | 1.8 | 85.7 |
| Sample 5 | 1.6 | 100.0 | 1.4 | 87.5 | 1.4 | 87.5 | 1.4 | 87.5 | 1.4 | 87.5 |
| Sample 6 | 7.0 | 100.0 | 8.0 | 114.3 | 9.0 | 128.6 | 6.0 | 85.7 | 7.0 | 100.0 |
| Sample 7 | 5.0 | 100.0 | 4.0 | 80.0 | 5.0 | 100.0 | 5.0 | 100.0 | 4.0 | 80.0 |

Example 4. Manufacturing Validation Studies

In the process of manufacturing pDC(H)s, various samples were collected for QC tests at different stages: initial—leukapheresis product, post Ficoll—collected mononuclear cells, post culture—harvested DCs, and the therapeutic agent—pDC(H)s. For example, the DCs harvested on Day 6 were subject to QC tests, including Flow Cytometry (CD11c/CD86/CD3), Sterility (BAC-T 14), Mycoplasma and Manual Cell Count. The pDC(H)s were subject to QC tests, including Flow Cytometry (CD11c/CD3), Sterility (BAC-T 14), Endotoxin (PTS) and Manual Cell Count. A summary of the validation test results is shown in Table 8. A summary of the releasing test results is shown in Table 9. A summary of the potency test results for the therapeutic agent is shown in Table 10.

TABLE 8

Summary of validation test results

| Parameter | Stage | Validation #1 | Validation #2 | Validation #3 |
|---|---|---|---|---|
| Total TNC processed | Initial | $1.19 \times 10^{10}$ | $5.77 \times 10^9$ | $1 \times 10^9$ |
| TNC post Ficoll | Post Ficoll | $9.81 \times 10^9$ | $4.51 \times 10^9$ | $8.81 \times 10^8$ |
| % Monocytes | Post Ficoll | 24.9% | 25.0% | 21.2% |
| #Monocytes Cultured | Post Ficoll | $3.75 \times 10^8$ | $4.20 \times 10^8$ | $1.88 \times 10^8$ |
| # Viable DCs recovered | Post Culture | $92.6 \times 10^6$ | $67.5 \times 10^6$ | $37.0 \times 10^6$ |
| % monocyte Recovery | Post Culture | 24.7% | 16.1% | 19.6% |
| CD11c (large cell gate) | Post Culture | 99.6% | 99.4% | 96.4% |
| CD11C/CD86++ (large cell gate) | Post Culture | 16.4% | 30.1% | 18.3% |
| CD3 (total gate) | Post Culture | 30.1% | 45.6% | 42.6% |
| # Cells Pulsed | Post Culture | $50 \times 10^6$ | $50 \times 10^6$ | $30.0 \times 10^6$ |
| % THE THERAPEUTIC AGENT recovered | THE THERAPEUTIC AGENT | 80% | 100% | 100% |
| CD11c (large cell gate) | THE THERAPEUTIC AGENT | 99.3% | 99.2% | 99.3% |
| CD11c/CD86++ (large cell gate) | THE THERAPEUTIC AGENT | 14.0% | 30.1% | 22.2% |
| CD3 (total gate) | THE THERAPEUTIC AGENT | 17.5% | 44.8% | 42.6% |

TABLE 9

Summary of release test results

| Parameter | Stage | Validation #1 | Validation #2 | Validation #3 | Release Criteria |
|---|---|---|---|---|---|
| Sterility (14 DAY) | DC Harvest | No Growth | No Growth | No Growth | No Growth |
| Mycoplasma (PCR) | DC Harvest | Pending | Pending | Pending | Negative |
| Sterility (14 DAY) | THE THERAPEUTIC AGENT | No Growth | No Growth | No Growth | No Growth |
| Endotoxin 50 kg patient | THE THERAPEUTIC AGENT | <2EU/kg | <2EU/kg | <2EU/kg | <5EU/kg |
| Flow Cytometry CD11C on large cells | THE THERAPEUTIC AGENT | 99.6% | 99.4% | 99.3% | >80% |

TABLE 10

Summary of potency test results

CD8+ T cell inhibition assay (Potency test)

| Sample ID | Max Inhibition (%) | Max Inhibition (E/T ratio) | Sample ID | Max Inhibition (%) | Max Inhibition (E/T ratio) |
|---|---|---|---|---|---|
| *Day 0 Assay (freshly isolated CD8+ T cells as baseline information) | | | **Day 11 Assay (THE THERAPEUTIC AGENT activated CD8+ T cells from DFCI-CMCF and Avotres, Inc.) | | |

TABLE 10-continued

| Summary of potency test results |
| --- |

| CD8+ T cell inhibition assay (Potency test) |

| Sample ID | Max Inhibition (%) | Max Inhibition (E/T ratio) | Sample ID | Max Inhibition (%) | Max Inhibition (E/T ratio) |
| --- | --- | --- | --- | --- | --- |
| Validation #1 | | | | | |
| Control (CU) | 14.3 | 0.01:1 | Control (CU) | 19.7 | 0.2:1 |
| AVR#1(DF) | 19.2 | 0.04:1 | AVR#1 (DF) | 15.5 | 0.2:1 |
| Validation #2 | | | | | |
| Control (CU) | 28.8 | 0.2:1 | Control (CU) | 38.5 | 0.1:1 |
| AVR#2 (DF) | 24.4 | 0.2:1 | AVR#2 (DF) | 31.7 | 0.1:1 |
| Validation #3 | | | | | |
| Control (CU) | 23.7 | 0.2:1 | Control (CU) | 26.1 | 0.2:1 |
| AVR#3 (DF) | 18.5 | 0.2:1 | AVR#3 (DF) | 23.7 | 0.2:1 |

*In a DO assay, the % of Max Inhibition is calculated as: % of Max Inhibition in the group of the specific target cells loaded with the hHsp60sp peptide - % of Max Inhibition in the group of the control target cells loaded with the B7 peptide.
**In a D11 assay, the % of Max Inhibition is calculated as: % of Max Inhibition in the group of the specific target cells loaded with the hHsp60sp peptide - % of Max Inhibition in the group of the control target cells loaded with the B7 peptide. This value of each group of the CD8+ T cell lines co-cultured with pDC(H)s tested were then normalized by subtracting the value of the control CD8+ T cell lines co-cultured with DCs loaded with B7 peptide.

The above validation runs were all performed at large scale. The goal of these scale-up experiments was to establish that sufficient therapeutic agent could be manufactured from a starting apheresis collection, using the manufacturing process described herein. The results in Table 10 demonstrate the reproducibility of the potency assay in validation runs.

Example 5. HLA-E Restricted CD8+ Treg Specificity Assay Using HLA-E/hHsp60sp Complex Expression Transfectants: TH1 vs TB1

The CD8+ T cell inhibition assay may be used 1) to identify patients who have a defect in the HLA-E restricted CD8+ T cells and determine if the defect can be corrected; 2) to evaluate potency or function of the therapeutic agent; and/or 3) to monitor efficacious duration of the therapeutic agent after treatment.

The potency of the pDC(H)s as a therapeutic agent prepared as described in Example 1-E section was measured by assessing specificity of autologous HLA-E-restricted CD8+ T cell line to the pDC(H)s in a CD8+ T cell inhibition assay D11 assay).

MATERIALS

The following materials were used in the CD8+ T cell inhibition assay to evaluate the potency of the pDC(H)s:
B7sp peptide (VMAPRTVLL, SEQ ID NO: 2): obtained from GeneScript, Corp. Lyophilized powder. Lot No: 399490030913;
hHsp60sp peptide (QMRPVSRVL, SEQ ID NO: 1): obtained from Polypeptide Group. Lyophilized powder. Lot No: 1305013R2
PBS: obtained from Cellgro, Cat #46-013-CM;
RPMI 1640 medium: obtained from Cellgro, Cat #15-041-CV;
PBMC: derived from a donor or patient;
GM-CSF: obtained from Miltenyi Biotec, Cat #170-076-112;

IL-4: obtained from Miltenyi Biotec, Cat #170-076-101;
IL-2: obtained from Peprotech, Cat #200-02;
PFA: obtained from Electron Microscopy Sciences, Cat #15741;
Human CD4 Microbeads: obtained from Miltenyi Biotec, Cat #130-045-101;
Human CD8 Microbeads: obtained from Miltenyi Biotec, Cat #130-045-201;
Lymphocyte Separation Medium: obtained from Cellgro, Cat #25-072-CV;
GMP serum-free DC Medium: obtained from Cellgenix, Cat #20801-0500;
DMSO: obtained from Cellgro, Cat #MT 25950CQC;
Human Albumin 25% USP: obtained from Talecris Bio-therapeutics, NDC #13533-684-16;
Fetal Bovine Serum: obtained from Atlanta Biologics, Cat #S11150;
GENETICIN® Selective Antibiotic (G418 Sulfate): obtained from Gibco, Cat #10131035;
Anti CD86 biotin: obtained from BD Bio Sciences, Cat #555656;
Anti CD11c PE: obtained from BD Bio Sciences, Cat #555392;
Anti-Streptavidin FITC: obtained from BD Bio Sciences, Cat #554060; and
Six well Falcon tissue culture plate: obtained from Corning, Inc., Cat #353046.
The Target Cell Lines Used (TH1 vs TB1)
In this example, the specific target cells were from a cell line with surface expression of an HLA-E/Hsp60sp complex (i.e., HLA-E associated with the hHsp60sp peptide of SEQ ID NO: 1), and the control target cells were from a cell line with surface expression of an HLA-E/B7sp complex (i.e., HLA-E associated with the B7sp peptide of SEQ ID NO: 2).
The target cell lines were generated by routine cloning technology, for example, engineering a fusion construct comprising the HLA-E gene linked a polynucleotide sequence encoding the hHsp60sp peptide or the B7sp peptide through a flexible linker in a suitable vector, transfecting the vector to a B721 cell line and selecting clones having surface expression of the desired HLA-E/Hsp60sp complex, which transfectant is identified as "TH1" below, or HLA-E/B7sp complex, which transfectant is identified as "TB1" below. The fusion construct may also include a fluorescent protein such as GFP or the like as an indicator. It is understood by a person skilled in the art that any linker known by those skill in the art can be used, which may be any short peptide sequence as long as it does not form a secondary structure that interferes with the main structure of the HLA-E/peptide complex. By way an example, a Gly-Ser linker may be used. Typically, the linker between the peptide and the HLA-E may be 10-20 amino acids long.

By way of an example, the peptide-HLA-E fusion construct may be engineered by linking the reading frame of a polynucleotide sequence encoding the hHsp60sp peptide (or B7sp peptide) and HLA-E gene reading frame through a linker, which can be transfected into a B721 cells to generate a cell line having surface expression of an HLA-E/Hsp60sp (or HLA-E/B7sp) complex. For example, the specific target cells were cells expressing an HLA-E/Hsp60sp complex (TH1, specific target) or HLA-EB7sp complex (TB1, control target) on the surface of the cells and deposited with the American Type Culture Collection (ATCC) under the Budapest Treaty having an ATCC Accession No. 127256; and the control target cells were cells expressing an HLA-E/B7sp complex on the surface of the cells and deposited with the ATCC under the Budapest Treaty having an ATCC Accession No. 127257.

The prepared specific target cells and the control target cells were then placed at 26 C.° overnight in the afternoon on −D1 for the D0 assay and D10 for the D11 assay). 0.25 M of the target cells were prepared for each treatment.

PROCEDURES

1. D0: Process the PBMC from the subject
   1). Isolation of CD8+ T cells from a patient or donor's PBMC to obtain CD8+ T cells
   Upon receipt of 60 ml of PBMC from a patient, CD8+ T cells were purified and tested in a D0 (day 0) assay for baseline information. The remaining CD8+ T cells were frozen for generating a CD8+ T cell line with the therapeutic agent after iDCs were harvested from the DC culture on Day 6 as described in Example 1.
   2). Set up a DC culture on D0 which will be harvested to produce pDC(H)s on D6.
   Dendritic cells were derived from PBMC cells and were cultured in 6-well plates with GMP serum-free RPMI, at 37° C., 5% $CO_2$ for 1-1.5 hours. The wells were gently washed. The non-adherent cells were washed away and the adherent cells were then cultured in DC media containing GM-CSF and IL-4 at final concentrations of 80 ng/mL and 20 ng/ml, respectively.
   3). Set up the D0 assay
   The Day 0 Assay is designed to test the function of the isolated CD8 T cells without any in vitro activation by pDC(H)s for the purpose to determine if the testing HLA-E restricted CD8+ Treg cells have a defect in inhibiting proliferation of target cells. Table 11 shows cultures of CD8+ T cells, including testing CD8+ T cells (XX) and control CD8+ T cells from a healthy individual (YY), and targets, including TH1 and TB1, at different ratios in plate 1 for the Day 0 (D0) Assay.

(1). Cells prepared:
   a. CD8+ T cells, including freshly isolated or thawed from frozen CD8+ T cells from the testing subject and normal healthy individual as system control, and b. targets, including TH1 and TB1 which were placed at 26 C.° overnight in the afternoon before D0 for the D0 assay and in the afternoon of D10 for the D11 assay). 0.25 M of the target cells were prepared for each treatment.

(2). Step.1: 0.26 million of freshly isolated CD8+ T cells or 2.6M of the PBMC having a 10% CD8+ T cells are obtained. Testing CD8+ T cells, also referred to as testing effector cells, are prepared in 0.8 ml for two sets of targets (TH vs TB) and plated at 0.4 ml/well×2 wells as one test. The testing effector cells are subject to limiting dilution: 0.3 mL of the medium plated into Well 1-5 of each row and 0.4 ml of the testing effector cells were added to each row of last well (well 6) with no additional medium.

0.1 mL of the CD8+ T cell suspension from the last well is added to next well to dilute (¼ dilution), except for well 1, which is served as control without the CD8+ T cells.

In the last well, 0.13 million of CD8 cells×75%=0.1 million/well are added so that the highest E/T ratio were 0.1/0.0375=2.7.

0.26 Million×1 lines=0.26 million/patient in 0.8 ml were needed.

(3). Step 2:0.25 million of the specific target cells (TH1) and the control target cells (TB1) are mixed with 0.25 million of unloaded B721 in 2 ml of complete RPMI 1640 to make a mixture. The mixture is placed into a 6 wells/row plate at 0.3 ml/well with a target concentration of 0.125M/ml×0.3 ml=0.0375 million/well.

TABLE 11

| Plate 1 design for D0 assay | | | | | | |
|---|---|---|---|---|---|---|
| Targets | 0:1 | 0.01:1 | 0.04:1 | 0.17:1 | 0.68:1 | 2.7:1 |
| | | | | XX | | |
| TB1 | 1 | 2 | 3 | 4 | 5 | 6 |
| TH1 | 7 | 8 | 9 | 10 | 11 | 12 |
| | | | | YY | | |
| TB1 | 13 | 14 | 15 | 16 | 17 | 18 |
| TH1 | 19 | 20 | 21 | 22 | 23 | 24 |

Plate 1 is incubated at 37° C., 5% $CO_2$ for 5-7 days (D5-D7).

(4). Analysis by FACS

The effect of the testing CD8+ T cells on the target cells was determined by calculating the ratio between the two types of target cells. In particular, the ratio between TH/B721 or TB/B721 cells in the presence or absence of the testing CD8+ T cells was determined as % of specific inhibition (potency):

{[the ratio of TH or TB versus B721 cells in control cultures(without CD8+ T cells)minus the ratio in experimental cultures(with CD8+ T cells)]/ the ratio in control cultures}×100%.

2. D6: Generation pDC(H) and pDC(B) lines to set up the CD8(H) and CD8(B) lines
   1). Harvest the DCs, loading the peptide/s to generate pDC(H) and pDC(B) lines:
   The DCs harvested on D6 were loaded with the hHsp60sp peptide to make the therapeutic agent pDC(H)s, or loaded with the B7sp peptide as a control, at 50 μM, 37° C. for 2 hours. The peptide loaded DCs were fixed with 2% of PFA for generating CD8+ T cell lines. The remaining peptide loaded DCs were aliquoted and frozen in liquid nitrogen for future use.

2) Set up the CD8(H) and CD8(B) cell lines:

The CD8+ T cell lines were generated by co-culturing $1.5$-$2\times10^6$ of isolated autologous CD8+ cells (thawed from the vials frozen on D0) with $0.2$-$0.3\times10^6$ of the therapeutic agent, i.e., autologous DCs loaded with hHsp60sp, pDC(H), or a control, i.e., autologous DCs loaded with B7sp, pDC (B)s, in 1 mL in 48 well plate to set up the lines of CD8(H), activated by the therapeutic agent pDC(H), or CD8(B) (activated by the control agent pDC(B), then add IL-2 in an amount commonly used by those skilled in the art, on the second day. The CD8(H) and CD8(B) cells were culture for another 5 days and harvested on D11 to be tested with known CD8+ T cells from normal healthy people as a positive control.

3. D11: Harvested the CD8(H) and CD8(B) lines on their D5 cultures and set up the D-11 assay.

1). Harvested the CD8(H) and CD8(B) lines and plated into a 48-well plate with a graded number for a graded E/T ratio.

2). Preparation of target cells: The target essentially expressing a complex of HLA-E/hHsp60sp (TH1) or HLA-E/B7sp (TB1) and a GFP protein on their surface by transfecting B721 cells with genes encoding a fusion protein and a GFP gene. Cell lines expressing a complex of HLA-E/hHsp60sp (H cells) or HLA-E/B7sp (B cells) as a control line, can also be prepared in various forms, for example, targets expressing a complex of HLA-E/hHsp60sp or HLA-E/B7sp by loading B721/E cell line with an hHsp60sp or a control peptide B7sp (see example 6 below)

3). Set up for Day 11 Assay: The Day 11 Assay was designed to test if the defect of the CD8+ Treg cells as determined in the D0 assay could be corrected by the therapeutic agent pDC(H)s. Table 12 shows cultures of CD8+ T cells triggered with pDC(H) ex-vivo, or pDC(B) as control, including CD8(H), CD8(Hf), CD8(Bf) and CD8+ T cells from a healthy individual, and targets, including TH1 (mixed with B721) and TB1 (Mixed with B721), at different ratios in plate 2 for the Day 11 Assay.

Plating of the testing CD8(H) or CD8(B) lines:

The medium was added at 0.3 mL/well into well 1-5 in each row and the testing CD8+ T cells were already plated as described above.

0.26 million CD8(H) or CD8(B) cells were suspended in 0.8 ml culture medium. These two effector lines were for one set of targets, TH and TB. TH is specific target cell line. TB is target control cells.

0.4 mL of CD8 was added to each of last well (well 6), and 0.1 mL to next well to dilute (1/4 dilution). In the last well, 0.13 million×75%=0.1 million/well, so the highest E/T ratio was 0.1/0.0375=2.7. A total of 0.26 million/lines in 0.8 ml for each patient are needed.

The same procedure of adding the targets as for the D0 assay was repeated.

TABLE 12

| Plate 2 design for D11 assay | | | | | | |
|---|---|---|---|---|---|---|
| B721/E Cells loaded with | 0:1 | 0.01:1 | 0.04:1 | 0.17:1 | 0.68:1 | 2.7:1 |
| *CD8(H) | | | | | | |
| TB1 | 1 | 2 | 3 | 4 | 5 | 6 |
| TH1 | 7 | 8 | 9 | 10 | 11 | 12 |
| **CD8(Hf) | | | | | | |
| TB1 | 13 | 14 | 15 | 16 | 17 | 18 |
| TH1 | 19 | 20 | 21 | 22 | 23 | 24 |
| ***CD8(Bf) | | | | | | |
| TB1 | 25 | 26 | 27 | 28 | 29 | 30 |
| TH1 | 31 | 32 | 33 | 34 | 35 | 36 |
| ****System Control: Testing CD8+ T cells from normal healthy individual | | | | | | |
| TB1 | 37 | 38 | 39 | 40 | 41 | 42 |
| TH1 | 43 | 44 | 45 | 46 | 47 | 48 |

*CD8(H): CD8+ T cell lines generated by co-culturing the CD8+ T cells with hHsp60sp loaded DCs.
**CD8(Hf): CD8+ T cell lines generated by the CD8+ T cells co-cultured with hHsp60sp loaded and PFA fixed DCs.
***CD8(Bf): CD8+ T cell lines generated by the CD8+ T cells co-cultured with hB7sp loaded and PFA fixed DC.
****Testing CD8+ T cells from normal healthy individual as in the D0 assay.

Plate 2 was incubated at 37° C., 5% $CO_2$ for 5-6 days, and then analyze by FACS as described above.

Acceptance Criteria

A patient suffering from an autoimmune disease such as type 1 diabetes (T1D) may be treated with the therapeutic agent pDC(H)s according to the present invention if the patient has defective CD8+ T cells identified by the screening assay (D0 assay) and the defect was corrected by the therapeutic agent ex vivo (D11 assay) as described herein.

In the D0 assay, the percentage of the maximum inhibition (Inhibition Index) is calculated as the percentage of the maximum inhibition in the group of the target TH minus the percentage of the maximum inhibition in the group of the target TB (Inhibition Index). A "Inhibition Index" value of <50% of the testing group compared to the Inhibition Index value of the normal healthy control group as Acceptance Criteria for identifying a defect of the testing CD8+ T cells; whereas in the D11 assay, a "Inhibition Index" value of >50% of the testing group compared to the Inhibition Index value of the normal healthy control group as Acceptance Criteria for correction of the defect of the testing CD8+ T cells.

Example 6. HLA-E Restricted CD8+ Treg Specificity Assay Using HLA-E Expression Transfectants Loaded with hHsp60sp or B7sp The potency of the pDC(H)s as a therapeutic agent prepared as described in Example 1-E section was also measured by assessing specificity of autologous HLA-E-restricted CD8+ T cell line to the pDC(H)s in a CD8+ T cell inhibition assay using HLA-E expression transfectants.

The HLA-E expression transfectants (B721/E) were generated for use in the CD8+ T cell specificity assay in contrast to the HLA-E/Hsp60sp complex transfectants used in Example 5. HLA-E fusion construct (pDsRed) was engineered by RT-PCR from the human B cell line B721 using the following primers: CCAAGCTTATGGTAGATG-GAACCCTCCTTT (SEQ ID: 3) (forward) and GGGGATC-CAACAAGCTGTGAGACTCAGACCC (SEQ ID: 4) (reverse). Amplified clones in pCR2.1 were fully sequenced.

Six independent full-length clones representing the HLA-E 101 haplotype but lacking the 3' termination codon were subcloned into the mammalian expression vector pDsRed-Express-N1 (Clontech Laboratories Inc.), yielding a single open reading frame encoding a fusion protein consisting of HLA-E joined to a variant of the Discosoma species red fluorescent protein (Clontech Laboratories Inc.). The pDsRed-HLA-E construct was introduced into the HLA class I-deficient B cell line B721 by electroporation, and stable clones were selected by subcloning in Geneticin (G418).

The surface expression of HLA-E on B721 cells transfected with HLA-E (B721/E) was tested by exogenously loading the cells with the hHsp60sp peptide, the B7sp peptide, or a control non-HLA-E-binding peptide at 26° C. for 18 hours. The cells were then washed, stained with anti-HLA-E mAb 3D-12 followed by Fl-goat anti-mouse Ig, and analyzed on a FACS can flow cytometer and by Cell Quest software (BD). mAb 4D-12 served as control. Any other anti-HLA-E mAb antibodies may serve the purpose described herein and can be made by a person skilled in the art via routine experimentation.

To perform the CD8+ T cell specificity assay, freshly isolated CD8+ T cells were purified from PBMCs, and CD8(H) and CD8(B) lines were generated as described in Example 5. HLA-E-transfected cells (B721/E) served as targets were passively loaded with specific peptides—the hHsp60sp peptide and the B7sp peptide, and control non-HLA-E-binding peptide—overnight at 26° C. Equal numbers of unlabeled B721/E cells loaded with a peptide and CFSE labeled parental B721 cells that were not loaded with the peptide were mixed, and testing CD8+ T cells were added to the targets at graded E/T ratios, from 3:1 to 0.005:1. The specificity of the freshly isolated CD8+ T cells was studied by comparing their inhibition of target B721/E cells loaded with the hHsp60sp peptide versus those loaded with the B7sp peptide or other control peptide/s. In addition, the specificity of the CD8(H) line was compared with that of the control CD8(B) line. In this regard, the CD8(H) cells established from normal healthy control subject/s tested had no effect on B721 cells alone or B721 cells pulsed with B7sp peptide or other control peptide/s, indicating that the normal CD8+ T cells had no effect on these control cell lines. On day 5-6, the cell mixtures were assessed by FACS analysis, in which the CD8+ T cells were gated out during the analysis. The ratio between the two types of targets was calculated and compared in the presence or absence of the CD8+ T cells to evaluate the effect of testing CD8+ T cells on the targets. The percent of specific inhibition was calculated as: {[ratio of loaded B721/E versus unloaded B721 cells in control cultures (without CD8+ T cells)—ratio in experimental cultures (with CD8+ T cells)]/ratio in control cultures}×100. Statistical analysis by 2-tailed Student's t test of the highest percentage of the inhibition (Inhibition Index) was used to evaluate significant differences among different groups (P<0.05).

Intracellular CEs secreted by the CD8+ T cells was detected. The CD8(H) and CD8(B) lines were generated from healthy individuals as described. The established HLA-E-transfected cells (B721/E) served as targets to trigger the CD8+ T cells and were passively loaded with hHsp60sp peptide overnight at 26° C., and the B7sp peptide served as control. Testing CD8(H) and CD8(B) cells were added to the target B721/E cells loaded with different peptides at graded E/T ratios, from 3:1 to 0.005:1. At different time points, 3-color intracellular staining was performed on the cell mixture with anti-perforin-PE, anti-granzyme A-FITC, and anti-granzyme B-Bio/Cy following the manufacturer's instructions (BD). The cells were assessed by FACS analysis, in which the CD8+ T cells were gated in during the analysis. The CE expression index was calculated as a function of different E/T ratios: ([% of double positive CE-stained CD8+ T cells from different E/T ratio cultures]−[% of double-positive CE-stained CD8+ T cells from the CD8+ T cells that were not triggered by the target cells])/% of double-positive CE-stained CD8+ T cells from the CD8+ T cells that were not triggered by the target cells.

Example 7. Double-Blind, Randomized Study of Safety, Tolerability and Efficacy of the Cell-Based Therapy in Patients with Type 1 Diabetes This is an ongoing double-blind, randomized, placebo-controlled study to evaluate the safety, tolerability and efficacy to assess the therapeutic agent for type 1 diabetes (T1D). The study includes 25 new-onset T1D subjects who have been identified as having: (a) a defect in HLA-E-restricted CD8+ T cell function associated with pancreatic β cell destruction; and (b) evidence that this defect of HLA-E-restricted CD8+ T cells can be corrected by in vitro treatment of pDC(H) of the inventive procedure set forth in the present application at, for example, Example 5.

Nature of the active ingredient (also known as Therapeutic Agent): The Therapeutic Agent [pDC(H)s] is an individualized preparation of the autologous immature dendritic cells from the patients' adherent primary monocytes cultured with GM-CSF and IL-4 for 6 days, and loaded passively with the hHsp60sp peptide (SEQ ID NO: 1) in vitro and fixed with 2% paraformaldehyde; suspended for intravenous infusion. Preparation of the dosage form for intravenous infusion: The therapeutic agent is cryopreserved in infusible cryomedia in cryopreservation 20 mL bags. Each infusion bag contains between $7 \times 10^6$ and $10 \times 10^6$ cells, 2 mL DMSO, 10 mL of 25% HSA and 8 mL of PLASMA-LYTE® A. Three (3) infusion bags were prepared for each patient. The manufacturing process of the therapeutic agent is described in the present application in great details in, for example, Example 1.

Route of administration: The infusions are administered intravenously.

Frequency of administration: Three (3) infusions are administered to the patients approximately at least 21 days apart, preferably 30 (+/−7) days apart.

Methodology

Each subject is randomized to one of two groups:

Therapeutic group: 16 subjects to receive the therapeutic agent, through i.v. administration.

Placebo control: 9 subjects to receive placebo infusion solution (saline and DMSO) only through i.v. administration.

Duration of the study:

There are three pre-defined periods in this study: screening, treatment and post-treatment follow-up.

Subjects positive for a CD8+ T cell defect correctable in vitro by co-culturing with immature dendritic cells loaded with the hHsp60sp peptide (SEQ ID NO: 1) were identified by HLA-E restricted CD8+ Treg specificity assay.

Screening and cell collection period lasted up to 2 months.

Treatment period consisted of three doses, each ~30 days apart (Baseline, Month 1, Month 2) and a 1-month post-last dose assessment period (through Month 3). Thus, the treatment period is defined to be 3 months in duration.

Post-treatment follow-up period extended approximately 21 additional months (and thus through month 24 of the study, and another 24 months follow up).

Patients are treated with three consecutive doses, administered with 30 days (+/−7 days) intervals between the doses. The primary time point for assessment and statistical analysis was 3 months post-last dose (Month 5), with longer-term follow-up through 22 months post-last dose (month 24).

Efficacy (Endpoints):

The objectives focus on assessing treatment safety, the CD8+ T-cell regulatory system and therapeutic outcomes associated with T1D. The pharmacodynamic effects of the therapeutic agent are assessed over the course of the study period.

The endpoints include:

(a) Assessment of the HLA-E-restricted CD8+ T cell regulatory activity ("potency assay")

(b) Changes from baseline in the area under the curve (AUC) of the stimulated C-peptide levels over a 4-hour mixed meal tolerance test (MMTT)

(c) Changes from baseline in HbA1c (d) Change from baseline in insulin usage (e) Changes from baseline in autoantibody levels The objectives of this study include assessment of changes in pharmacodynamic markers, for example, correcting the function in the HLA-E restricted CD8+ Treg pathway, and improvements of C-peptide levels, HbA1c and antibody values, as well as Insulin daily usage. The sample size of 16 subjects treated with the therapeutic agent and 9 subjects treated with placebo provides estimates of the mean and standard deviation of the treatment benefit of the therapeutic agent as compared to placebo in these endpoints.

Table 13 summarizes the efficacious effects of the therapeutic agent of fixed pDC (pDC(H)), using C-peptide level as a readout, measured up to 150 days, of all 25 subjects (Treated group ×16 vs Placebo group ×9) after the administration of the therapeutic agent on D1. The results showed that after 3 months post treatment, the difference between the C-peptide AUC mean value of pDC(H) treated group and that of the placebo group was statistically significant: P=0.0145, demonstrating that the dosing regimen of the therapeutic preparation was efficacious on the treated T1D subjects.

Table 14 shows the effectiveness of the treatment on the correction of the defect of the dysfunctional HLA-E restricted CD8+ Treg pathway, followed by promising clinical efficacy. Among the first 8 subjects treated with pDC(H) where we have data beyond d150, nearly 40% of them were corrected with their dysfunctional HLA-E restricted CD8+ Treg pathway. Among the remaining 60% who were not corrected, 25% of them had very low baseline C-peptide and longer time from diagnosis before they were treated. We thus estimate that if the recipients all started treatment earlier after diagnosis with better starting conditions, the percentage of correction of the defective HLA-E restricted CD8+ Treg pathway may reach >75%.

TABLE 13

The Total C-peptide AUC level in nmol/L (4 hr MMTT) in Treatment (×16) vs. Placebo (×9) at Day 1 and Day 150 after pDC(H) treatment-sorted by % difference at d150

| Treatment | Patient ID | Age | TFD | C-peptide | | |
|---|---|---|---|---|---|---|
| | | | | D1 | D150 | % Diff |
| *pDC (H) | T1D-0101-022 | 39 | 6.83 | 0.57 | 0.9 | 59.3 |
| pDC(H) | T1D-0101-002 | 29 | 3.55 | 0.69 | 1.05 | 51.6 |
| pDC(H) | T1D-0101-031 | 21 | 4.21 | 0.75 | 0.85 | 13.6 |
| pDC(H) | T1D-0101-001 | 20 | 6.77 | 0.47 | 0.49 | 5.7 |
| pDC(H) | T1D-0101-012 | 37 | 8.28 | 1.63 | 1.68 | 3.5 |
| pDC(H) | T1D-0101-027 | 17 | 7.59 | 0.43 | 0.43 | −0.9 |
| pDC(H) | T1D-0101-028 | 17 | 6.28 | 0.6 | 0.58 | −2.3 |
| pDC(H) | T1D-0101-017 | 24 | 9.89 | 0.59 | 0.51 | −14.6 |
| pDC(H) | T1D-0101-006 | 28 | 10.64 | 0.55 | 0.44 | −20 |
| pDC(H) | T1D-0101-011 | 19 | 7.98 | 0.15 | 0.11 | −28 |
| pDC(H) | T1D-0101-029 | 32 | 10.41 | 0.04 | 0.03 | −28.6 |
| pDC(H) | T1D-0101-005 | 20 | 3.61 | 0.39 | 0.26 | −33 |
| pDC(H) | T1D-0101-009 | 23 | 11.4 | 0.22 | 0.14 | −37 |
| pDC(H) | T1D-0101-034 | 48 | 9.43 | 0.76 | 0.45 | −41.1 |
| pDC(H) | T1D-0101-013 | 19 | 7.03 | 0.49 | 0.27 | −44.2 |
| pDC(H) | T1D-0101-023 | 31 | 11.99 | 0.2 | 0.11 | −45 |
| pDC(H) | Mean ×16 D150 | 26.5 | 7.9 | 0.53 | 0.52 | −10.1 |
| Placebo | T1D-0101-004 | 33 | 6.31 | 0.42 | 0.45 | 6.8 |
| Placebo | T1D-0101-024 | 24 | 9.66 | 0.66 | 0.64 | −4.1 |
| Placebo | T1D-0101-033 | 24 | 7.2 | 0.46 | 0.4 | −13.8 |
| Placebo | T1D-0101-030 | 35 | 6.93 | 0.9 | 0.71 | −20.5 |
| Placebo | T1D-0101-016 | 26 | 9.23 | 0.4 | 0.31 | −23 |
| Placebo | T1D-0101-015 | 33 | 7 | 0.65 | 0.49 | −24.4 |
| Placebo | T1D-0101-003 | 23 | 11.01 | 0.52 | 0.39 | −25.2 |
| Placebo | T1D-0101-025 | 16 | 11.33 | 0.85 | 0.52 | −38.5 |

TABLE 13-continued

The Total C-peptide AUC level in nmol/L (4 hr MMTT) in Treatment (×16) vs. Placebo (×9) at Day 1 and Day 150 after pDC(H) treatment-sorted by % difference at d150

| | | | | C-peptide | | |
|---|---|---|---|---|---|---|
| Treatment | Patient ID | Age | TFD | D1 | D150 | % Diff |
| Placebo | T1D-0101-008 | 22 | 10.74 | 0.64 | 0.34 | −46.4 |
| Placebo | Mean ×9 D150 | 26.2 | 8.8 | 0.61 | 0.47 | −21 |
| | | | | | | P = 0.0145 |

*TFD: Time from diagnosis to the first dose of treatment.
*pDC(H)-dendritic cell loaded with hHSP60sp and fixed with paraformaldehyde (PFA).
Baseline (measured right before the $1^{st}$ dose), prior to the treatment;
D1-the day of the first dosing.
D150 (Visit-7)-Five months post the first dosing, primary readout.
The primary analysis was performed after the last subject completes the D150 (Visit-7) study visit.
P value based on prespecified Mixed effect Model for Repeated Measures (MMRM)
A final analysis will be performed after the last subject completes the D720 (Visit-11) study visit.
The primary analysis was performed after the last subject completes the D150 (Visit-7) study visit.

TABLE 14

The effectiveness of treatment with pDC(H) on correction of defect in the HLA-E restricted CD8+ Treg pathway

| 1. | Among the 8 treated patients treated beyond 150 days, the assay showed (+) in subject #2, #6 and #12, indicating the dysfunction of the HLA-E restricted CD8+ Treg pathway are well corrected, these three can be identified as good responders to the treatment (3/8 = 37.5%). |
|---|---|
| 2. | Subject #1, Assay showed (-) from Visit-6 to Visit-11, may be a non-responder (1/8 =12.5%); |
| 3. | Subject #5, Assay showed a transient positive sign at Visit-7 to Visit-8 and back to (–) from Visit-9 to Visit-11, seemed to be a non-responder (1/8 = 12.5%); |
| 4. | Subject #9 (TFD: 11.4 months and low C-peptide: 0.22 at starting point) only had some positive sign at Visit-8, behaves like a very low responder (1/8 = 12.5%); |
| 5. | Subject #11 (Low C-peptide: 0.15 and high daily Insulin 0.75 at starting point), had some positive sign at Visti-6 to Visit-8, behaves like a very low responder (1/8 = 12.5%); |
| 6. | Subject #13 seemed to be a slow responder. Correction started at Visit-7 on D150 time point and lasted to Visit-9 on D360 time point and we do not have the information on this subject beyond D360 yet. May need longer time to identify the responsiveness of this subject (1/8 = 12.5%). |

Summary

If the recipients were all started early of the treatment with better starting conditions, the % of the effectiveness on correction of the defect of HLA-E restricted CD8+ Treg pathway by treatment may reach >75%.
About the time course of the correction: the relatively precise and general trend and time range need to have more completed data to evaluate.

D1 (Visit-3) - the day of the first dosing;
D150 (Visit-7) - five months post the first dose;
D360 (Visit 9) - one year post the first dose;
D540 (Visit-10) - one year and half post the first dose;
D720 (Visit-11) - two years post the first dose.

In general, the clinical efficacy profiles on the pDC(H) of the first 8 treated subjects at their D360-D720 time points basically fall into the "range", the "scope" and the "pattern" of, and are consistent with, the effectiveness of the treatment by AVT001 on the correction of the defect of the dysfunctional HLA-E restricted CD8+ Treg pathway (Tables 13-14). Our observations strongly support the notion that correction of the dysfunctional HLA-E restricted CD8+ Treg pathway, as a primary root cause of T1D, will lead to promising clinical efficacy. Particularly, the clinical efficacy profiles on the pDC(H) treatment of total 25 subjects (Tx16 and Px9) at their D150 time point showed impressive and promising clinical results (Table 13).

Therapy by administration of pDC(H) is to target the common root cause of a variety of autoimmune diseases, including T1D, by stopping self-destruction by the patients' own immune system for potential cure and prevention of autoimmune diseases. Efficacy will be optimal if the patients are diagnosed and receive the treatment at a stage where the damage to their diseased organ/tissues is reversible. However, for those patients at later disease stages, this therapy could serve as a necessary therapy to combine with currently available treatments that target disease symptoms, or to combine with stem cell transplantation therapy to replace the diseased organs. In the latter case, even when the stem cell transplantation is successfully accomplished, the replaced tissue/organ will be destroyed again by their own immune system if the defect of HLA-E restricted CD8+ Treg pathway, the common root cause, is not corrected by the pDC(H) therapy.

Example 8. Treatment of Multiple Sclerosis

Figure 1B:
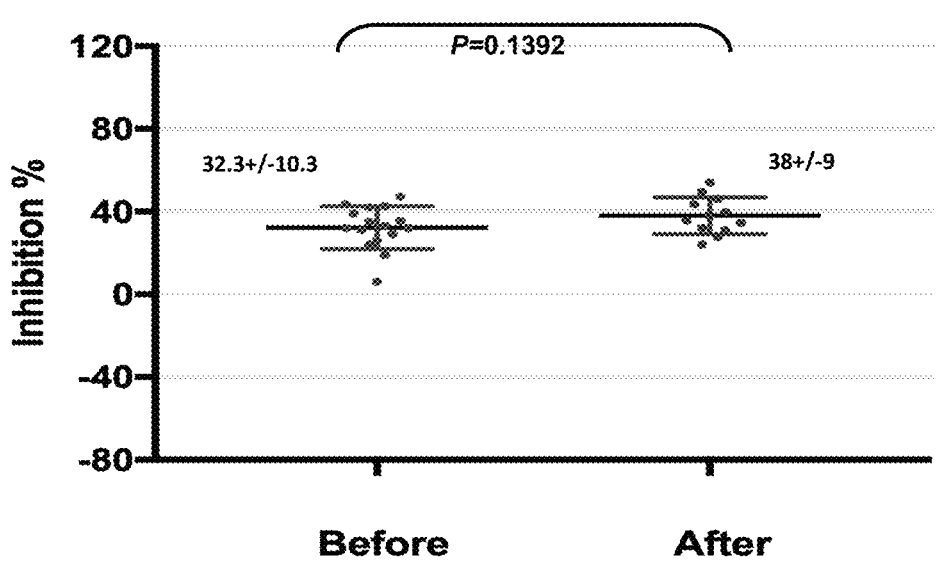
Figure 1C:
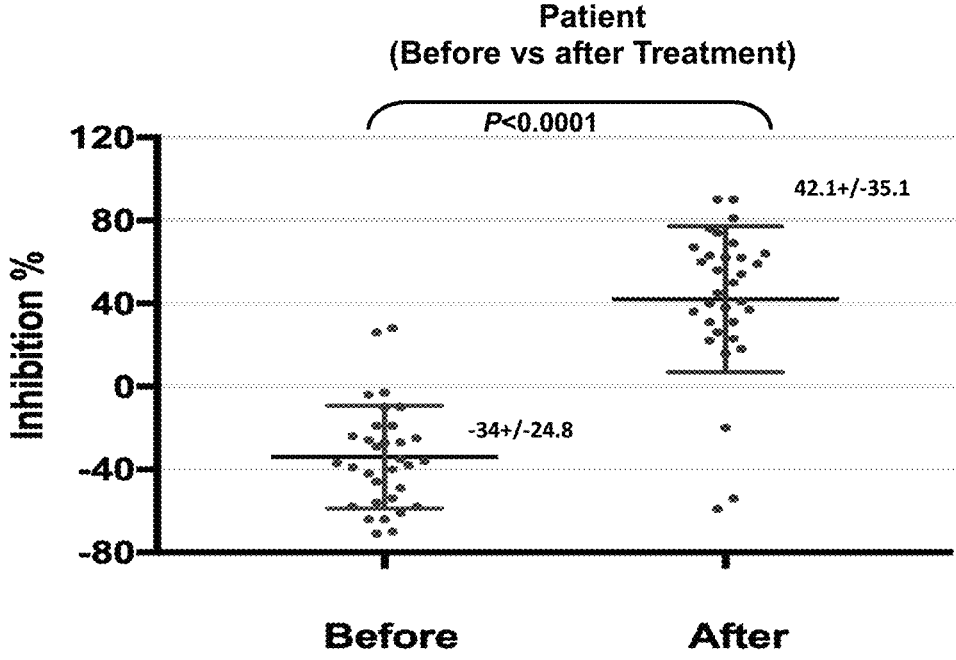

It has been found that patients suffering from the autoimmune diseases namely multiple sclerosis (MS), including relapsing-remitting multiple sclerosis (RRMS) and secondary-progressive multiple sclerosis (SPMS), and primary-progressive multiple sclerosis (PPMS) have the same correctable defect of HLA-E restricted CD8+ Treg cells as that in the patients suffering from T1D as shown in FIG. 1, which demonstrates that the defect can be corrected ex-vivo by the same therapeutic composition of the present invention in the same way as used for the T1D patients as described in this application.

Accordingly, the same therapeutic composition may be administered to treat the MS patients with the same dosing regimen as used to treat T1D in Example 7 or a different regiment that is to be adjusted by a person of ordinary skill in the art depending on the patient's physiological conditions, age, gender or prognosis of the autoimmune disease.

Example 9. Treatment of Psoriasis

Figure 2A:
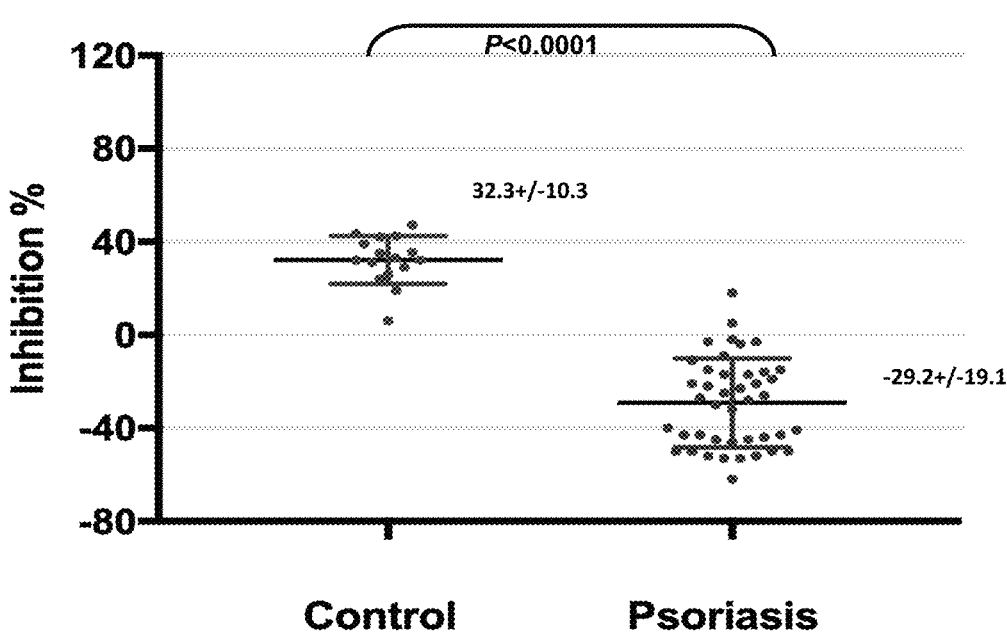
FIGS. 2A-2C show results from a CD8+ Treg cell specificity assay as set forth in Example 9. The CD8+ Treg cells from psoriasis patients were functionally defective when compared with the normal functional CD8+ Treg cells from healthy individuals prior to treatment with the therapeutic agent of the present invention, whereas the function of the defective CD8+ Treg cells from the psoriasis patients was corrected or restored after the treatment. A. BEFORE therapy, the readings between "normal" (N=16) and "Psoriasis patients" (N=42) are statistically significant, P<0.0001. B. The "control" group showed normal pathway function BEFORE therapy (N=16), and statistically non-distinguishable AFTER therapy (N=12), P=0.1392. C. The "patient" group (N=42) showed defective pathway function BEFORE therapy, and the defect was corrected AFTER therapy, showing statistically significant on the effect of the treatment, P<0.0001.
Figure 2B:
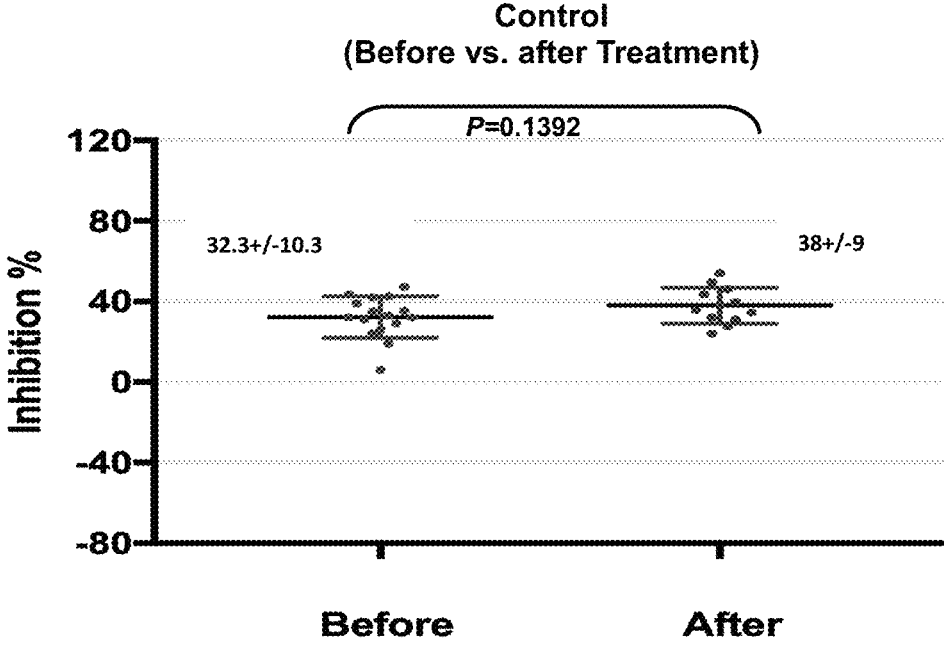
Figure 2C:
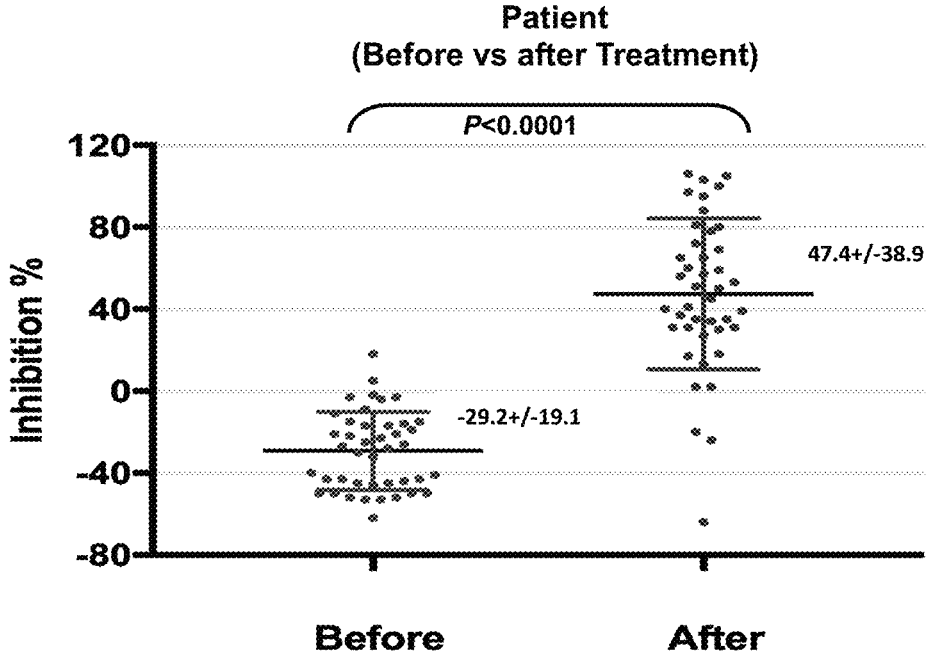

It has been found that patients suffering from the auto-immune diseases namely psoriasis (with and without psori-atic arthritis) have the same correctable defect of HLA-E restricted CD8+ Treg cells as that in the patients suffering from T1D as shown in FIG. 2, which demonstrates that the defect can be corrected ex-vivo by the same therapeutic composition of the present invention in the same way as used to correct the defect of CD8+ Treg cells in the T1D patients, which is described in this application in great details.

Accordingly, the same therapeutic composition may be administered to treat the psoriasis patients with the same dosing regimen as used to treat T1D in Example 7 or a different regimen that is to be adjusted by a person of ordinary skill in the art depending on the patient's physi-ological conditions, age, gender or prognosis of the auto-immune disease.

Example 10. Treatment of Rheumatoid Arthritis

Figure 3A:
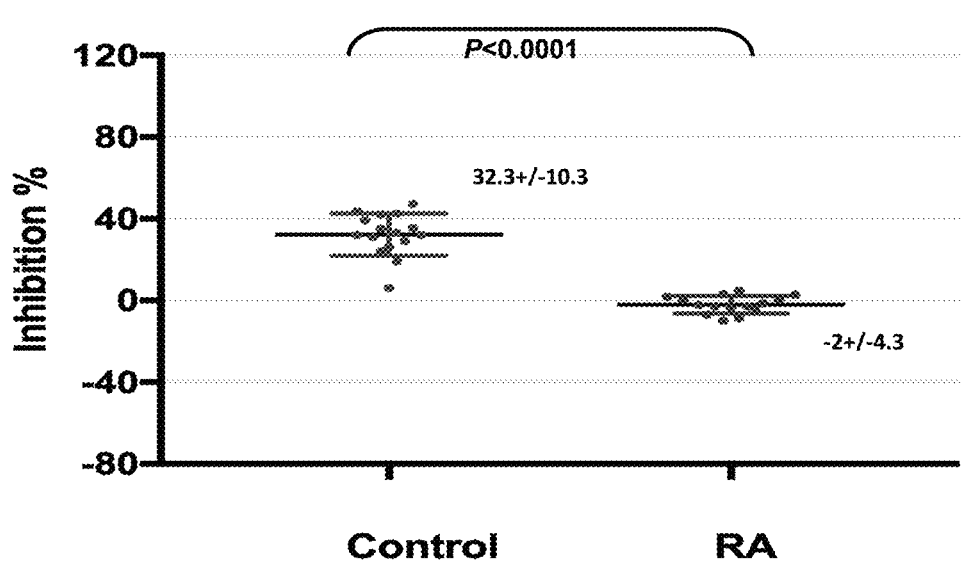
FIGS. 3A-3C show results from a CD8+ Treg cell specificity assay as set forth in Example 10. The CD8+ Treg cells from rheumatoid arthritis (RA) patients are functionally defective when compared with the normal functional CD8+ Treg cells from healthy individuals prior to treatment with the therapeutic agent of the present invention, whereas the function of the defective CD8+ Treg cells from the RA patients was corrected or restored after the treatment. A. BEFORE therapy, the readings between "normal" (N=16) and "RA" patients" (N=15) are statistically significant, P<0.0001. B. The "control" group showed normal pathway function BEFORE therapy (N=16), and statistically non-distinguishable AFTER therapy (N=12), P=0.1392. C. The "patient" group (N=15) showed defective pathway function BEFORE therapy, and the defect was corrected AFTER therapy, showing statistically significant on the effect of the treatment, P<0.0001.
Figure 3B:
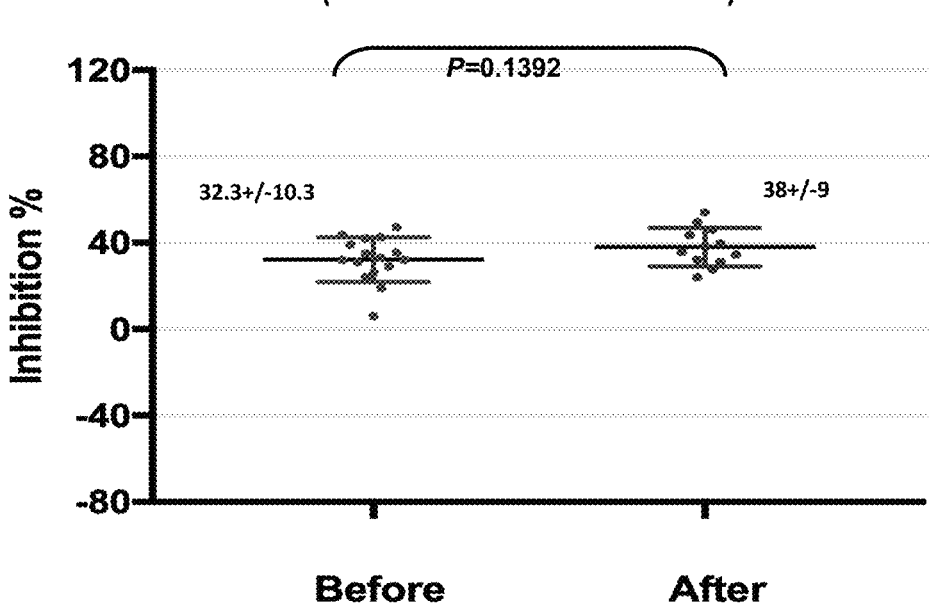
Figure 3C:
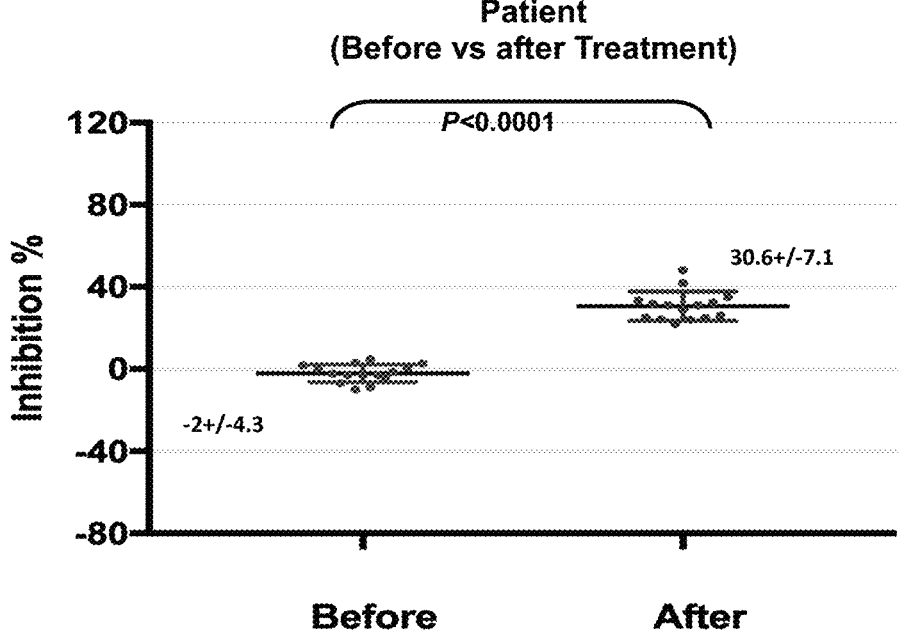

It has been found that patients suffering from the auto-immune diseases namely rheumatoid arthritis (RA) have the same correctable defect of HLA-E restricted CD8+ Treg cells as that in the patients suffering from T1D as shown in FIG. 3, which demonstrates that the defect can be corrected ex-vivo by the same therapeutic composition of the present invention in the same way as used for the T1D patients as described in this application.

Accordingly, the same therapeutic composition may be administered to treat the RA patients with the same dosing regimen as used to treat T1D in Example 7 or a different regimen that is to be adjusted by a person of ordinary skill in the art, depending on the patient's physiological condi-tions, age, gender or prognosis of the autoimmune disease.

Example 11. Treatment of Lupus

Figure 4A:
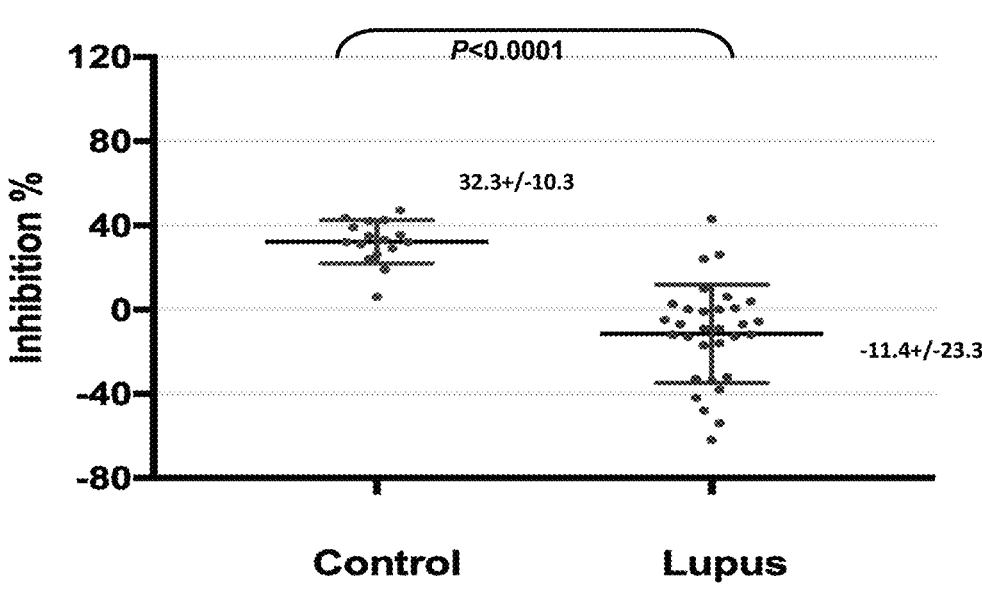
FIGS. 4A-4C show results from a CD8+ Treg cell specificity assay as set forth in Example 11. The CD8+ Treg cells from lupus patients are functionally defective when compared with the normal functional CD8+ Treg cells from healthy individuals prior to treatment with the therapeutic agent of the present invention, whereas the function of the defective CD8+ Treg cells from the lupus patients was corrected or restored after the treatment. A. BEFORE therapy, the readings between "normal" (N=16) and "lupus patients" (*N=31) are statistically significant, P<0.0001. B. The "control" group showed normal pathway function BEFORE therapy (N=16), and statistically non-distinguishable AFTER therapy (N=12), P=0.1392. C. The "patient" group (N=31) showed defective pathway function BEFORE therapy, and the defect was corrected AFTER therapy, showing statistically significant on the effect of the treatment, P<0.0001.
Figure 4B:
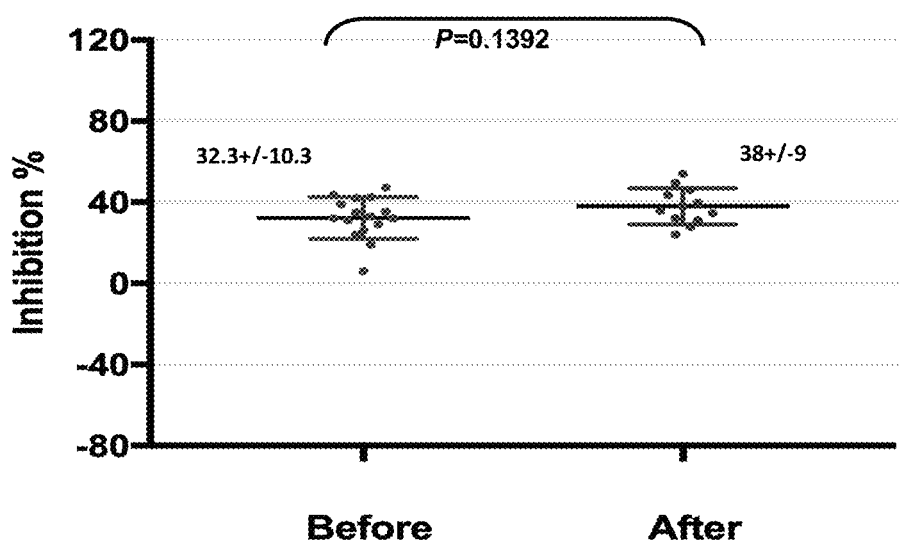
Figure 4C:
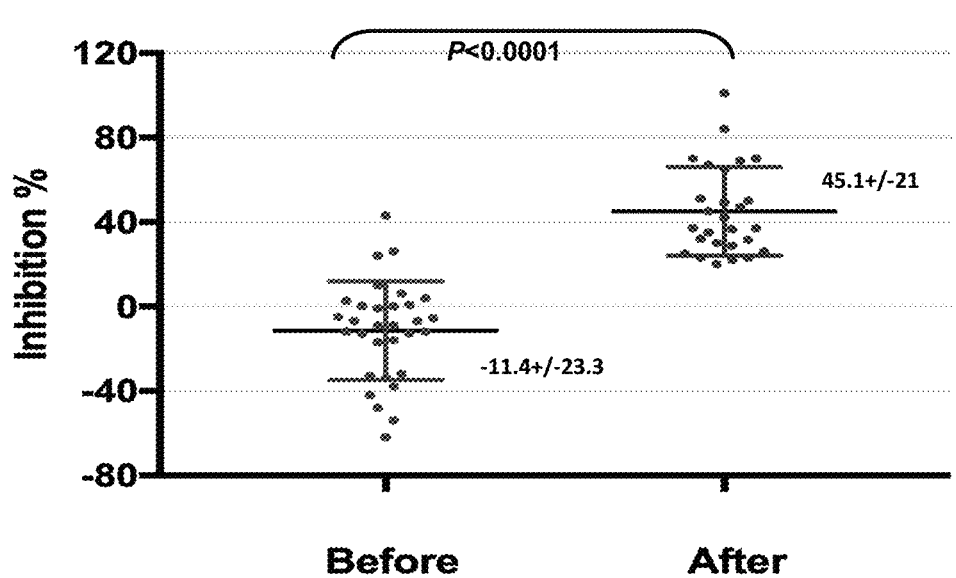

It has been found that patients suffering from the auto-immune diseases namely lupus including both systemic lupus erythematosus (SLE) and cutaneous lupus erythema-tosus (CLE) have the same correctable defect of HLA-E restricted CD8+ Treg cells as that in the patients suffering from T1D as shown in FIG. 4, which demonstrates that the defect can be corrected ex-vivo by the same therapeutic composition of the present invention in the same way as used for the T1D patients as described in this application.

Accordingly, the same therapeutic composition may be administered to treat the lupus patients with the same dosing regimen as used to treat T1D in Example 7 or a different regimen that is to be adjusted by a person of ordinary skill in the art depending on the patient's physiological condi-tions, age, gender or prognosis of the autoimmune disease.

Example 12. Treatment of Vitiligo

Figure 5A:
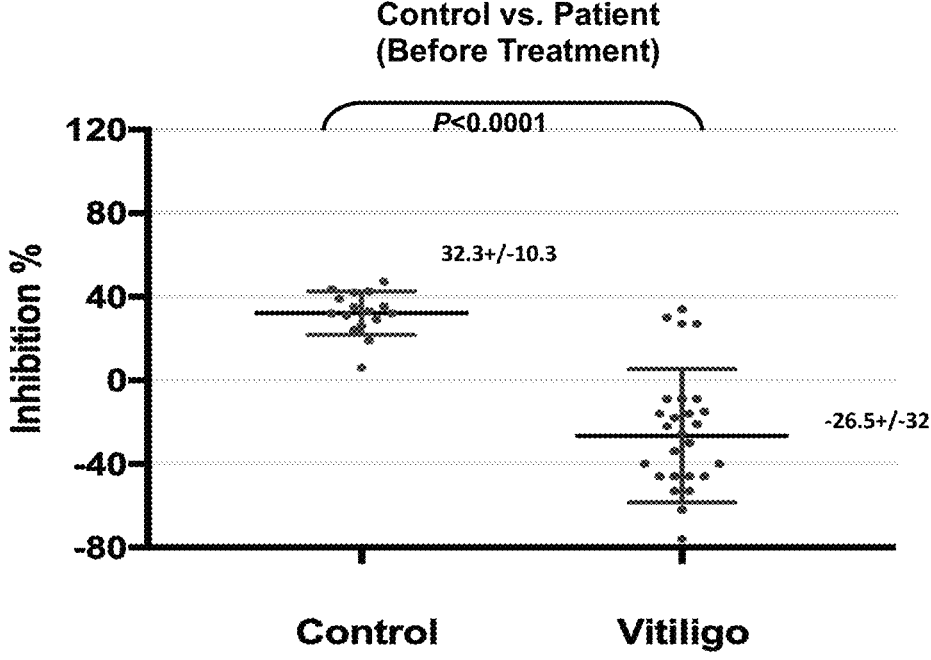
FIGS. 5A-5C show results from a CD8+ Treg cell specificity assay as set forth in Example 12. The CD8+ Treg cells from vitiligo patients are functionally defective when compared with the normal functional CD8+ Treg cells from healthy individuals prior to treatment with the therapeutic agent of the present invention, whereas the function of the defective CD8+ Treg cells from the vitiligo patients was corrected or restored after the treatment. A. BEFORE therapy, the readings between "normal" (N=16) and "patients" (N=27) are statistically significant, P<0.0001. B. The "control" group showed normal pathway function BEFORE therapy (N=16), and statistically non-distinguishable AFTER therapy (N=12), P=0.1392. C. The "patient" group (N=27) showed defective pathway function BEFORE therapy, and the defect was corrected AFTER therapy, showing statistically significant on the effect of the treatment, P<0.0001.
Figure 5B:
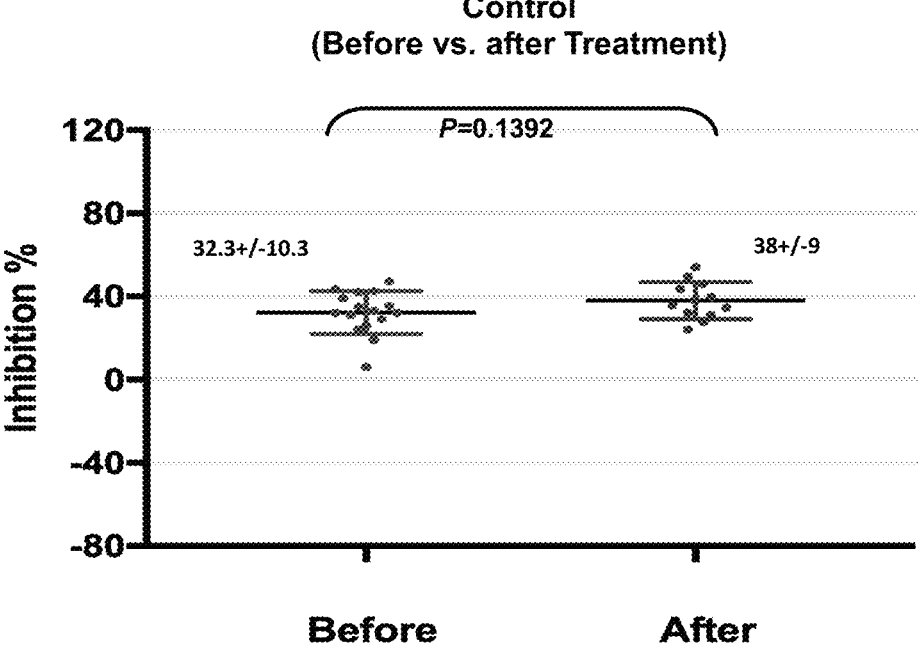
Figure 5C:
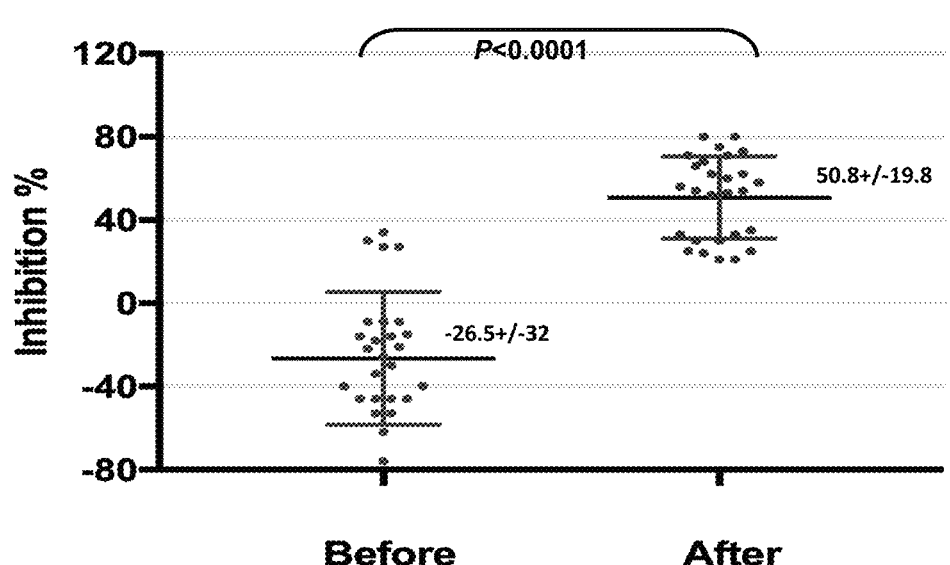

It has been found that patients suffering from the auto-immune diseases namely vitiligo including both segmental and non-segmental vitiligo have the same correctable defect of HLA-E restricted CD8+ Treg cells as that in the patients suffering from T1D as shown in FIG. 5, which demonstrates that the defect can be corrected ex-vivo by the same thera-peutic composition of the present invention in the same way as used for the T1D patients as described in this application.

Accordingly, the same therapeutic composition may be administered to treat the vitiligo patients with the same dosing regimen as used to treat T1D in Example 7 or a different regimen that is to be adjusted by a person of ordinary skill in the art depending on the patient's physi-ological conditions, age, gender or prognosis of the auto-immune disease.

Example 13. Treatment of Dermatomyositis

Figure 6A:
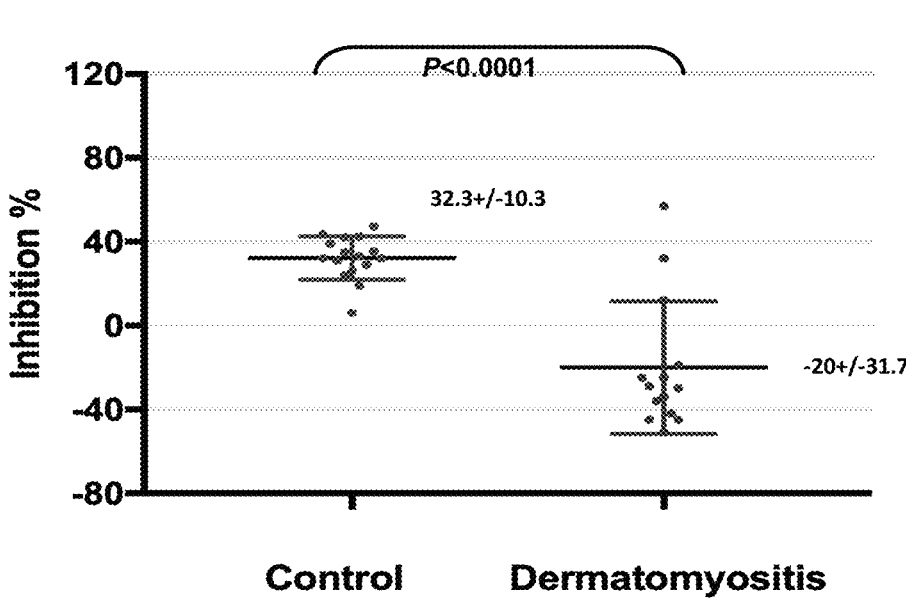
FIGS. 6A-6C show results from a CD8+ Treg cell specificity assay as set forth in Example 13. The CD8+ Treg cells from dermatomyositis (DM) patients are functionally defective when compared with the normal functional CD8+ Treg cells from healthy individuals prior to treatment with the therapeutic agent of the present invention, whereas the function of the defective CD8+ Treg cells from the DM patients was corrected or restored after the treatment. A. BEFORE therapy, the readings between "normal" (N=16) and "patients" (N=14) are statistically significant, P<0.0001. B. The "control" group showed normal pathway function BEFORE therapy (N=16), and statistically non-distinguishable AFTER therapy (N=12), P=0.1392. C. The "patient" group (N=14) showed defective pathway function BEFORE therapy, and the defect was corrected AFTER therapy, showing statistically significant on the effect of the treatment, P<0.0001.
Figure 6B:
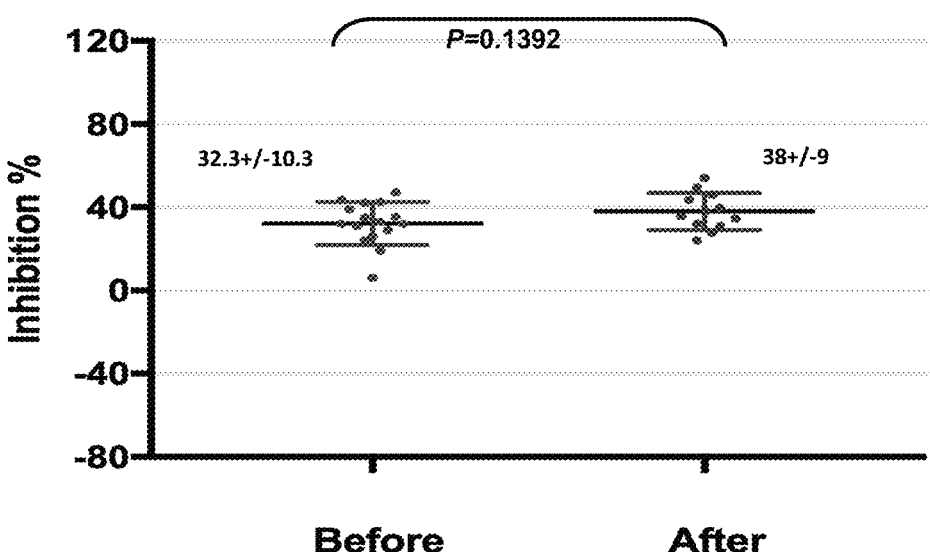
Figure 6C:
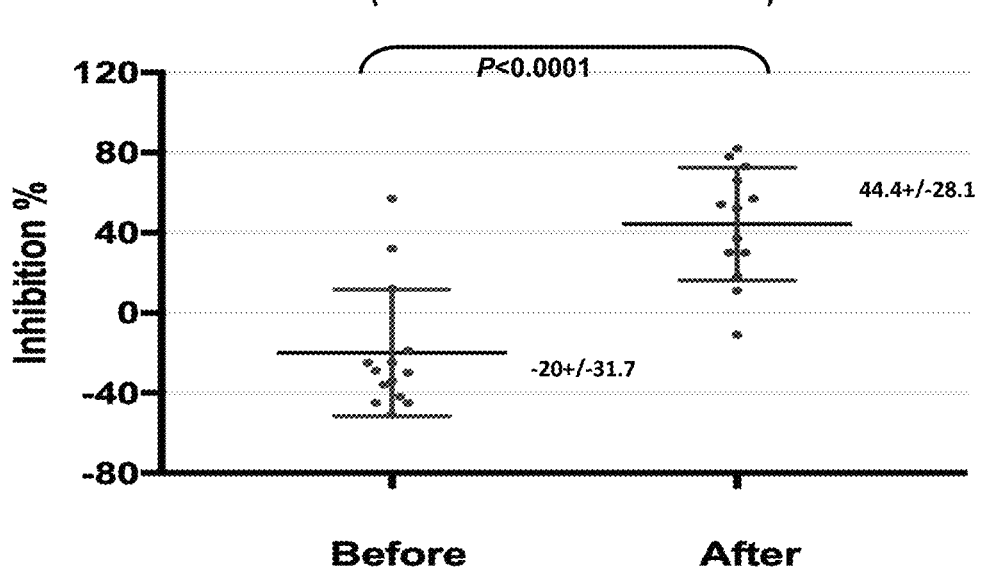

It has been found that patients suffering from the auto-immune diseases namely dermatomyositis (DM) have the same correctable defect of HLA-E restricted CD8+ Treg cells as that in the patients suffering from T1D as shown in FIG. 6, which demonstrates that the defect can be corrected ex-vivo by the same therapeutic composition of the present invention in the same way as used for the T1D patients as described in this application.

Accordingly, the same therapeutic composition may be administered to treat the DM patients with the same dosing regimen as used to treat T1D in Example 7 or a different regimen that is to be adjusted by a person of ordinary skill in the art depending on the patient's physiological condi-tions, age, gender or prognosis of the autoimmune disease.

Example 14. Treatment of Pemphigus

Figure 7A:
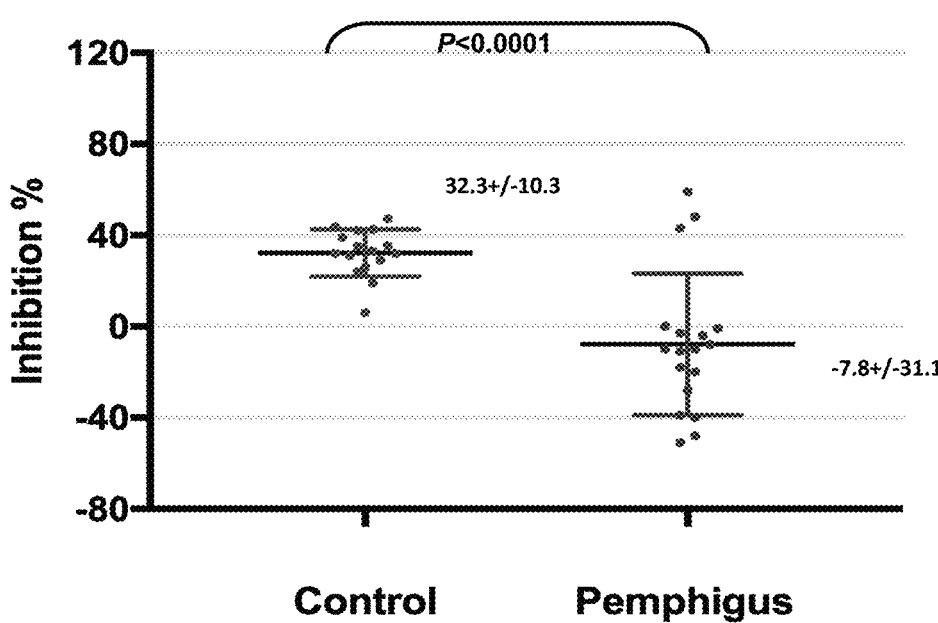
FIGS. 7A-7C show results from a CD8+ Treg cell specificity assay as set forth in Example 14. The CD8+ Treg cells from Pemphigus patients are functionally defective when compared with the normal functional CD8+ Treg cells from healthy individuals prior to treatment with the therapeutic agent of the present invention, whereas the function of the defective CD8+ Treg cells from the DM patients was corrected or restored after the treatment. A. BEFORE therapy, the readings between "normal" (N=16) and "patients" (N=18) are statistically significant, P<0.0001. B. The "control" group showed normal pathway function BEFORE therapy (N=16), and statistically non-distinguishable AFTER therapy (N=14), P=0.1392. C. The "patient" group (N=18) showed defective pathway function BEFORE therapy, and the defect was corrected AFTER therapy, showing statistically significant on the effect of the treatment, P<0.0001.
Figure 7B:
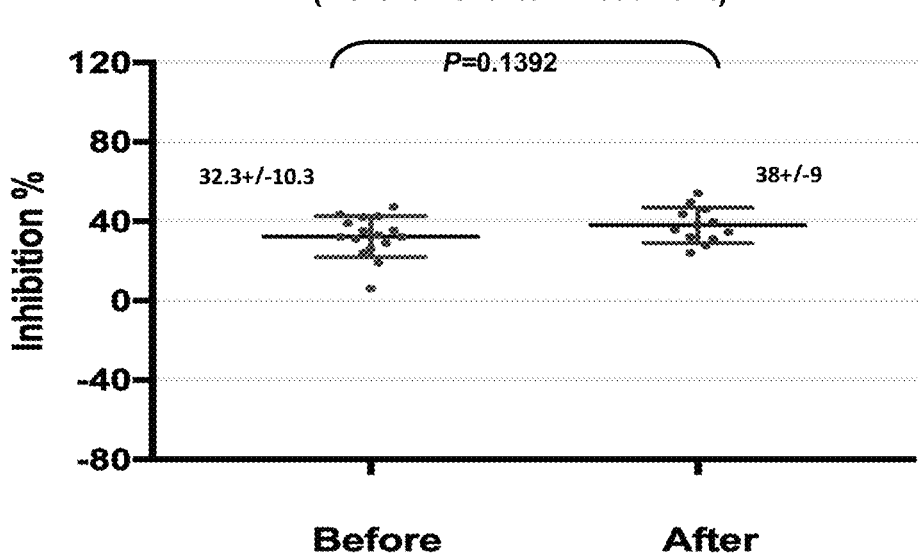
Figure 7C:
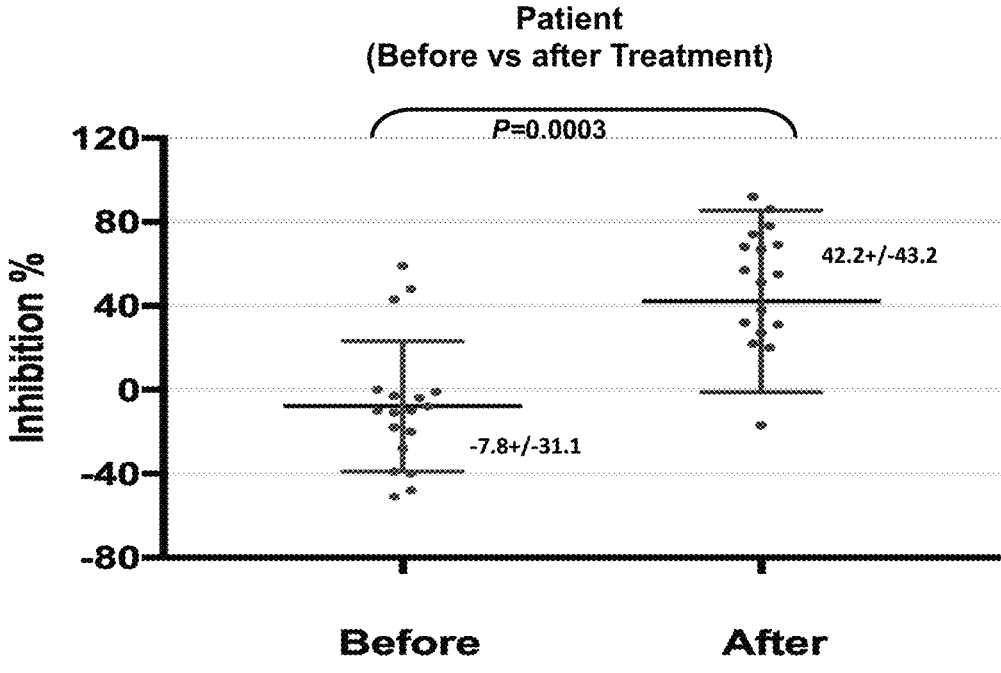

It has been found that patients suffering from the auto-immune diseases namely Pemphigus have the same correct-able defect of HLA-E restricted CD8+ Treg cells as that in the patients suffering from T1D as shown in FIG. 7, which demonstrates that the defect can be corrected ex-vivo by the same therapeutic composition of the present invention in the same way as used for the T1D patients as described in this application.

Accordingly, the same therapeutic composition may be administered to treat the Pemphigus patients with the same dosing regimen as used to treat T1D in Example 7 or a different regimen that is to be adjusted by a person of ordinary skill in the art depending on the patient's physi-ological conditions, age, gender or prognosis of the auto-immune disease.

Example 15. Treatment of Secondary-Progressive Multiple Sclerosis (SPMS)

Figure 8A:
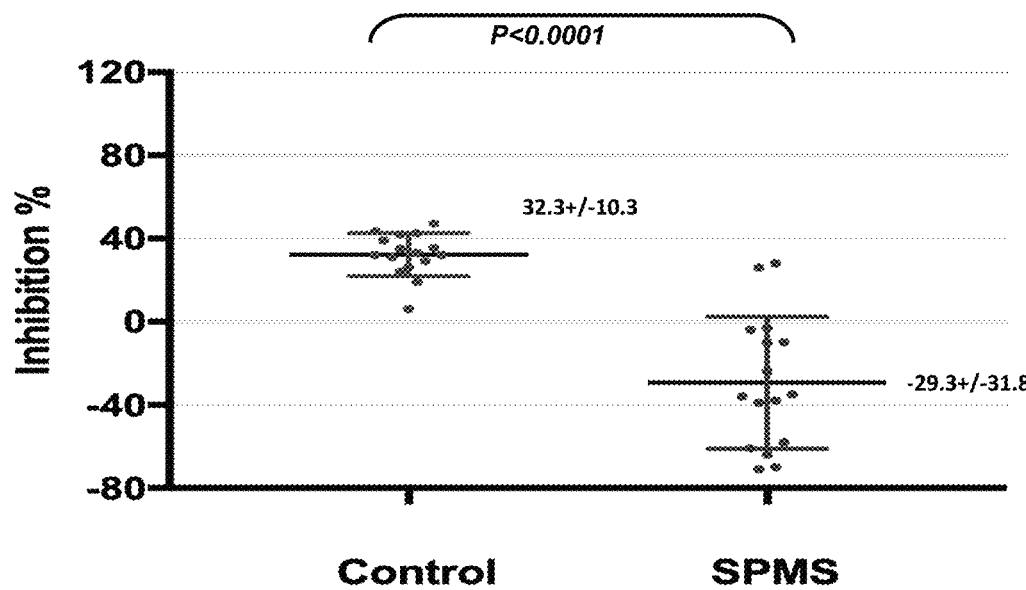
FIGS. 8A-8C show results from a CD8+ Treg cell specificity assay as set forth in Example 15. The CD8+ Treg cells from most of clinically diagnosed multiple sclerosis (MS) patients, whom were randomly tested, diagnosed as SPMS (secondary-progressive multiple sclerosis), were functionally defective when compared with the normal functional CD8+ Treg cells from healthy individuals prior to treatment with the therapeutic agent of the present invention, whereas the function of the defective CD8+ Treg cells from the majority of the MS patients tested was corrected or restored after the treatment. A. BEFORE therapy, the readings between "normal" (N=16) and "SPMS patients" (N=16) are statistically significant, P<0.0001. B. The "control" group showed normal pathway function BEFORE therapy (N=16), and statistically non-distinguishable AFTER therapy (N=12), P=0.1392. C. The "patient" group (N=16) showed defective pathway function BEFORE therapy, and corrected defect AFTER therapy, showing statistically significant on the effect of the treatment, P<0.0001.
Figure 8B:
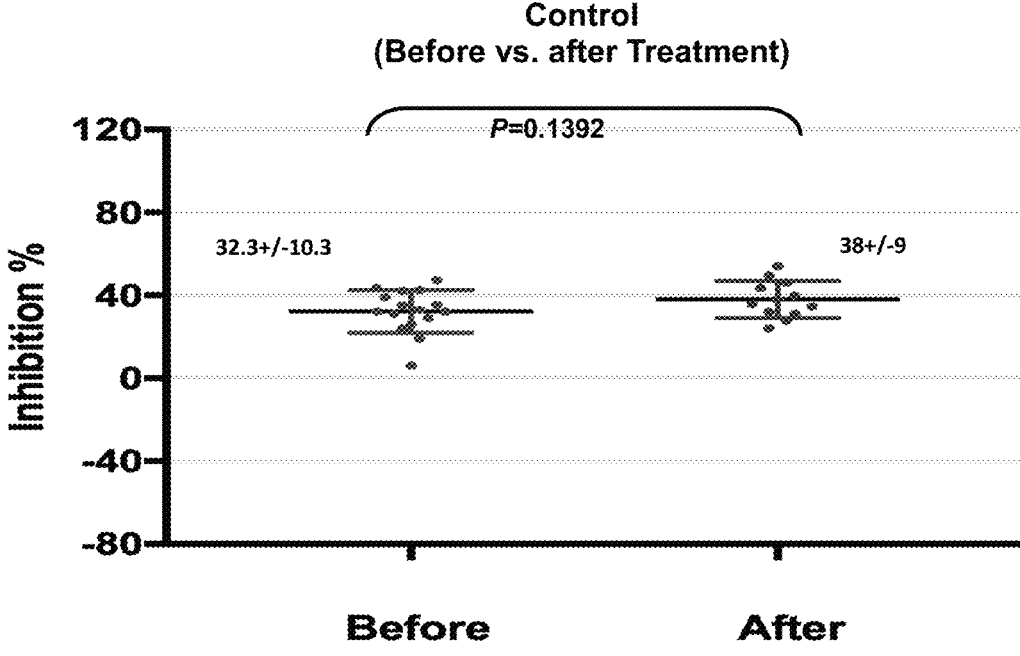
Figure 8C:
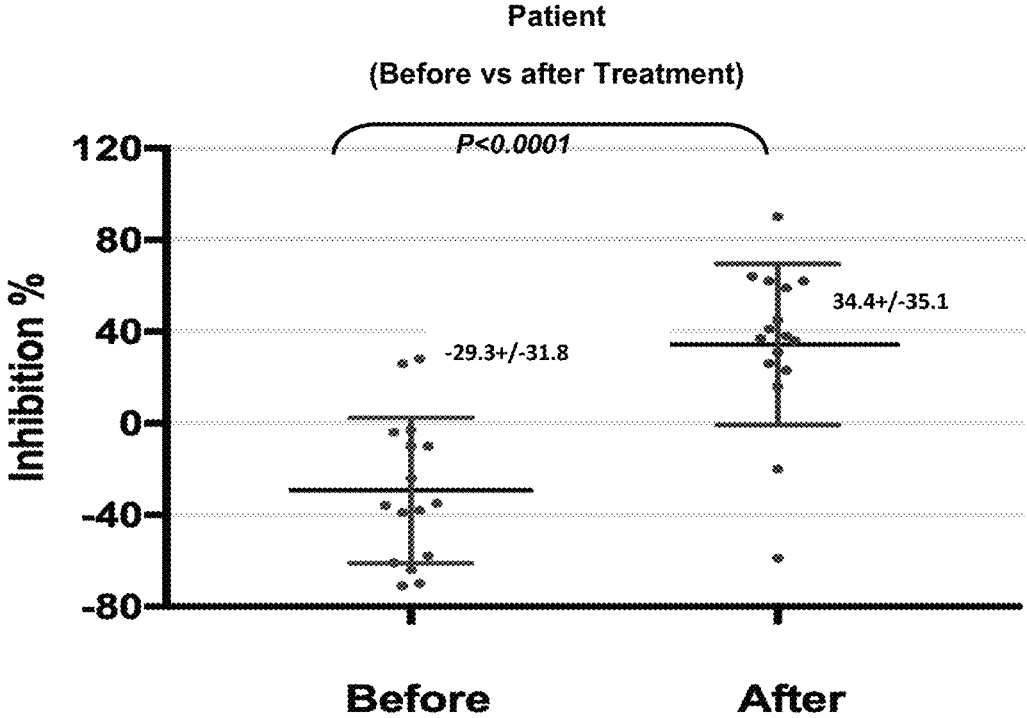

It has been found that patients suffering from the auto-immune diseases namely SPMS have the same correctable defect of HLA-E restricted CD8+ Treg cells as that in the patients suffering from T1D as shown in FIG. 8, which demonstrates that the defect can be corrected ex-vivo by the same therapeutic composition of the present invention in the same way as used for the T1D patients as described in this application.

Accordingly, the same therapeutic composition may be administered to treat the SPMS patients with the same dosing regimen as used to treat T1D in Example 7 or a different regimen that is to be adjusted by a person of ordinary skill in the art depending on the patient's physi-ological conditions, age, gender or prognosis of the auto-immune disease.

Example 16. Double-Blind, Randomized Study of Efficacy of the Cell-Based Therapy in Patients with Early Relapsing Form of Multiple Sclerosis (RMS)/Clinically Isolated Syndrome (CIS)

A 6-month placebo-controlled RMS/CIS Phase 2 study is conducted to investigate the efficacy of the therapeutically peptide-loaded dendritic cell (DC) formulation ("Therapeutic Agent") as described in Example 7 in early stage of RMS/CIS patients, who are ex vivo responders to the potency assay. A study (open label) extension phase is also proposed to compare the pharmacodynamic response. After 6 months, patients in the placebo group are switched to the Therapeutic Agent in an open label phase for a further 6 months.

The potency assay, also known as CD8+ T cell inhibition assay, is used to identify patients having a defect in HLA-E restricted Treg pathway, which defect can be corrected ex vivo, for example, with the Therapeutic Agent as described in Example 1. Only clinical diagnosed MS patients fulfilling both criteria are considered "ex vivo responders".

The study includes approximately 90 subjects, who are ex vivo responders identified as having a defect in HLA-E-restricted CD8+ T cell function associated with neuron cell destruction assessed by clinical detection, which defect can be corrected by, for example, an in vitro procedure set forth in the present application.

Approximately 90 subjects are randomized in a 2:1 ratio for the Therapeutic Agent to Placebo as follows:

Therapeutic Agent: 60 subjects to receive the Therapeutic Agent by intravenous infusion administration.

Placebo control: 30 subjects to receive placebo infusion solution only through intravenous infusion administration.

Each subject is subject to a treatment with the Therapeutic Agent or placebo. Each treatment includes three consecutive doses of the Therapeutic Agent or placebo, which are administered to the subjects by intravenous infusion with one-month (+/−7 days) intervals between two consecutive doses, i.e., baseline (Day 1), Month 1, and Month 2. Infusions must be administered at least 21 days apart. The primary time point for assessment and statistical analysis of the efficacy of the Therapeutic Agent is 4 months post-last dose (i.e., at Month 6), with longer-term follow-up through 10 months post-last dose (i.e., at Month 12).

Number of subjects (planned):

Up to approximately 90 subjects are randomized (in a 2:1 ratio for the Therapeutic Agent:Placebo), and thus up to approximately 60 subjects are treated with the Therapeutic Agent and 30 subjects are treated with Placebo.

Investigational product, dosage and mode of administration:

Nature of the active ingredient: The Therapeutic Agent for each subject is an individualized preparation of the autologous immature dendritic cells from the subject's adherent primary monocytes, which are cultured with GM-CSF and IL-4 for 6 days, and loaded passively with a peptide from the hHsp60sp (SEQ ID NO: 1) in vitro before being suspended for intravenous infusion into the subject, as described in Examples 2-4.

Formulation of dosage: The Therapeutic Agent is cryopreserved in infusible cryomedia in cryopreservation 20 mL bags. Each infusion bag contains between $7\times10^6$ and $10\times10^6$ cells. Each subject randomized to the Therapeutic Agent has three such bags manufactured for infusion as described above at, for example Examples 2-4. The cryopreserved cells are manufactured at the Dana Farber Cancer Institute Cell Manipulation Core Facility (DFCI-CMCF), at Harvard, Boston, and are transported to the site for infusion.

Route of administration: Each infusion is administered intravenously over 15-20 minutes.

Frequency of administration: Three (3) infusions are administered approximately 30 (+/−7) days apart. Infusions must be at least 21 days apart.

Duration of treatment: There are three pre-defined periods in this study.

Screening and cell collection period lasts up to 3 months.

Treatment period consists of 3 doses, each about 30 days apart (e.g., Baseline, Month 1, Month 2). Thus, the treatment period is defined to be about 2 months in duration. Post-Treatment Follow-up Period extends approximately 10 additional months (and thus through Month 12 of the study).

Reference therapy, dosage and mode of administration:

The Placebo consists of 18 mL saline and 2 mL of 10% dimethyl sulfoxide (DMSO) in 25% Human Serum Albumin (HSA) mixture in 20 mL KryoSure bags, while the investigational drug, the Therapeutic Agent, consists of 20 ml of cell suspension in KryoSure bag.

Both the Therapeutic Agent and Placebo are given by similar intravenous infusion and masked with an opaque sleeve before and during administration to remain blinded.

Primary Endpoint (efficacy):

The primary endpoint is new or enlarging T2 lesions at month 6 (with reference to month 3).

There is a total of five scans of new or enlarging T2 lesions at 3, 6, 9, 12 months of each subject over the course of the year.

Durability of treatment effect can be assessed by scanning at months 9 and 12.

The number of new and enlarging T2 lesions on MRI scans is measured by the central MRI reading center, which is blinded to treatments.

Secondary Endpoints (efficacy):

New and enlarging T2 new lesions are measured at the end of the study after 1 year on MRI compared to new/enlarging T2 at Months 3, 6, 9 and 12.

Time to first relapse. Time to first relapse is the period until the first relapse is confirmed from the first study cellular therapy injection.

Assessment of neurofilament light protein (NfL) at Months 3, 6, 9 and 12, as compared with its baseline.

Assessment of glial fibrillary acidic protein (GFAP) at Months 3, 6, 9 and 12, as compared with its baseline.

Assessment of the HLA-E restricted CD8+ regulatory T cell function ("potency assay") at Months 3, 6, 9 and 12, as compared with its baseline.

Statistical methods:

Sample Size

The sample size is designed to detect a 60% or more reduction in the risk of new/enlarging T2 lesions for each subject calculated as the sum of the new lesions from Months 3 to 6, and to 9 and 12 MRIs with the primary endpoint at 6 months. The expected ratio of the average new/enlarging T2 in the Therapeutic Agent arm is expected to be at most 0.40 of that of the Placebo arm. The allocation ratio of subjects to the Therapeutic Agent and Placebo is set at 2 to 1 to provide more information on the results in the Therapeutic Agent arm as well as providing a greater incentive for patients to enroll. Subjects in the Placebo arm are allowed to cross-over to the Therapeutic Agent at 6 months. The Alpha (the probability of rejecting the null hypothesis when it is true) is 0.05. The Power is set at 80% (i.e., the probability of rejecting the null hypothesis when it is false). The sample size is calculated based on the ratio of two negative binomial new/enlarging T2 rates using the Wald Test (PASS Version 14.0.14).

The null and alternative Hypotheses are:

$H_0: RR=1$ vs. $H_a: RR \neq 1$

The Posenimode Phase 2 study showed an average of 0.7 new/enlarging T2 total over three MRIs or 0.23 per scan; the average per lesion count from the Phase 2 Oftatumamab trial of 1.04 new/enlarging T2 over 3 scans or 0.35 per scan and the Ozanimod Phase 2 trial showed an average of 8.6 over 5 scans or 1.7 per scan. Given that this is a Placebo controlled trial, it is possible that subjects with the most severe MRIs in terms of lesion counts may be excluded. Thus, we reduce the expected average count to be conservative. We assume that the Placebo arm experiences an average of 3 new/enlarging T2 lesions at 6 months. If the number of new/enlarging T2 lesions is higher, the power is increased. To accommodate the skewness often seen in lesion counts, a negative binomial distribution is used with a dispersion parameter set to 1.2. For a two-sided Wald test of the null hypothesis H0: RR=1 vs. the alternative Ha: RR≠1, samples of 25 subjects in the Placebo Group and 50 subjects in the Therapeutic Agent Group achieve 81% power to detect an event rate ratio (RR) of 0.40 or smaller, when the event rate in the Placebo Group ($\lambda 1$) is 3 new/enlarging T2, the average exposure time in both groups ($\mu(t)$) is 6 months and the two-sided significance level (alpha) is 0.05 with the null hypothesis variance calculated using maximum likelihood estimation. Although we expect few dropouts given the 6-month duration of the study, we increase the sample size to accommodate up to 15% dropouts. Thus 75/0.85=88.2 or 90 subjects are randomized with 30 assigned to the Placebo Group and 60 assigned to the Therapeutic Agent Group.

Analysis Timing

The primary analysis for this study is performed after the last subject has completed the Month 6 study visit, at which time the study database is locked, and the treatment allocation codes unblinded for analysis. These analyses form the primary basis for the assessment of the study objectives.

Continuing data collection through the long-term follow-up is performed through Month 12 of the study.

Efficacy Assessment:

New and/or enlarging T2 lesions measured by MRI (new/enlarging T2), after 6 months are assessed along with the secondary objectives.

Primary Analyses:

The primary analysis compares the ratio of risk of new/enlarging T2 using the negative binomial distribution via PROC GENMOD in SAS (version 9.4 or higher) with covariates of age, sex, baseline lesion count (Gadolinium plus T2 lesions) and treatment group. The analysis utilizes the new/enlarging T2 over the period 3 to 6 months.

Secondary Analyses:

Durability of treatment is assessed by examining the change from the new/enlarging T2 at 6 months in the Therapeutic Agent randomized group to the new/enlarging T2 at the month 12 MRI. The durability is assessed by whether or not the change is within a 90% confidence interval of the estimated mean count of new/enlarging T2 at month 6 from within the Therapeutic Agent Group.

The negative binomial distribution is also used to assess the annualized relapse rate as done for the primary. Baseline lesion counts are used as a covariate instead of prior relapses since these are naïve subjects unlikely to have full relapse histories. Time to first relapse is assessed using a Cox model with the same covariates and a descriptive analysis using a Kaplan Meier analysis. The laboratory values NfL, GFAP, and CD8+ cells are assessed using the log of the values using mixed models repeated measures.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

SEQUENCE LISTING

```
Sequence total quantity: 4
SEQ ID NO: 1          moltype = AA  length = 9
FEATURE               Location/Qualifiers
source                1..9
                      mol_type = protein
                      organism = Homo sapiens
SEQUENCE: 1
QMRPVSRVL                                                    9

SEQ ID NO: 2          moltype = AA  length = 9
FEATURE               Location/Qualifiers
source                1..9
                      mol_type = protein
                      organism = Homo sapiens
SEQUENCE: 2
VMAPRTVLL                                                    9

SEQ ID NO: 3          moltype =    length =
SEQUENCE: 3
000

SEQ ID NO: 4          moltype = AA  length = 9
FEATURE               Location/Qualifiers
source                1..9
                      mol_type = protein
                      organism = synthetic construct
SEQUENCE: 4
AMAPRTLLL                                                    9
```

What is claimed:

1. A method for preparing an autologous dendritic cell/hHsp60sp complex for correction of defective HLA-E restricted CD8+ Treg cells, comprising:

(a) preparing autologous immature dendritic cells from a test human individual having defective HLA-E restricted CD8+ Treg cells, wherein the prepared autologous immature dendritic cells are loaded with human heat shock protein 60 signal peptide (hHsp60sp) and fixed with paraformaldehyde (PFA) to form an autologous dendritic cell/hHsp60sp complex;

(b) freshly isolating defective HLA-E restricted CD8+ Treg cells from the test human individual ("test HLA-E restricted CD8+ Treg cells");

(c) testing the prepared autologous dendritic cell/hHsp60sp complex of step (a) for correcting the test HLA-E restricted CD8+ Treg cells in a CD8+ T cell specificity assay, wherein the CD8+ T cell specificity assay comprises specific target cells from the cell line having the ATCC accession number PTA-127256 and control target cells from the cell line having the ATCC accession number PTA-127257, wherein the CD8+ T cell specificity assay comprises:

(i) activating the test HLA-E restricted CD8+ Treg cells with the prepared autologous dendritic cell/hHsp60sp complex, whereby activated test HLA-E restricted CD8+ Treg cells are produced;

(ii) determining the percentage of maximum inhibition for the specific target cells and the activated test HLA-E restricted CD8+ Treg cells, (iii) activating the test HLA-E restricted CD8+ Treg cells with fixed autologous immature dendritic cells loaded with B7sp, whereby activated control HLA-E restricted CD8+ Treg cells are produced;

(iv) determining the percentage of maximum inhibition for the control target cells and the activated control HLA-E restricted CD8+ Treg cells, and (v) determining a normalized percentage of the maximum inhibition for the test HLA-E restricted CD8+ Treg cells by subtracting the percentage of maximum inhibition for the control target cells and the activated control HLA-E restricted CD8+ Treg cells from the percentage of maximum inhibition for the specific target cells and the activated test HLA-E restricted CD8+ Treg cells, wherein a normalized percentage of maximum inhibition for the test HLA-E restricted CD8+ Treg cells greater than 50% of that for the control HLA-E restricted CD8+ Treg cells indicates that the prepared autologous immature dendritic cells correct the test HLA-E restricted CD8+ Treg cells; and (d) obtaining the autologous dendritic cell/hHsp60sp complex that corrects the test HLA-E restricted CD8+ Treg cells in step (c).

2. The method of claim 1, wherein the prepared autologous immature dendritic cells are fixed with 2% PFA in step (a).

3. The method of claim 1, wherein the composition is formulated for intravenous administration to the subject.

4. The method of claim 3, wherein the subject suffers from an autoimmune disease.

5. The method of claim 4, wherein the autoimmune disease is selected from the group consisting of type 1 diabetes (T1D), multiple sclerosis (MS), psoriasis, rheumatoid arthritis, lupus, vitiligo, pemphigus and dermatomyositis.

6. The method of claim 4, wherein the autoimmune disease is type 1 diabetes (T1D).

7. The method of claim 4, wherein the autoimmune disease is multiple sclerosis (MS).

8. The method of claim 1, wherein step (c) further comprises:

(1) obtaining a first cell population having an equal number of the specific target cells from the cell line having the ATCC accession number PTA-127256 and B721 cells;

(2) culturing the first cell population in the presence of the activated test HLA-E restricted CD8+ Treg cells; and (3) quantifying proliferation of the specific target cells in the first cell population of (2).

9. The method of claim 1, wherein step (c) further comprises:

(1) obtaining a second cell population having an equal number of the control target cells from the cell line having the ATCC accession number PTA-127257 and B721 cells;

(2) culturing the second cell population in the presence of the activated control HLA-E restricted CD8+ Treg cells; and (3) quantifying proliferation of the specific target cells in the second cell population of (2).

* * * * *